United States Patent
Shapiro et al.

(10) Patent No.: US 11,137,462 B2
(45) Date of Patent: Oct. 5, 2021

(54) SYSTEM AND METHOD FOR QUANTIFYING CELL NUMBERS IN MAGNETIC RESONANCE IMAGING (MRI)

(71) Applicant: Board of Trustees of Michigan State University, East Lansing, MI (US)

(72) Inventors: Erik Shapiro, Okemos, MI (US); Muhammad Jamal Afridi, Woodbury, MN (US); Arun Ross, East Lansing, MI (US); Xiaoming Liu, Okemos, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 415 days.

(21) Appl. No.: 15/620,545

(22) Filed: Jun. 12, 2017

(65) Prior Publication Data
US 2017/0356976 A1    Dec. 14, 2017

Related U.S. Application Data

(60) Provisional application No. 62/348,248, filed on Jun. 10, 2016.

(51) Int. Cl.
*A61B 5/055*    (2006.01)
*A61B 5/00*    (2006.01)
(Continued)

(52) U.S. Cl.
CPC .......... *G01R 33/5601* (2013.01); *A61B 5/055* (2013.01); *A61B 5/7267* (2013.01);
(Continued)

(58) Field of Classification Search
CPC ............ G01R 33/5601; G01R 33/5608; G06K 9/00147; A61B 5/7267; A61B 5/055
See application file for complete search history.

(56) References Cited

U.S. PATENT DOCUMENTS

| | | | |
|---|---|---|---|
| 6,246,782 B1 * | 6/2001 | Shapiro | G06T 7/0012 128/925 |
| 2010/0002920 A1 * | 1/2010 | Cosatto | G06K 9/00147 382/128 |

(Continued)

OTHER PUBLICATIONS

Xing, E. P., et al., "Distance metric learning with application to clustering with side-information," Advances in neural information processing systems, vol. 15, pp. 505-512, 2003.

(Continued)

*Primary Examiner* — Serkan Akar
*Assistant Examiner* — Aminah Asghar
(74) *Attorney, Agent, or Firm* — Quarles & Brady LLP

(57) ABSTRACT

A system and method are provided for tracking magnetically-labeled substances, such as transplanted cells, in subjects using magnetic resonance imaging (MRI). The method includes obtaining a quantity of a substance that comprises an MRI contrast compound or is otherwise magnetically-labeled for purposes of an MRI scan, administering the substance into a region of interest of a subject, performing an imaging scan of a portion of the subject comprising the region of interest, obtaining an imaging data set from the scan, reducing the dataset into pixel groupings based on intensity profiles, where the pixel groupings have a pixel size larger than the expected pixel size of a unit of the MRI contrast compound or magnetically-labeled substance, extracting candidate pixel matrices from the imaging data, training a machine learning (ML) module by using the candidate pixel matrices, quantifying the presence, number and/or location of units of the substance within the subject by using the ML module, and displaying a visual representation of an identification of the substances within the subject as a result of using the ML module.

21 Claims, 41 Drawing Sheets
(31 of 41 Drawing Sheet(s) Filed in Color)

(51) Int. Cl.
  A61K 49/18   (2006.01)
  G06K 9/62    (2006.01)
  G01R 33/56   (2006.01)
  G06K 9/00    (2006.01)
  G01R 33/54   (2006.01)

(52) U.S. Cl.
  CPC ............ *A61B 5/742* (2013.01); *A61B 5/7475* (2013.01); *A61K 49/1896* (2013.01); *G01R 33/5608* (2013.01); *G06K 9/0014* (2013.01); *G06K 9/00147* (2013.01); *G06K 9/6273* (2013.01); *A61B 2576/00* (2013.01); *G01R 33/546* (2013.01)

(56) References Cited

U.S. PATENT DOCUMENTS

| | | | | |
|---|---|---|---|---|
| 2010/0158332 | A1* | 6/2010 | Rico | A61B 5/7264 382/128 |
| 2012/0004530 | A1* | 1/2012 | Liu | G01R 33/50 600/410 |
| 2015/0213598 | A1* | 7/2015 | Madabhushi | G06T 7/0012 382/128 |
| 2015/0238148 | A1* | 8/2015 | Georgescu | A61B 5/7267 600/408 |
| 2015/0377997 | A1* | 12/2015 | Zabow | G01R 33/5601 324/309 |
| 2016/0148077 | A1* | 5/2016 | Cox | G06K 9/00288 382/159 |
| 2016/0180157 | A1* | 6/2016 | Alcoverro Vidal | G06K 9/00201 382/103 |
| 2017/0319278 | A1* | 11/2017 | Trayanova | A61B 34/10 |
| 2018/0171388 | A1* | 6/2018 | Thomann | C12Q 1/689 |
| 2018/0174311 | A1* | 6/2018 | Kluckner | G06K 9/3233 |

OTHER PUBLICATIONS

Yosinski, J., et al., "How transferable are features in deep neural networks?." in Advances in Neural Information Processing Systems, pp. 3320-3328. 2014.
Zeiler, M.D., et al., Visualizing and understanding convolutional networks. In: Computer vision IECCV 2014. Springer (2014) 818-833.
Zhang, M. et al., "Small blob identification in medical images using regional features from optimum scale." IEEE transactions on biomedical engineering 62.4 (2015): 1051-1062.
Zhou, R., et al., (2010). "SWIFT detection of SPIOlabeled stem cells grafted in the myocardium." Magnetic Resonance in Medicine 63, No. 5 : 1154-1161.
Afridi, M. J., et al., (2015) Automatic in vivo Cell Detection in MRI, in Proc. 18th International Conference on Medical Image Computing and Computer Assisted Intervention (MICCAI), Munich, Germany.
Afridi, M.J. et al., "An Automated System for Plant-Level Disease Rating in Real Fields." in Pattern Recognition (ICPR), 2014 22nd International Conference on, pp. 148-153. IEEE, 2014.
Agrawal, P., et al., Learning to see by moving. In: Proceedings of the IEEE International Conference on Computer Vision. (2015) 37-45.
Ammar, H.B. et al., "An automated measure of mdp similarity for transfer in reinforcement learning." Workshops at the Twenty-Eighth AAAI Conference on Artificial Intelligence. 2014.
Azizpour, H., et al., From generic to specific deep representations for visual recognition. In IEEE Conference on Computer Vi-sion and Pattern Recognition (CVPR), 2015.
Basu, S., et al., "A probabilistic framework for semi-supervised clustering," in Proceedings of the tenth ACM SIGKDD international conference on Knowledge discovery and data mining, pp. 59-68, ACM, 2004.

Bitvai Z., et al "Non-linear text regression with a deep convolutional neural network," vol. 2: Short Papers, vol. 1, No. x1, p. 180, 2015.
Bouckaert, R., et al., (2013) : Weka manual for version 3-7-8.
Chen, H., et al., Standard plane localization in fetal ultrasound via domain transferred deep neural networks. IEEE Journal of Biomedical and Health Informatics, 19, 2015.
Chen, J. et al., "Boosting with side information," in Computer Vision—ACCV 2012, pp. 563-577, Springer, 2012.
Dalal, N., et al.,(Jun. 2005). Histograms of oriented gradients for human detection. In Computer Vision and Pattern Recognition, CVPR, IEEE (vol. 1, pp. 886-893).
Deng, J., et al., Imagenet: A large-scale hierarchical image database. In IEEE Conference on Computer Vision and Pattern Recognition (CVPR), pp. 248-255, 2009.
Foti, D., et al., "Differentiating neural responses to emotional pictures: evidence from temporal-spatial pca," Psychophysiology, vol. 46, No. 3, pp. 521-530, 2009.
Hall, M. A. (1999). Correlation-based feature selection for machine learning (Doctoral dissertation, the University of Waikato).
He, K., et al., Delving deep into rectifiers: Surpassing human-level performance on imagenet classification. In: Proceedings of the IEEE International Conference on Computer Vision. (2015) 1026-1034.
Heyn, C.,, et al., In vivo magnetic resonance imaging of single cells in mouse brain with optical validation. Magnetic Resonance in Medicine 55(1), 23{29 (2006).
Janning, R., et al., "Hnnp—a hybrid neural network plait for improving image classification with additional side information," in Tools with Artificial Intelligence (ICTAI), 2013 IEEE 25th International Conference on, pp. 24-29, IEEE, 2013.
Kamper, H., et al.,"Deep convolutional acoustic word embeddings using word-pair side information," arXiv preprint arXiv:1510.01032, 2015.
Krizhevsky, A. et al., Imagenet classification with deep convolutional neural networks. In Advances in Neural Information Processing Systems, pp. 1097-1105, 2012.
Lawrence, S., et al. Face recognition: a convolutional neural-network approach. IEEE Transactions on Neural Networks, 8(1):98-113, Jan. 1997.
Lindvall,O., et al., Stem cell therapy for human neurodegenerative disorders—how to make it work. Nature Medicine, 2004.
Liu, M.-Y. et al., "Entropy rate superpixel segmentation," in IEEE Conference on Computer Vision and Pattern Recognition (CVPR), pp. 2097-2104, 2011.
Long, M., et al. "Learning transferable features with deep adaptation networks," in Proc. International Conference on Machine Learning (ICML 2015), vol. 37, 2015.
Lopez-Paz, D., et al., "Unifying distillation and privileged information," stat, vol. 1050, p. 26, 2016.
Mori,Y, et al., "From cartoon to real time mri: in vivo monitoring of phagocyte migration in mouse brain," Scientific reports, vol. 4, 2014.
Murcia, M.G. et al., "Spatiotemporal dynamics of images with emotional bivalence," in Artificial Computation in Biology and Medicine, pp. 203-212, Springer, 2015.
Oliva, A., et al., (2006). Building the gist of a scene: The role of global image features in recognition. Progress in brain research, 155, 23-36.
Oquab, M., et al., Learning and transferring mid-level image representations using convolutional neural networks. In: Proceedings of the IEEE Conference on Computer Vision and Pattern Recognition. (2014) 1717-1724.
Ozuysal, M., et al., Fast keypoint recognition using random ferns. IEEE T-PAMI 32(3), 448{461 (2010).
Pan, S.J., et al., "A survey on transfer learning." Knowledge and Data Engineering, IEEE Transactions on 22, No. 10 (2010): 1345-1359.
Rodriguez, J.J., et al., Rotation forest: A new classifier ensemble method. IEEE T-PAMI 28(10), 1619{1630 (2006).
Scheirer, W. J., et al., "Perceptual annotation: Measuring human vision to improve computer vision," IEEE Transactions on Pattern Analysis and Machine Intelligence (T-PAMI), vol. 36, Aug. 2014.

(56) References Cited

OTHER PUBLICATIONS

Schmidhuber, J. (2015). Deep learning in neural networks: An overview. Neural Net-works, Elsevier 61, 85-117.

Segers V.F. et al., Stem-cell therapy for cardiac disease. Nature, 451(7181):937-942, 2008.

Shapiro, E. M. et al., Sizing it up: Cellular MRI using micron-sized iron oxide particles. Magnetic Resonance in Medicine, 53(2):329-338, 2005.

Shapiro, E. M., et al., (2006). In vivo detection of single cells by MRI. Magnetic Resonance in Medicine, 55(2), 242-249.

Sharmanska, V., et al., "Learning to transfer privileged information," in Proceedings of the IEEE International Conference on Computer Vision, pp. 825-832, 2013. arXiv preprint arXiv:1410.0389, 2014.

Slotkin, J. R., et al., (2007). Cellular magnetic resonance imaging: nanometer and micrometer size particles for noninvasive cell localization. Neurotherapeutics, 4(3), 428-433.

Smal, I., et al., (2010). Quantitative comparison of spot detection methods in fluorescence microscopy. Transactions on Medical Imaging, IEEE, 29(2), 282-301.

Sorokin, A., et al., Utility data annotation with amazon mechanical turk. In: IEEE Conference on Computer Vision and Pattern Recognition Workshop (CVPRW). (2008).

Strauer B.E. et al., Stem cell therapy in perspective. Circulation, 107(7):929-934, 2003.

Taigman, Y, et al., "Deepface: Closing the gap to human-level performance in face verification." in Computer Vision and Pattern Recognition (CVPR), 2014 IEEE Conference on, pp. 1701-1708. IEEE, 2014.

Tulsiani, S., et al., Pose induction for novel object categories. In: Proceedings of the IEEE International Conference on Computer Vision. (2015) 64-72.

Turk, M., et al., (Jun. 1991). Face recognition using eigenfaces. In Computer Vision and Pattern Recognition, 1991. Proceedings CVPR'91., IEEE (pp. 586-591).

Vapnik V., et al.,"A new learning paradigm: Learning using privileged information," Neural Networks, vol. 22, No. 5, pp. 544-557, 2009.

Vapnik, V., et al., "Learning using hidden information (learning with teacher)," in Neural Networks, 2009. IJCNN 2009. International Joint Conference on, pp. 3188-3195, IEEE, 2009.

Vedaldi A., et al., Matconvnet convolutional neural networks for matlab. arXiv preprint arXiv:1412.4564, 2014.

Wang, Z., et al, "Classifier learning with hidden information," in Proceedings of the IEEE Conference on Computer Vision and Pattern Recognition, pp. 4969-4977, 2015.

Wolf L., et al., "The svm-minus similarity score for video face recognition," in Proceedings of the IEEE Conference on Computer Vision and Pattern Recognition, pp. 3523-3530, 2013.

Wu, Y.L., et al., 2013. Magnetic resonance imaging investigation of macrophages in acute cardiac allograft rejection after heart transplantation. Circulation: Cardiovascular Imaging, 6(6), pp. 965-973.

\* cited by examiner

| Training Data | MRI Data Only | MRI data Only | MRI Data + Other Unrelated Data |
|---|---|---|---|
| | P-1 | P-2 | P-3 |
| Features and Classifier | Fixed | Learned | Fixed or Learned |

FIG. 7

SYSTEM AND METHOD FOR QUANTIFYING CELL NUMBERS IN MAGNETIC RESONANCE IMAGING (MRI)

STATEMENT OF RELATED APPLICATIONS

This application claims the benefit under 35 U.S.C. § 119 of U.S. Provisional Application No. 62/348,248 filed on Jun. 10, 2017, the entire contents of which are incorporated herein by reference.

STATEMENT REGARDING FEDERALLY SPONSORED RESEARCH

This invention was made with government support under OD004362, CA185163, DK107697, and AG041266 awarded by the National Institutes of Health. The government has certain rights in the invention.

BACKGROUND

The present disclosure generally relates to systems and methods for magnetic resonance imaging (MRI). More specifically, the disclosure relates to an MRI system and method that can track, quantify and/or locate units of a substance introduced into a scan subject, and a method for implementing such system. As discussed below, the system and method can be used, for example, to determine such information as how many individual, magnetically-labeled cells remain in a region of interest (e.g., a joint or organ) of a person after therapeutic injection of the cells into the region.

MRI is based on the principle that nuclei possess a magnetic moment that attempts to align itself with the direction of the magnetic field in which it is located. In doing so, however, the nuclei precess around this direction at a characteristic angular frequency (Larmor frequency) which is dependent on the strength of the magnetic field and on the properties of the specific nuclear species (the magnetogyric constant $\gamma$ of the nucleus). Nuclei which exhibit this phenomena are referred to herein as "spins."

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field B1) which is in the x-y plane and which is near the Larmor frequency, the net aligned moment, $M_z$, may be rotated, or "tipped", into the x-y plane to produce a net transverse magnetic moment $M_t$, which is rotating, or spinning, in the x-y plane at the Larmor frequency. The practical value of this phenomenon resides on signals which are emitted by the excited spins after the pulsed excitation signal $B_1$ is terminated. Depending upon of biologically variable parameters such as proton density, longitudinal relaxation time ("$T_1$") describing the recovery of $M_z$ along the polarizing field, and transverse relaxation time ("$T_2$") describing the decay of $M_t$ in the x-y plane, this nuclear magnetic resonance ("NMR") phenomena is exploited to obtain image contrast using different measurement sequences and by changing imaging parameters.

When utilizing NMR to produce images, a technique is employed to obtain NMR signals from specific locations in the subject. Typically, the region to be imaged (region of interest) is scanned using a sequence of NMR measurement cycles that vary according to the particular localization method being used. To perform such a scan, it is, of course, necessary to elicit NMR signals from specific locations in the subject. This is accomplished by employing magnetic fields ($G_x$, $G_y$, and $G_z$) which have the same direction as the polarizing field $B_0$, but which have a gradient along the respective x, y and z axes. By controlling the strength of these gradients during each NMR cycle, the spatial distribution of spin excitation can be controlled and the location of the resulting NMR signals can be identified. The acquisition of the NMR signals samples is referred to as sampling k-space, and a scan is completed when enough NMR cycles are performed to fully sample k-space. The resulting set of received NMR signals are digitized and processed to reconstruct the image using various reconstruction techniques.

In addition to the generation of visual images of a native region of interest, foreign substances with properties that affect the magnetic field, or the response of tissues within the scan subject to the magnetic fields and RF pulses, can also be introduced into a subject and viewed or monitored using the NMR phenomena. Examples include the use of magnetic resonance contrast agents for improving image quality of a native region of interest, and the use of such agents for determining blood flow in MR angiography. Substances that may be introduced in a subject for such purposes include gadolinium-based compounds, perfluorocarbon compounds, and iron-based or ferromagnetic compounds. One particular application of such compounds is cell tagging, a procedure in which, e.g., superparamagnetic iron-based nanoparticles are used to magnetically label cells. During an MRI scan, the regions of the scan corresponding to the presence of the nanoparticles may exhibit a darker intensity and/or greater contrast with surrounding anatomy.

The use of magnetically-relevant compounds to label or "tag" cells alone does not, however, translate to an ability of researchers to identify those cells in resulting MRI images of the scan subject region of interest with ease, simplicity, or reliable accuracy. For example, a researcher in a medical domain may be considering the use of a new cell-based therapy (CBT) as a solution to cure a myriad of diseases or conditions, and is therefore in numerous clinical trials. In CBT, a key step may be to inject/transplant stem cells into the affected joint, tissue, or organ. Unfortunately, the success of CBT in humans is currently limited. One key hurdle in the success of CBT is the inability to non-invasively, quickly, and accurately track and quantify the number and location (and thus, the migration) of transplanted cells, which may severely affect the understanding of how these cells behave after the transplant. Thus, there is a pressing need for an intelligent approach that can automatically and accurately detect these cells in MRI.

SUMMARY

The present disclosure provides systems and methods for quantifying cell numbers in MRI.

In one aspect, the present disclosure provides a system for detecting labeled substances introduced in a subject using MRI. The system may include an input that may be configured to receive imaging data obtained from a subject that has been treated with a labeled substance, via a scan of an MRI system. The system may include at least one processor that may be connected to the input and the at least one processor may be configured to segment the imaging data into MRI slices comprising pixels, subdivide at least one of the MRI slices into superpixels where each superpixel contains more than one pixel and has a size larger than an average size of a unit of the labeled substance, identify superpixels having an intensity profile corresponding to a likelihood of the presence of the unit of the labeled substance, extract candidate patches from the MRI slice based on said identification of superpixels where each candidate patch may have a pre-determined size and may be positioned within the MRI slice in association with one respective unit of the labeled substance, process the candidate patches using a machine learning (ML) module that has been trained to identify units of the labeled substance, to identify whether each candidate patch contains the one respective unit of the labeled substance where the identification of the unit of the labeled substance may be associated with corresponding pixels of the imaging data and generate a user indication of the presence of the labeled substance in the MRI slices based on such identification and association. The system may also include a display connected to the processor to display a visual representation of the user indication of the presence of the labeled substance.

In accordance with one aspect of the disclosure, a method for detecting the location and quantity of substances introduced in a subject using MRI. The method may include obtaining a quantity of a substance that comprises an MRI contrast compound, administering the substance into a region of interest of a subject, performing an imaging scan of a portion of the subject comprising the region of interest, obtaining an imaging data set from the scan, and reducing the dataset into pixel groupings based on intensity profiles where the pixel groupings may have a pixel size larger than the expected pixel size of a unit of the MRI contrast compound, filtering the pixel groupings to identify those likely to contain the unit of the MRI contrast compound, extracting candidate pixel matrices from the imaging data where each candidate pixel matrix may correspond to a pixel grouping that may be identified as likely containing a unit of the MRI contrast compound where each candidate pixel matrix may comprise a pre-determined number of pixels and is positioned within the imaging data set such that it may be oriented with respect to the unit of the MRI contrast compound, training a machine learning (ML) module by using the candidate pixel matrices and quantifying the substances of the subject by using the ML module, and displaying a visual representation of a quantity of the substances of the subject as a result of using the ML module.

The present disclosure also provides a system for characterizing MRI-labeled substances in a subject. The system may include a user input device, a display device, an MRI input configured to receive imaging data obtained from an MRI scan of a region of interest of a subject, a processor electrically connected to the user input device, the display device, and the MRI input device, the processor may be configured to: receive the imaging date from the MRI scan, label units inside the region of the interest by a user to use the display device, train a machining learning (ML) module by using the labeled units, and project a number of units for the MRI scan by using the trained ML module where the project number of units and their corresponding locations are displayed in the display device.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 shows the fundamental design phase differences among three ML paradigms.

DETAILED DESCRIPTION

Various embodiments and aspects of an MRI system that can quickly and accurately identify and track labeled compounds (whether therapeutic or diagnostic) will now be described. At an overview level, some of the embodiments described below will include an initial "training" stage, followed by an optional dynamic calibration/focusing stage for even further improving accuracy, followed by (on a subject-by subject basis) a compound administration, an image acquisition scan, an identification stage, then a user presentation stage. In the training stage, an MRI system may interact with a radiologist or other expert to collaboratively develop ground truths or learning data, and then using the same to develop a model for distinguishing and identifying units of a substance of interest. The system may then allow such radiologists, or other users, to dynamically adjust, strengthen or focus the criteria for a variety of use cases, including particular scan characteristics (e.g., main magnetic field strength, or pulse sequence type), particular organs or tissue types of interest, or even particular subjects). Additionally, in embodiments described below, the compound administered to the subject or region of interest may be therapeutic or diagnostic in nature. For example, the compound may be a solution containing cells, some or all of which were paramagnetically labeled, though other substances and labeling techniques will also work for the present systems and methods. Finally, for a particular scan or scans, systems of the embodiments described below may acquire MRI scan data from a region of interest of the subject (whether the region into which the compound was administered, a region into which the compound may flow, another region, or all of these), process the data, and present an indication to the user of either, or both, of (i) the quantity of units of the compound present in the scan region of interest and (ii) the location and/or movement of such units.

Figure 1:
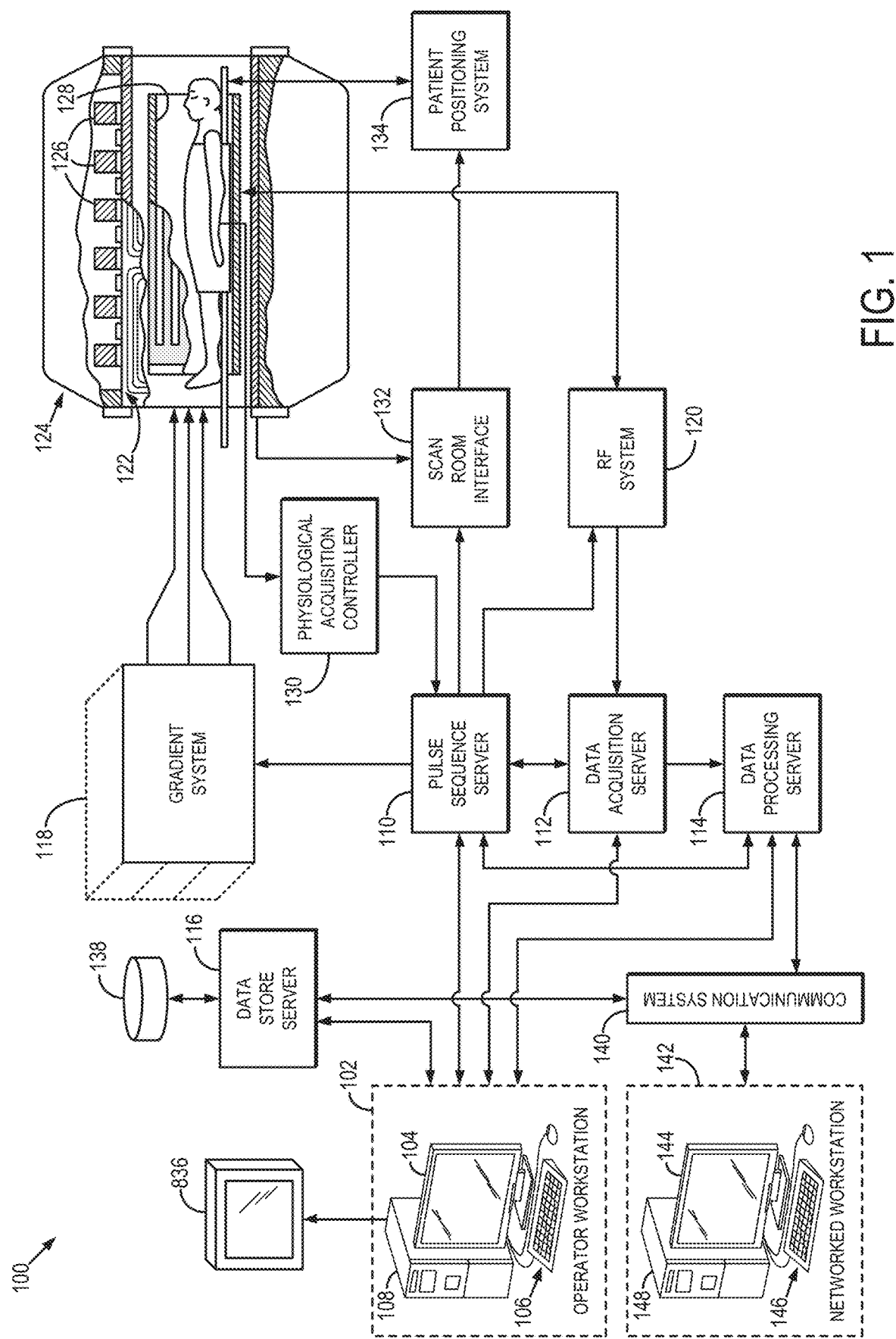
FIG. 1 is a schematic of a magnetic resonance imaging ("MRI") system for use in accordance with aspects of the present disclosure.

FIG. 1 shows an example of a magnetic resonance imaging ("MRI") system. As shown in FIG. 1, the MRI system 100 includes an operator workstation 102, which will typically include a display 104; one or more input devices 106, such as a keyboard and mouse; and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 140, which may include any suitable network connection, whether wired, wireless, or a combination of both. As an example, the communication system 140 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil (not shown in FIG. 1), are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays (not shown in FIG. 1).

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \qquad (1);$$

and the phase of the received magnetic resonance signal may also be determined according to the following relationship:

$$\varphi = \tan^{-1}\left(\frac{Q}{I}\right). \qquad (2)$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device.

Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic. In some implementations, the data processing server 114, independently or in cooperation with the networked workstations 142, may be configured to carry out steps for reconstructing high resolution imaging, and more particularly for reconstructing high resolution diffusion imaging, using low resolution imaging data, in accordance with the present disclosure.

The networked workstation 142, whether within the same facility or in a different facility as the operator workstation 102, may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

In certain embodiments disclosed herein, the networked workstation 142, the operator workstation 102, the data processing server 114, or other computer or processor linked to the same network as such components, may (i) interact with a user to calibrate the system for identification of labeled compounds administered to a subject, (ii) process the data acquired by the data acquisition server 112 for identification of such compounds for the subject of interest, and/or (iii) provide a user with the identification of such compounds.

Figure 2:
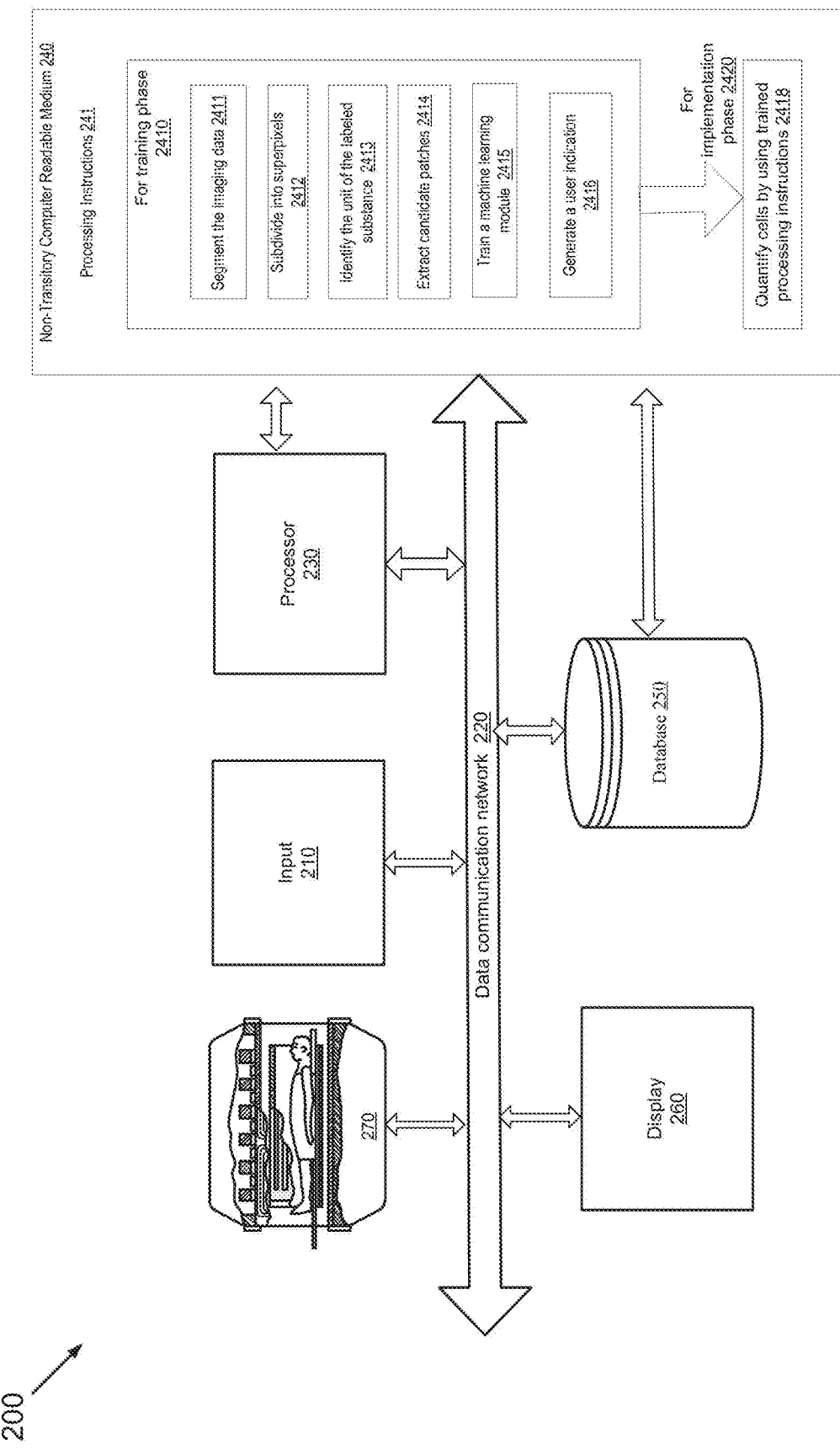
FIG. 2 illustrates one system for detecting labeled substances introduced in a subject using MRI.

FIG. 2 illustrates a system 200 for detecting labeled substances introduced in a subject using an MRI scanner 270. As shown in FIG. 2, the system may include an input 210, where the input 210 may be configured to receive imaging data obtained from a subject that has been treated with a labeled substance, via a scan of an MRI system 270. The system 200 may include a database 250 to store the received imaging data.

The system 200 may include at least one processor 230 that may be connected to the input 210 via data communication network 220. The at least one processor 230 may be further connected to non-transitory computer readable medium 240, where the non-transitory computer readable medium 240 may store processing instructions 241.

As discussed above, embodiments of such an MRI system 200 for quantifying labeled compounds are first calibrated or trained, in a phase collaboratively performed with a radiologist or other healthcare expert. The goal of the training phase is to extract a set of useful information from raw MRI image data or MRI scans and to use this information in conjunction with radiologist input for learning and codifying the discrimination of units of labeled compounds (e.g. a spot vs. a "not-spot" in what users perceive as an MRI image). The useful information extracted from radiologist input and raw data may be called features. The concept learning may be called classification.

Thus, in the training phase, the system 200 may receive raw MRI images and train the system using inputs from the experts concerning those images, to enable the system 200 to quantify, locate, and/or track cells in subsequent MRI images of the same or a different scan subject implement. The training may be performed one time. The training may also be performed multiple times, including once before the system may be placed in a production or implementation mode and additional times before or after the system has been placed in a production or implementation mode. For example, after the system 200 is initially trained (using images from a region of interest of a first scan subject, whether in vivo or in vitro), a user may decide to later further fine tune the system for a given tissue, organ, type of MRI scanner, type of labeling compound, type of subject (animal vs person, or adult vs child), or on a person-by-person basis the very individual who is going to be treated with the labeled substance. Thus, multiple iterations of the training are not needed in all instances, but may be desirable in certain circumstances where high accuracy is needed, where the surrounding tissues may be highly inhomogenous, where the signal-to-noise ratio is low, where a different magnetic field strength is to be used, or any other circumstances.

As shown in FIG. 2, for the training phase, the processing instructions 241 may be executed and may cause the processor 230 to segment 2411 the imaging data into MRI slices comprising pixels, subdivide 2412 at least one of the MRI slices into 2D superpixels or 3D supervoxels where each superpixel/supervoxel may contain more than one pixel and may have a size equal to or larger than an average size of a unit of the labeled substance, identify 2413 superpixels having an intensity profile corresponding to a likelihood of the presence of the unit of the labeled substance, extract 2414 candidate patches from the MRI slice based on said identification of superpixels where each candidate patch may have a pre-determined size and may be positioned within the MRI slice in association with one respective unit of the labeled substance, process the candidate patches using a machine learning (ML) module that may be trained 2415 to identify units of the labeled substance, to identify whether each candidate patch may contain the one respective unit of the labeled substance where the identification of the unit of the labeled substance may be associated with corresponding pixels of the imaging data and generate 2416 a user indication of the presence of the labeled substance in the MRI slices based on such identification and association.

The system 200 may be placed into a production mode after the system is initially trained. In the implementation phase, the system 200 may utilize the trained machine learning module obtained from the training phase for tracking, quantifying, and/or locating individual cells or other substances administered to a user that have been labeled using an MRI contrast agent, such as an iron-based paramagnetic compound. The system may quantify cells for raw MRI images received by using the result from executing the processing instructions for training 2410, and present the quantification to the user. As shown in FIG. 2, the processing instructions 241 may be executed and may cause the processor 230 to quantify cells by using trained processing instructions 2418. The processing instructions for quantifying cells may be for implementation phase 2420.

As shown in FIG. 2, the non-transitory computer readable medium may include processing instructions 241 for both the training stage 2410 and for implementation phase 2420. The system 200 may also include components that may be used for both the training phase and the implementation phase. For example, the system 200 may also include a display 260. The display 260 may be connected to the processor 230 via the data communication network 220 to display a visual representation of the user indication of the presence of the labeled substance.

The user indication in the system 200 may be an image showing a location and may include a quantity of detected cells. The processing instructions 241 may be executed and may further cause the processor 230 to receive a set of initial imaging data from an initial scan and output MRI images to the display without any user indication of the presence of the labeled substance. During the training stage, the system 200 may include a user input device connected to the processor to allow the user to tag depictions of the units of the labeled substances in the images. For example, the display 260 may show a radiologist or other healthcare professional a training image obtained from a training subject via MRI scanner 270. The user interface shown on display 260 may be adapted for purposes of the training phase, to permit the radiologist to zoom, scan, pan, and otherwise navigate the various slices (or 3D renderings) of MRI images, and click on or otherwise "tag" (e.g., touch, circle, etc) dark spots the radiologist recognizes as existing in that location in the image due to the presence of a paramagnetically-labeled cell. The interface may also be configured to only display to the radiologist a superpixel-reduced version of the slices or renderings of the MRI images for simplicity of review. The user input receives the radiologist's clicks and transmits them to the processor 230, which is programmed to characterize the user input or "tagging" as being a positive identification of the presence of a labeled cell at the indicated location. The processor may then extracts a patch or matrix of pixels surrounding the location the radiologist clicked on, and store that in database 250 to be used in the machine learning training.

In the training stage, the processing instructions 241 may be executed and may cause the processor 230 to use the user's tagging of the images as learning inputs to the ML module, to improve accuracy of the module's ability to identify the units of the labeled substance. The learning inputs may be ranked based on the accuracy of the module's ability to identify the units of the labeled substance. The labeling latency for the user's tagging of the images may be used to improve the accuracy of the module's ability to identify the units of the labeled substance.

In the system 200, the initial scan may be of a training subject, or of the subject to be scanned in whom the labeled substance of interest will be administered. Likewise, the initial scan may be of a different region of interest (e.g. a different organ or joint of a subject) than the region of interest of the scan subject into which the labeled substance of interest will be administered. As further described below, one important feature of the disclosed system and method which was not previously available is that, due to the synergy among, modifications of, and new developments in the various techniques employed herein, the ML module's initial training (which can be done on a wide variety of types of subjects) can be made robust-enough to operate in an implementation mode with accuracies of approximately 80-97% across different tissues, organs, joints, scan subjects, magnetic field strengths, magnetic labeling compounds, pulse sequences, weightings, and the like for subsequent scans of patients being treated.

Figure 3:
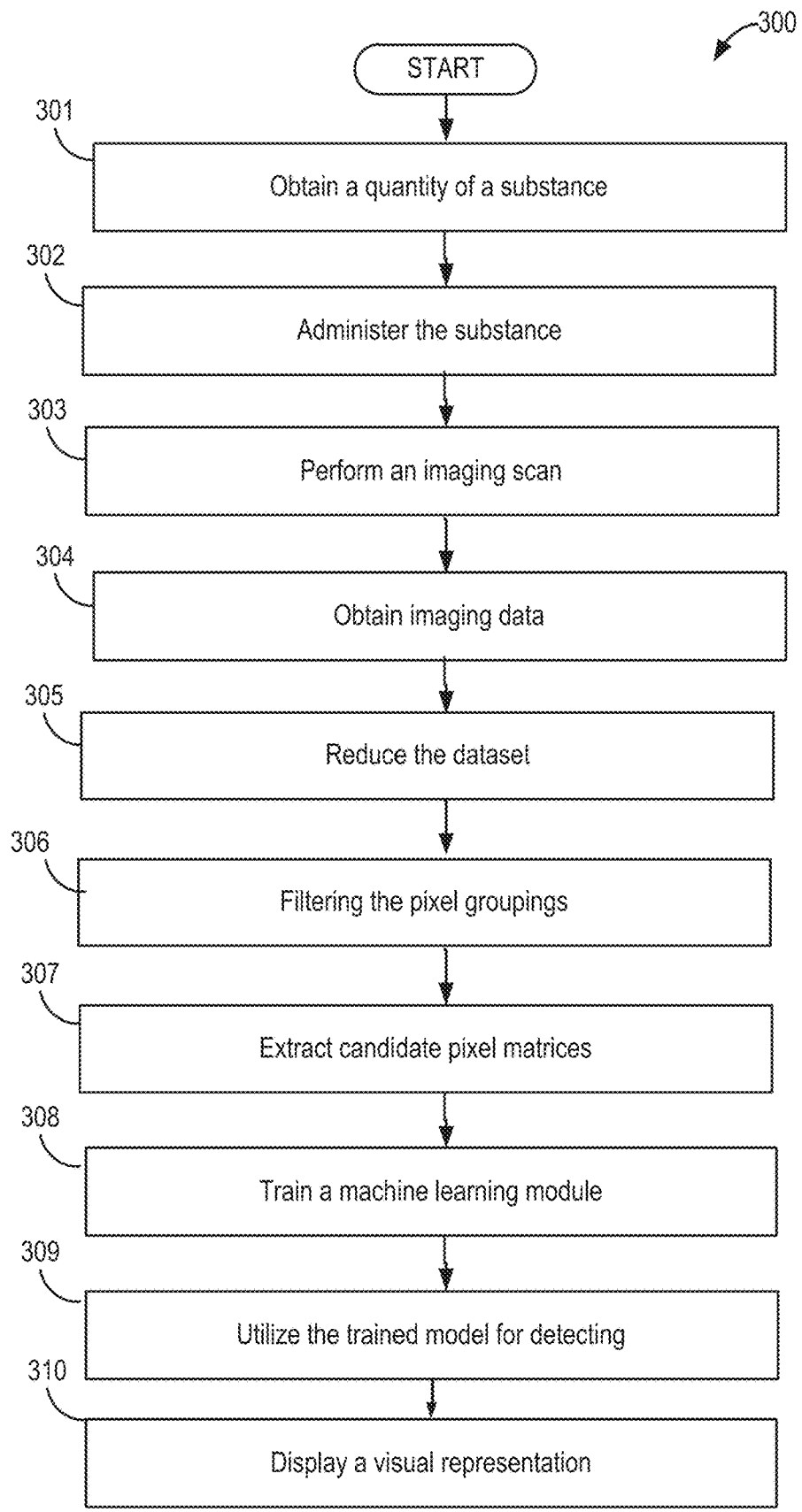
FIG. 3 shows an example logic for detecting the location and quantity of substances introduced in a subject using MRI.

FIG. 3 shows an example of a process flow overview for how the system and method disclosed herein would operate in the production or implementation mode to track, quantify, and/or locate units of a labeled substance in a scan subject using MRI 300. As shown in FIG. 3, the process 300 may begin with the step of obtaining a quantity of a substance that may comprise an MRI contrast compound 301. The systems and methods disclosed herein are useful in allowing users to accurately, track and quantify a variety of types of substances, including labeled cells or other biological substances as well as therapeutic drugs, biologics, and other compounds that may be administered to a patient (human or animal) for therapeutic or diagnostic purposes.

Additionally, to the extent these substances may not be inherently and readily distinguishable in MRI images, they may be labeled using any effective gadolinium-based, iron-based, or other paramagnetic or superparamagnetic compound that permits cell identification. In one embodiment, the system and method can be used to track stem cells that have been labeled using iron-oxide superparamagnetic nanoparticles. In another embodiment, substances that may be used to label individual cells for purposes of the systems and methods disclosed herein may comprise clinically-viable polymer-based substances used to encapsulate magnetically relevant particles. For example, Poly(lactide-co-glycolide) (PLGA) can be used to encapsulate magnetic nano and microparticles, such as iron oxide (e.g., MPIOs, or micron-sized particles of iron oxide), that provide improved contrast of individual cells in MRI image data sets. It has been determined that this encapsulated compound provides a particularly beneficial labeling agent for use with the systems and methods disclosed herein, especially in embodiments in which living cells are to be transplanted into a region of interest. These compounds are generally accepted by the body, break down into compounds that are readily dealt with by the body, and do not generally cause substantial interference with cell viability, yet deliver a increased level of the encapsulated paramagnetic or superparamagnetic substance to individual cells during phagocytosis.

The process 300 continues with the steps of administering the substance into a region of interest of a subject 302, which may include, for example, a subject's brain, liver, spinal column, joints, fluids, or other tissues and organs. Then, the process continues with performing an imaging scan of that portion of the subject comprising the region of interest 303. Alternatively, where the labeled substance administered to the subject is expected to flow or migrate to other regions, the scan may include some, all, or none of the region of interest and some, all, or none of other regions (e.g., regions into which the substance may relocate). From this scan, the process obtains an imaging data set 304, and reduces the dataset into pixel groupings based on intensity profiles 305. This reduction of the dataset may be done using, for example, a custom filtering algorithm keyed to the region of interest, administered substance, scan resolution, and/or type of labeling compound. This may also alternatively (or in combination) be done using a "superpixel" or 3D "supervoxel" process, described further below. In certain embodiments, the pixel groupings are pre-set or dynamically set scan-to-scan, for example to have a size larger than the expected pixel size of a unit of the MRI contrast compound. This serves the purpose of reducing the chance that a single unit of the administered substance, or a single unit of the labeling compound (whichever is sought to be detected) will appear in more than one pixel grouping per image slice. If a single unit appeared in more than one pixel grouping or superpixel, there would be an increased risk of inadvertently double-counting (or triple-counting, etc.) the presence of such unit at the tracking and quantification stage.

The process 300 may further include the step of filtering the pixel groupings to identify those likely to contain the unit of the MRI contrast compound 306. This may be done, for example, by selecting only those pixel groupings having an intensity profile that contains a certain degree of contrast between the darkest pixel(s) and lightest pixel(s). Other alternatives are described below. Then, the process continues with extracting candidate pixel matrices from the imaging data 307 where each candidate pixel matrix corresponds to a pixel grouping/superpixel that was identified as likely containing a unit of the MRI contrast compound. The process thus attempts to use only a matrix or patch of pixels (e.g., a 9×9, or 21×21 pixel patch) surrounding the likely "spot" in each pixel grouping/superpixel corresponding to the unit of the labeling compound, rather than the entire pixel groupings/superpixels. The patch may be positioned within the imaging data set such that it may be oriented with respect to the unit of the MRI contrast compound, or "spot," such as being centered (in a 2D or 3D manner) on the darkest patch of a pixel grouping or superpixel. This aspect of the disclosed systems and methods solves a problem that has not been previously foreseen in other attempts in the art. By substantially reducing the size of the dataset that will be used as a learning input to the ML module, but in a selective way that is keyed to the physical attributes of the substance of interest, the disclosed systems and methods achieve a potentially tremendous savings in computational time, increases in speed and accuracy of results, and open the doorway to use of far more sophisticated and discriminating identification techniques that provide far better results. While it may seem counter-intuitive to reduce a learning dataset in an application where ML is being used to discriminate and identify specific substances, it has been found that the decrease in needed computational power from reducing the input dataset to the ML algorithm (through use of the reducing, pixel grouping, filtering, and patch generation) and related benefits are substantial and outweigh the effects on the ML training process of having less input data to train the ML algorithm (effects which may be mitigated through use of several more novel techniques further described below).

The process 300 of FIG. 3 next reaches a decision point. If the user has indicated that a further calibration or fine-tuning of the ML is desired for this subject, then the scan and processing steps 301-307 will have comprised a training scan of the subject of interest. In that case, the process 300 continues with the step 308 of dynamically training the ML module by using the candidate pixel matrices via a training interface substantially similar to the initial training interface and process, as further described below. This dynamic, on-the-fly training can be made a permanent part of the ML module's training, used only for the current scan, or stored as an option to be used for future similar scans. Once that training is done, the process 300 utilizes the trained model for detecting subject of interest in any unseen/seen MRI scan and resumes with step 301, but this time treats the scan and processing steps 301-307 as imaging/tracking steps and not training steps. If the user has not indicated that further calibration or fine-tuning of the ML is desired, then the process 300 continues after step 307 with using the ML to discriminate whether the candidate patches do in fact contain "spots" indicating the presence of the magnetically labeled substance, and compiles such information into any of: (i) a quantity of units of the magnetically labeled substance in the region of interest, (ii) a quantity of units of the magnetically labeled substance not in the region of interest, (iii) based on the known quantity of units of the substance that were administered, a quantity of missing units, (iv) a graphical depiction, overlayed on an MRI image, of where each unit is located, (v) a graphical or video depiction of the movement or migration of units, e.g., based on real-time MRI, time-of-flight imaging, or other suitable method, (vi) a distribution by layer (2D, 3D, or graph) of the units within the region of interest, (viii) the absorption, congregation, or perfusion of units, and their impact on growth, preclusion, or occlusion of specific cells, tissue types, or fluids (e.g., by highlighting or annotating such tissues in an image, or presentation of the approximate change in volume, mass, or flow of such tissues), or (ix) any combination or modification of, or stat the above. At step 310, the systems and methods display a visual representation of any of such information (i)-(vi), for example a number value of the identified units of the administered substance in a region of interest, a graphical mapping of the location of the units of the administered substance, or a numerical, textual, or visual illustration of the flow or migration of such units (including, e.g., speed, spread, and direction) within the scan subject.

Figure 4:
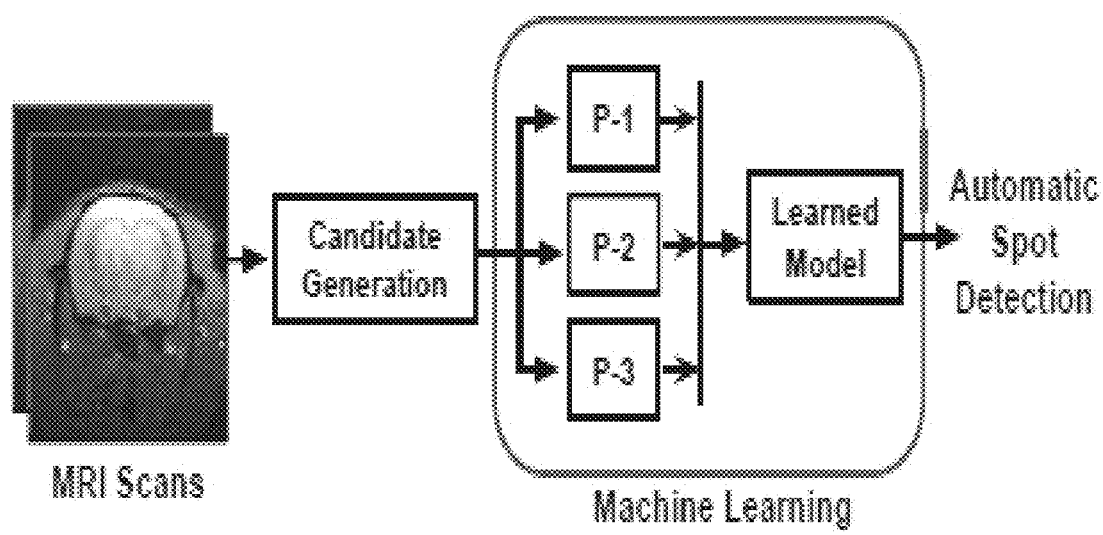
FIG. 4 shows a ML architecture with three different ML paradigms.

A more detailed discussion will now be presented concerning how the ML module of the disclosed systems and methods is developed, trained, and operates. Certain ML modules have historically required input data (also known as "ground truths") in a large scale during the training phase to ensure the resulting model will accurately discriminate as intended. This may be challenging to obtain in many MRI applications. Thus, the following description will focus on three ML paradigms that have been found by the inventors to provide unexpected usefulness, properties, and results in the disclosed systems and methods. These three paradigms are integrated with various techniques developed for further reducing the amount of input MRI training data needed, while preserving accuracy and enabling the ML module to work for a variety of scan and subject parameters beyond those of the input training data. The first two example paradigms will be discussed below with a focus on how the ML modules learn accurate models, and the third paradigm will be discussed in the context of how to modify the one of the first two paradigms so that it may perform well despite the availability of very limited input MRI training data. FIG. 4 illustrates how each of the three paradigms, P-1, P-2, and P-3, are used individually or in parallel within a generally common MRI system architecture to provide for tracking and detection of "spots," or other indications of the presence of administered compounds within the MRI images of a scan subject.

A ML approach, in the context of various systems and methods disclosed herein, may characterized by the input data fed to the ML X the features extracted from the data F and the classification model M that determines if the object of interest exists in X. In functional notation, this could be denoted as follows: $F = f_F(X)$ and $F = f_M(F)$, where $f_F$ is the feature extraction function and $f_M$ is the classification function. Typically, the functions $f_F$ and $f_M$ are learned or derived during the training stage. In some cases, a single function, $f$ where $M = f(X)$ is learned.

In order to train any ML module to differentiate and identify the content of MRI image data, example data must be provided the ML algorithm. If, however, every pixel in an MRI image (particularly high resolution images that have the power to depict the types of small structures that may be needed to visualize, e.g., a therapeutic cell treatment) were provided to the ML module, it would cost a huge computational burden and an amount of time that would make the process undesirable and in many cases unusable. Even examining small or low-resolution scans in which each pixel of the MRI images is processed by the ML algorithm in a training phase would take a very long time. In addition, such approaches may also be sensitive to noise and data variations and may not be robust and accurate.

Accordingly, a data reduction technique may be used. In one embodiment, a "superpixel" or "supervoxel" technique groups locally close pixels of an acquired MRI image with similar intensities into a single unit. Each grouping of pixels is then called a superpixel (or supervoxel). Spots in MRI images caused by the presence of administered substances (e.g., paramagnetically-labeled substances like cell treatments) will generally appear darker than the surrounding context in the images. Thus, each "spot" should be captured in a separate grouping with a much lower average intensity value in comparison to that of the surrounding superpixels. Therefore, superpixels may be used as processing units (or candidates), rather than each individual pixel of an MRI image. By sending to the ML module only those superpixels that have intensity profiles that suggest the potential likelihood of a unit of the administered substance, ML algorithms can simply learn the spot definitions in terms of superpixels' intensity differences with their surroundings. This approach significantly decreases the number of candidates to be processed by a ML approach, when compared to having a ML module process every individual pixel in an image, and hence increases efficiency and allows for more dynamic, on-the-fly training.

However, it is important to note that some superpixel algorithms may be designed for segmenting much larger objects than a spot caused by, e.g., the presence of a paramagnetically-labeled cell, which may be merely a few pixels. Therefore, when small superpixels are created in the data reduction phase, spot superpixels may also contain surrounding context pixels in many cases despite careful tuning of the algorithm. This may occur in highly heterogeneous or noisy regions of interest, and can corrupt the average intensity values of smaller superpixels and hence may directly impact the accuracy of a ML approach that learns from intensity difference-based features only.

Figure 5:
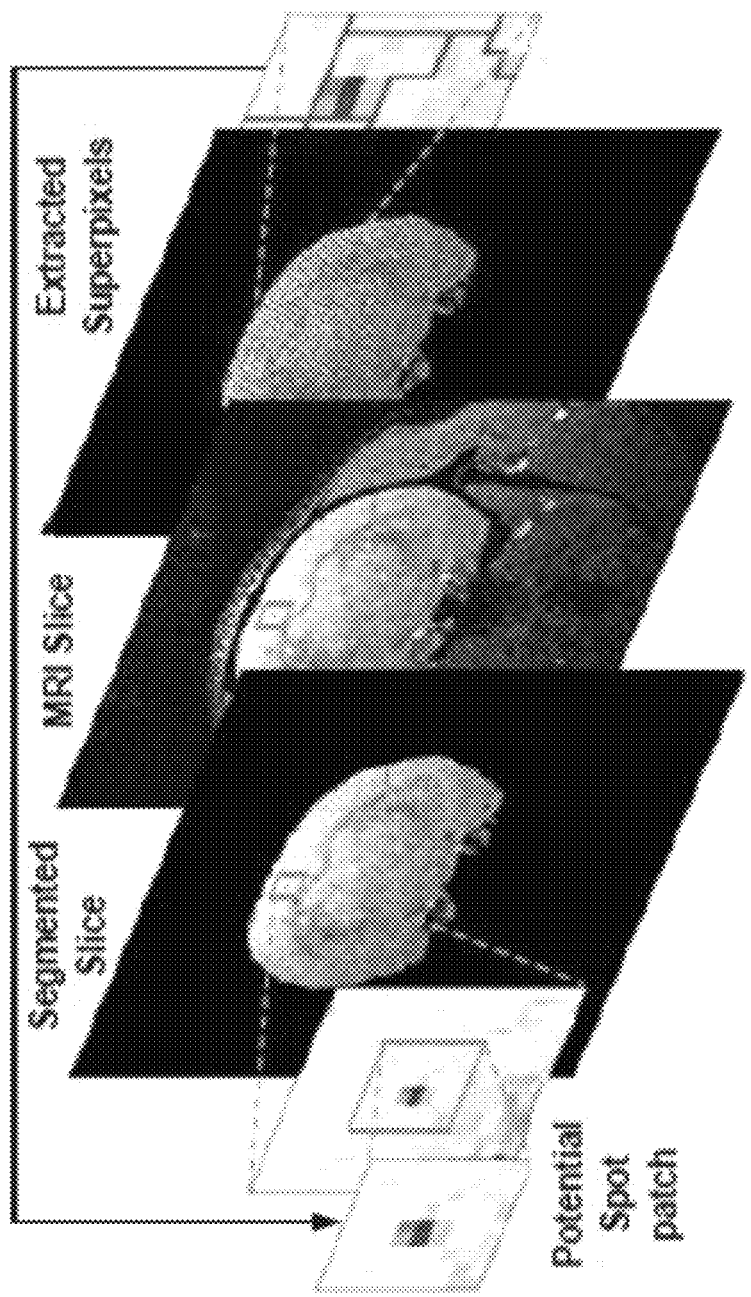
FIG. 5 illustrates the generation of a potential spot patch.
Figure 6:
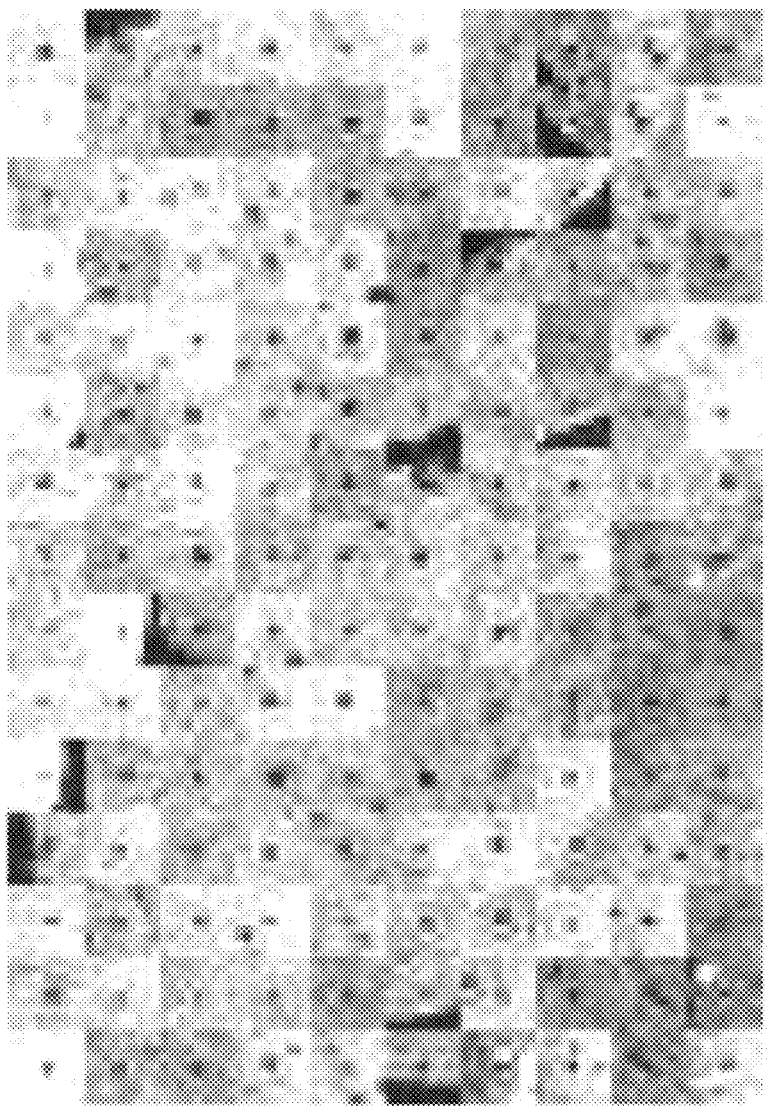
FIG. 6 shows that 9×9 patches are extracted from the MRI slice and are concatenated to make the image.

As such, a more robust candidate generation strategy may be adopted. In such approach, the pixels surrounding a potential spot can also be a part of a spot-containing superpixel or supervoxel. The approach involves capturing a matrix of pixels around the darkest pixel of every superpixel and take that patch as a potential candidate containing spot. The size of such matrices may be predetermined, and may be 2D (e.g., a patch taken from one MRI slice) or 3D. In some embodiments, a candidate patch is acquired from each superpixel that has been determined to have an intensity profile that suggests the likelihood the superpixel contains a "spot." This procedure has been shown in FIG. 5, which illustrates the relationship of a "potential spot patch" (or "candidate patch" as referenced elsewhere herein) to an MRI slice and the relationship of superpixels to an MRI slice. As depicted, the use of superpixels both (1) creates groupings of pixels based on intensity, and (2) allows for a simple algorithm to exclude regions of the image that are not relevant and/or not likely to contain the administered substance. By then also employing the novel "patch" aspect of the disclosed systems and methods after using a data reduction technique such as superpixel reduction, the potential spot patches are created from an already-reduced image dataset. FIG. 6 illustrates what a group of candidate patches might look like that are 9×9 pixels in size, each centered on the darkest pixel of a superpixel that was determined to potentially contain a "spot." As shown in FIG. 6, all the patches have a darker region in their middle representing a spot in a two dimensional MRI slice.

These candidate patches are then fed to ML algorithms, according to one of the three paradigms to be discussed below, for training purposes to learn a spot model M. Some of the candidate patches actually do contain a ground truth label, whereas others do not. In one implementation, each patch may have a label value (positive or negative), and a 2D or 3D set of pixels centered at a certain point C in a given slice k. The advantages of this approach have been determined to be: better candidate generation, the accuracy of the ML paradigms is not highly dependent on the preciseness of a superpixel algorithm, and the approach is independent of assuming any strict superpixel model for a spot in terms of its length across the number of consecutive slices.

Despite having any reasonable assumption on a superpixel model, it may not be true for all spots in the same MRI scan or in a different scan obtained with different MRI settings. Therefore, a model-free approach may be adopted to accurately detect all the spot patches in each slice and later simply join them in consecutive slices without imposing any restriction on a spot's length.

Example of Three Paradigms

Three different machine learning paradigms are explained below. The first two paradigms focus on how to accurately and automatically distinguish spot patches from non-spot patches. Then the third ML paradigm investigates what is the best approach to modify the first two paradigms to achieve better results despite using very limited training data. FIG. 7 shows certain differences among the three ML paradigms in terms of how they are trained and develop the ability to distinguish spots (or other signifiers of the presence of an administered substance of interest) in images. Below a series of experiments demonstrating how these paradigms are implemented will be discussed.

substances. Additionally, other compounds may be used to provide contrast for the units of the labeled substance, such as iron-based particles of different sizes or composition, or gadolinium-based compounds. As can be seen in Table 1 above, these scans C-E had variation in resolution, matrix sizes, and amount of spots. Set-E had 25 datasets, collected from 5 samples under 5 different MRI conditions including different echo times (TE) and noise levels as explained in Table 2. These conditions were variations in TE from 10-30 ms (signal to noise>30:1), and images with low signal to noise ratio (_~8:1) at TE=10 and 20. The effect of varying TE is to enhance the size of the spots. The higher the TE, the larger the spot. The downside of higher TE is that, due to the physics which governs enlargement of the spot, the difference in magnetic susceptibility between the location in and around the magnetic particles and the surrounding tissue, also causes the background tissue to darken. The rationale to collect images with both high and low signal to noise ratio is to test the robustness of our spot detection procedure in two potential in vivo scenarios. Additionally, for increased accuracy at the implementation/patient scan stage (after training has been completed), it may be desirable to collect and process by ML both one or more high TE scans and one or more low-TE scans, to provide the ML a greater ability to differentiate spots in a given context. For Set-E, the Total

TABLE 1

Basic details of MRI scans

| Set | Type | Subject | Labeler | Machine | Rat Names | Labels | Resolution | Size |
|---|---|---|---|---|---|---|---|---|
| Set-A | in vivo | Brain | A | 11.7T | $A_1, A_2, A_3, A_4, A_5$ | 15442 | 100 μm | 256 × 256 × 256 |
| Set-B | in vivo | Brain | B | 7T | $B_1, B_2$ | 2992 | 100 μm | 256 × 200 × 256 |
| Set-C | in vitro | Tube | B | 7T | $C_1, C_2, C_3, C_4$ | 814 | 100 μm | 128 × 80 × 80 |
| Set-D | in vitro | Tube | B | 7T | $D_1, D_2, D_3, D_4$ | 514 | 200 μm | 64 × 40 × 40 |
| Set-E | in vitro | Tube | 7 | 7T | $E_1, E_2, E_3 \ldots, E_{20}$ | 2400 | 100 μm | 100 × 64 × 64 |

As shown in Table 1, a diverse set of 33 in vitro and 7 in vivo MRI scans were utilized. The disclosed approaches all utilized an initial collection of more than 19.7 thousand ground truth labels on 15 of these scans (SetA-SetD). To obtain these ground truths, spots in each MRI slice of the SetA-SetD scans were carefully observed by a radiologist or other medical expert, who used the disclosed software "training interface" tool that allowed them to appropriately zoom-in, scan, and pan across images to find "spots." Each spatial location on which the experts "clicked" was considered a tag of that point in the image as corresponding to the presence of a spot. These clicked points are taken as the ground truth labels (i.e., positive verifications of the presence of spots) to be fed to the ML modules of each paradigm for the learning phase.

In vitro (Sets C-E): Imaging phantoms were constructed consisting of a known number of 4.5 micron diameter, magnetic microparticles with 10 pg iron per particle, suspended in agarose samples. A T2*-weighted gradient echo MRI scan was then performed on this sample using a field strength of 7 T. Each microparticle approximates a single magnetically labeled cell with appropriate iron content for MRI-based single cell detection. It is to be understood, however, that the concentration and size of microparticles can be selected to approximate the size of specific types of cells, to approximate the manner in which individual units of a substance might diffuse through a certain tissue, or to approximate the size and characteristics of other substances of interest for purposes of training a ML to identify such Labels value of 2400, as shown in Table 1, was on a per-scan basis, for each of the labeled scans $E_1$-$E_{25}$. The disclosed examples collected ground truths from experts on 7 MRI scans of Set-C and Set-D. The disclosed examples used these sets for training and evaluating ML approaches. For Set-E, only the theoretical ground truth was known.

In vivo: The disclosed examples collected two different sets of in vivo MRI scan data from two different scanners having different field strengths. Using one machine with a field strength of 11.7 T, 5 MRI scans of rats were collected, which are represented by set-A in Table 1. Three of them were injected intracardiac with Micron-sized paramagnetic iron oxide (MPIO)-labeled mesenchymal stem cells (MSCs), at a level of ~10 pm iron per cell. This transplantation resulted in delivering cells to the brain, whereas two rats were naive. Alternatively, an intraventricular injection would deliver cells only to the liver and lungs. Using another machine with 7 T, 2 more brain MRI scans of rats were collected, both containing labeled MSCs. Set-B represents these 2 scans in Table 1. The motive behind collecting two different sets was to be able to test the generalization and robustness of the disclosed learned algorithm towards data variations. Note that the disclosed approach injected different amount of MSCs in different rats to achieve further variations in data.

Paradigm-1 (P-1).

This paradigm first converts each candidate patch image into a set of useful values that can accurately describe characteristics of the entities in the image. This can be done using, for example, hand-crafted feature extraction strategies. Some examples include linear binary patterns, Histogram of oriented gradients, SIFT etc. These extracted values (also known as features), rather than the raw patch images, are then taken as the inputs by a ML algorithm for its training. Generally speaking, the preliminary step of extracting features from images is designed by experts based on their intuition and studies. In other words, the function $f_F$ is essentially fixed in advance, based on expert intuition and problem understanding. Likewise, the function $f_M$ may also be predefined. However, using the input data the parameters of the function $f_M$ are tuned to maximize the accuracy of model M on training data.

A set of useful features may be extracted that can comprehensively capture information, about the entities in the candidate patch, pertaining to their following aspects: (1) texture, (2) shape and intensity, and (3) context tissue appearance. The features may generate a long feature descriptor for each candidate patch. Usually, in long feature vectors, some features may be irrelevant or redundant. The most useful features are selected and the irrelevant ones may be eliminated by using a feature selection module that may employ correlation-based feature selection algorithms. Finally a subset of the features for all the candidate patches, along with their corresponding labels may be fed to a classification algorithm that may explore patterns in the feature values to learn spot definitions. Based on this definition, a learning algorithm then classifies each patch as a spot patch or non-spot patch.

A diverse group of classification techniques may be used. The techniques may include probabilistic (Naive bayes), functional (Multi-layer perceptron (MLP)), and decision tree (Random Forest) approaches. The computer vision techniques may be introduced for capturing features for shape, context and texture of entities in the candidate patches.

Figure 8:
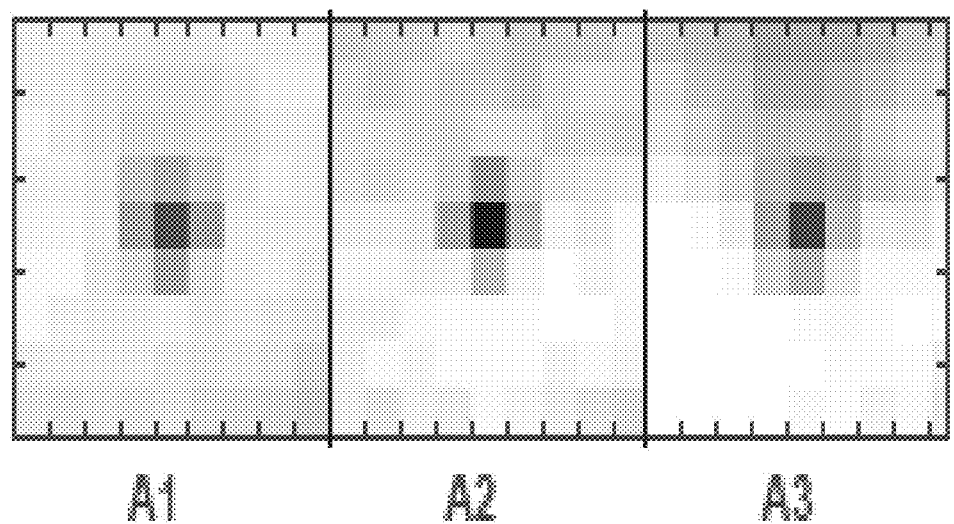
FIG. 8 shows the top PCA component by using 9×9 for the spot patches obtained on the three labeled rats.
Figure 9:
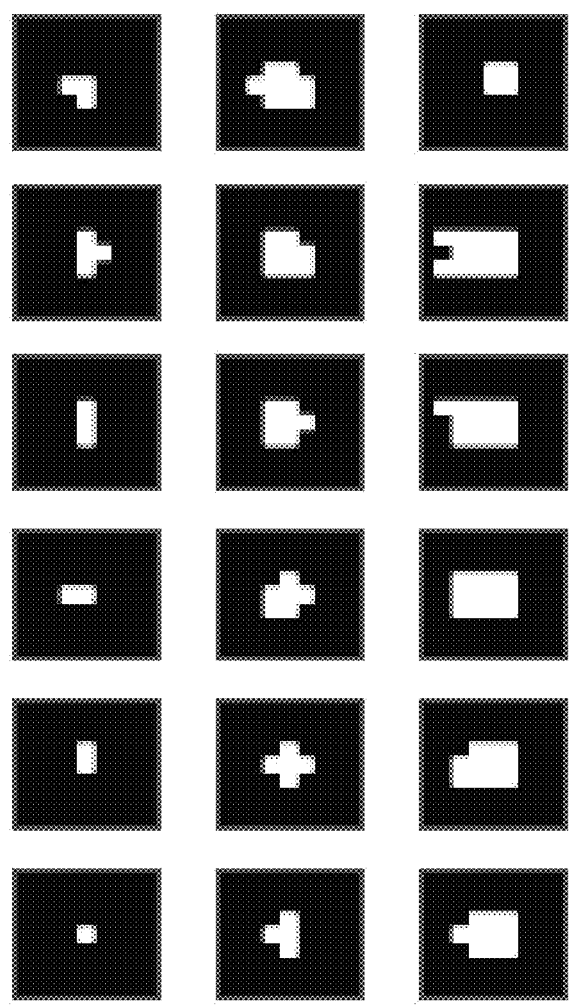
FIG. 9 illustrates shape filters.

Shape and Intensity:

Using the concept of Eigen faces, Principal Component Analysis (PCA) spot shapes may be extracted by using all the spot patches in the training set. In FIG. 8, the top PCA component is shown by using a 9×9 matrix for the spot patches obtained on the three labeled rats of Set-A. Later, by applying a threshold-based strategy on the values of top PCA components, different binary shapes may be extracted and may be used as filter patches. Some of these shape filters are shown in FIG. 9. All these patches are rotated and translated to obtain more diversity in shape filters. These filters are convolved with each candidate patch to extract its shape information that can be used as a feature. Note that, convolution of these shape filters also considers intensity difference between group of subject pixels with its surrounding.

Figure 10:
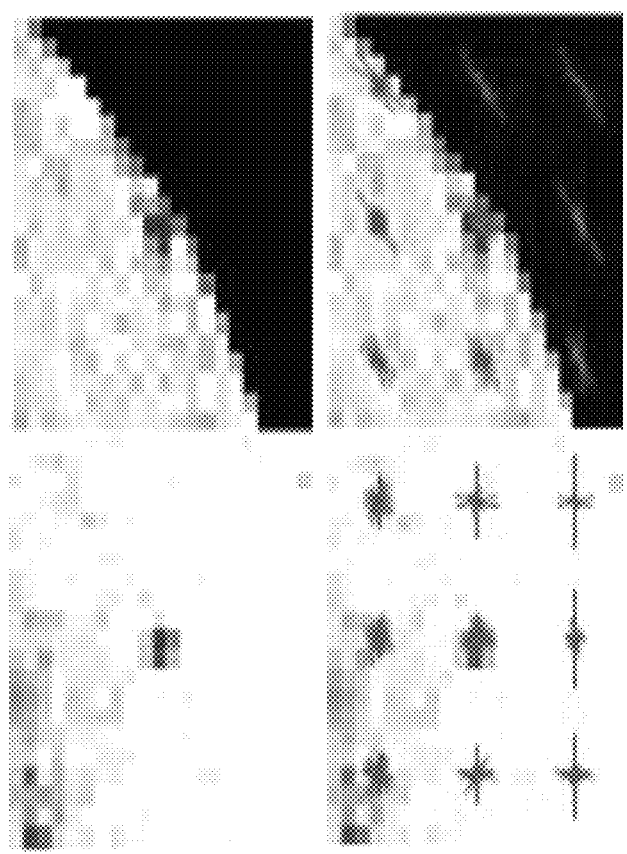
FIG. 10 shows visualization of HoG features on two context patches.

Context Tissue Appearance:

While learning the definition of a spot, it may also be useful for a classifier to learn about its surrounding context. For example, in a very noisy local context, it may not be a good choice to relate every group of dark pixels to a spot. Therefore, to capture the appearance of patch's context, a larger patch of 21×21 may be extracted around the center of a candidate patch. Two appearance descriptors may be used to extract features: (a) Histogram of Gradients (HoG), and (b) Gist. Visualization of HoG features on two context patches is shown in FIG. 10. As shown in FIG. 10, different red lines indicate the different directions of intensity gradients in a local area, whereas the length of the lines determine their magnitude. This information on local gradients is utilized to capture appearance of a given image.

Texture:

To get an idea of the candidate patch's texture, the patch's entropy and variance may be computed. Further, each patch may be binarized to generate small blobs. The number of blobs and area of each may be used as additional features.

Paradigm-2 (P-2)

This approach has shown an enormous success by performing better than other methods in a number applications. Specifically, deep convolutional neural networks (CNNs) have been found to be particularly useful. This algorithm can directly take the candidate patches as an input (i.e., in their image form, as opposed to extracted features), relate the values at different pixel locations in a patch to automatically learn complex hidden features in multiple layers, and perform classification.

Figure 11:
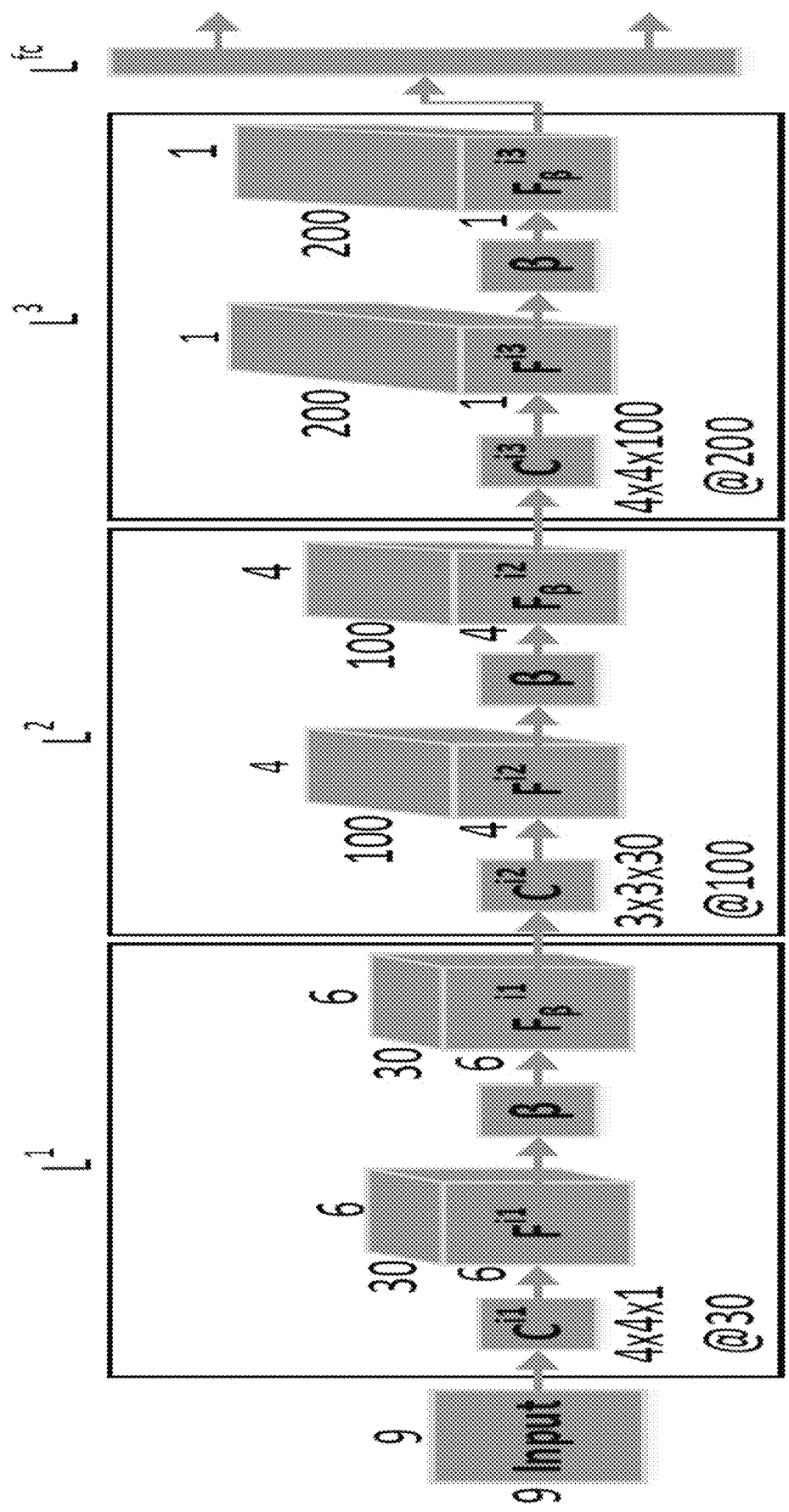
FIG. 11 shows Deep-CNN architecture has three composite layers followed by fully connected layer for classification.

Unlike paradigm-1, these automatically-learned hidden features are hierarchically learned in multiple layers in an automatic fashion and not hand-crafted by experts. In other words, thought of from a functional standpoint, $f(X)$ is learned automatically from training data X without designing any hand-crafted features (such as would be done in paradigm-1). Features extraction and classification functions are learned together in a unified framework. However, unlike paradigm-1, approaches in paradigm-2 require a comparatively larger amount of data for reliably learning $f(X)$ It should be noted that paradigm-3 represents a new way to overcome such limitation of paradigm-2. At the training stage, the ML algorithms of paradigm-2 can directly take candidate patches as an input, relate the values at different pixel locations in a patch to automatically learn complex hidden features and perform classification. In paradigm-2, The proposed CNN architecture has three composite layers followed by a fully connected layer for classification FIG. 11 shows the CNN architecture used in this work. The network takes a 9×9 image patch as input for a classification task i. Each composite layer $L^k$, $k \in \{1,2,3\}$, is composed of a convolutional layer $C^{ik}$ which produces the feature maps $F^{ik}$ and a non-linear gating function β producing the transformed feature maps $F_\beta^{ik}$. After passing through the composite layers, the net passes through the fully connected layer $L^{fc}$ which produces the output. The softmax function is then applied to the output.

A composite layer may comprise a convolutional layer, a pooling layer and a ReLU (Rectified Linear Unit) layer.

Figure 12:
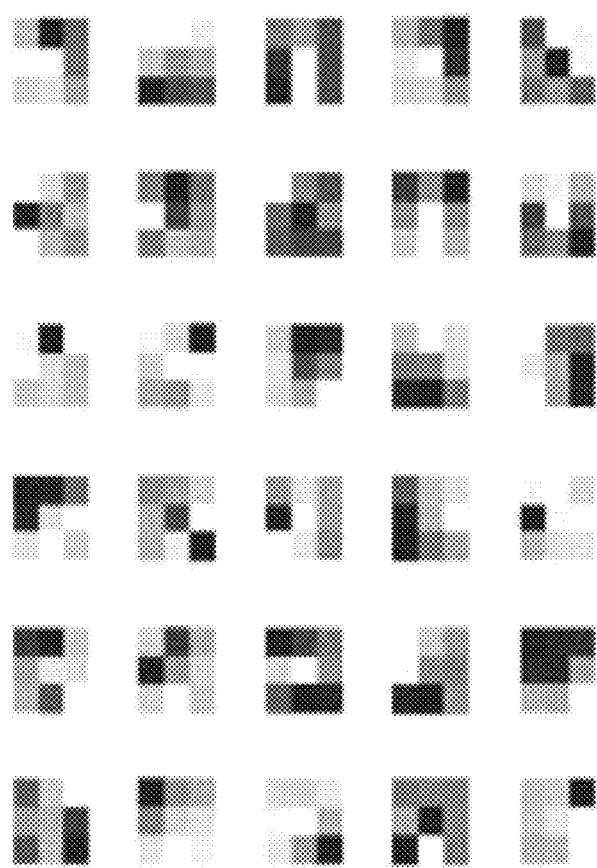
FIG. 12 shows the weights of some convolutional filters learned by the second layer of the Deep-CNN.

Convolutional Layer:

As shown in FIG. 11, each composite layer may have a convolutional layer. The convolutional layer may take an image as an input and convolve a specific filter of a given size. The result is called a feature map. q convolutional filters will result in q feature maps. The feature maps may be modified by the pooling and ReLU layers without changing their dimensionality. In the proposed architecture, only the use of non-linear gating layer (ReLU) is shown along with convolutional layers. Finally these modified feature maps from one composite layer are taken as input by the convolutional layer of the following composite layer. The CNN 'learns' a large set of these filters for the convolutional layers such as to produce a superior accuracy. In FIG. 12, the weights of some convolutional filters learned by the second layer of the Deep-CNN are shown.

Pooling Layer:

The Pooling layer may be used to down sample the input image and achieve translation invariance. Since the patches are already small-sized, therefore, pooling layers may not be used in this disclosed architecture.

Non-Linear Activation:

The ReLU layer may be used to add nonlinearity to the CNN architecture. In one embodiment, a ReLU layer does not change the dimensionality of the feature map. However, it changes all the negative values in a feature map to zero.

Experimental Comparison of the First Two Paradigms (1) In Vivo Evaluation Studies The spot classification performance of a diverse set of approaches may be evaluated by using the two sets of in vivo MRI scans, for example: set-A and set-B. The experiments and results for set-A that has 5 different MRI scans, all obtained from a single MRI machine and were labeled by one expert. Three of these scans contain spots that were labeled by experts whereas the remaining two were naive. Six combinations of testing and training pairs are made such that there are two scans in the testing set where one of these is a naive scan.

Figure 15:
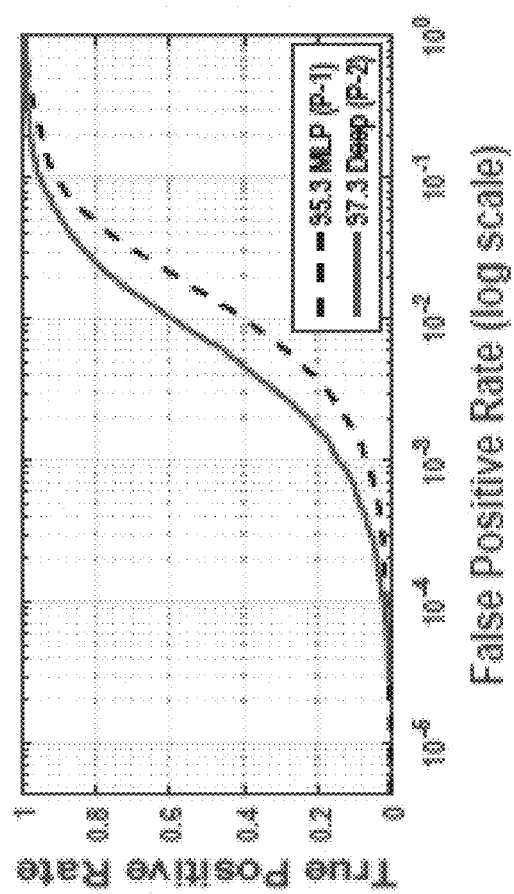
FIG. 15 shows the ROC curves.

The remaining three scans, in each pair, are used for training the ML algorithms. Area Under the Curve (AUC) is used as a standard measure for classification accuracy and tabulate experimental results for all the algorithms in Table 2.

achieved 95.3%. The ROC curves for this test are shown in FIG. 15. However, it is to be understood that the MLP approach (and other approaches under paradigm-1) may under certain circumstances perform with higher accuracy, and may be more desirable.

Figure 17:
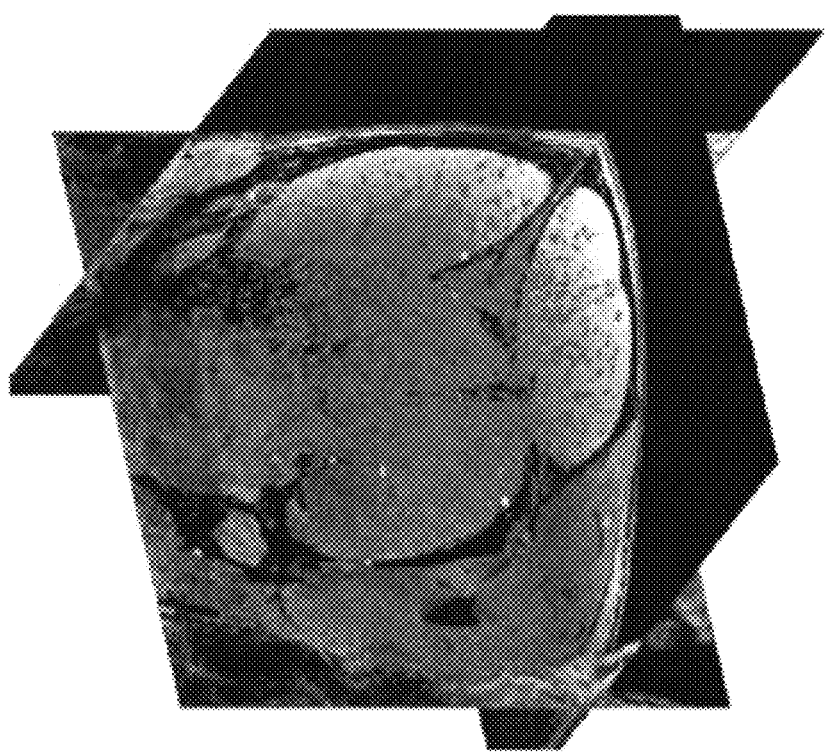
FIG. 17 shows the detected spots that are displayed in the one 3D brain MRI image.

In FIG. 17, the detected spots are displayed in the one 3D brain MRI image that was obtained from a 7 T set. The success of CNN over all the approaches in paradigm-1 clearly demonstrates that there is a significant amount of discriminating information in patches that may not always be exploited by the approaches in paradigm-1. It also shows that the features automatically learned by a machine learning module are superior to the hand-crafted features designed by experts.

(2) In Vitro Evaluation Studies

Deep-CNNs were also seen to provide the best result when used on the in-vivo datasets, despite the comparative simplicity of its approach. In one of the example studies, its performance was evaluated on in vitro data from set-B and

TABLE 2

Results and comparison of in vivo spot detection performance using paradigm-1 and paradigm-2.

|       | Algorithms | $J_1$ | $J_2$ | $J_3$ | $J_4$ | $J_5$ | $J_6$ | means |
|-------|------------|-------|-------|-------|-------|-------|-------|-------|
| P-1   | Multi-Layer Perceptron | 93.9 | 89.4 | 95.8 | 95.4 | 90.0 | 95.7 | 93.4 ± 2.9 |
|       | Random Forest | 94.0 | 86.9 | 95.3 | 94.1 | 86.0 | 94.7 | 91.8 ± 4.2 |
|       | Nave Bayes | 82.9 | 81.8 | 84.3 | 84.1 | 80.1 | 83.7 | 82.8 ± 1.6 |
| P-2   | Deep CNN | 96.4 | 92.3 | 96.1 | 96.4 | 91.2 | 95.0 | 94.6 ± 2.3 |
|       | Multi-Layer Perceptron | 91.1 | 85.2 | 90.9 | 91.4 | 84.2 | 90.3 | 88.9 ± 3.3 |
| means |            | 91.7 ± 5.2 | 87.1 ± 4.0 | 92.5 ± 5.0 | 92.3 ± 4.9 | 86.3 ± 4.5 | 91.9 ± 5.0 |  |

By observation, the best results among the disclosed examples were achieved by a deep convolutional neural network (CNN) with a mean accuracy of 94.6%. The second best results were observed for multi-layer perceptron (MLP) which utilizes a traditional framework of neural networks. MLP achieves its best result while using feature values extracted for paradigm-1 approaches. However, like CNNs, this approach is also based on neural networks and learn further high level features on top of the hand-crafted features.

Figure 13:
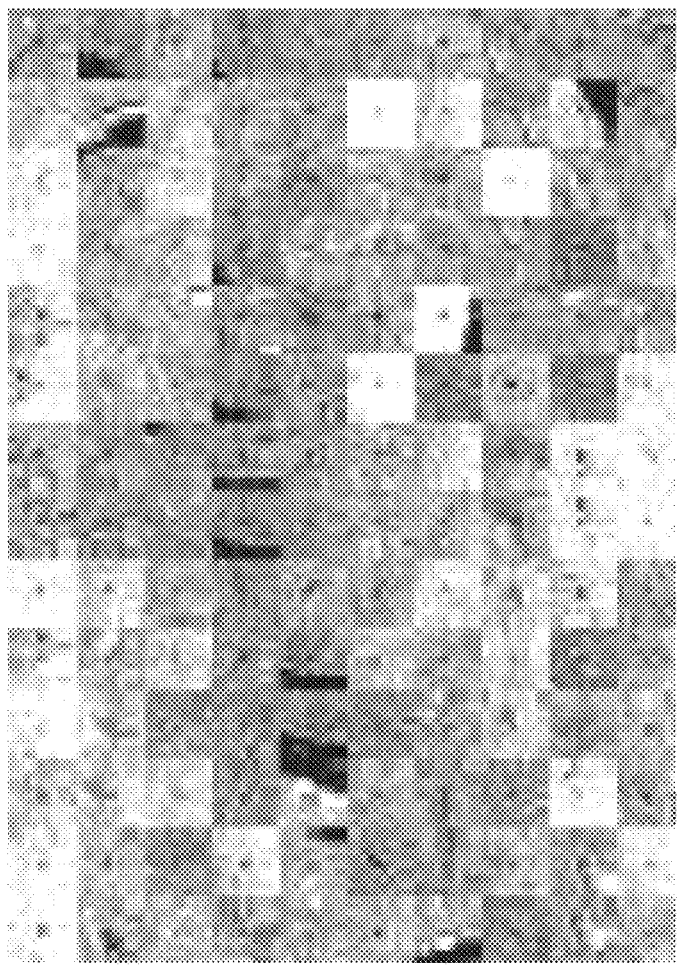
FIG. 13 shows the labeled patches.

Probabilistic Naive bayes, using paradigm-1, showed the worst detection performance with an average accuracy of 82.8%. This can be because naive bayes assumes complete independence between the features which in many practical problems is not true. Further, J2 and J5 testing sets may be proved to be most challenging with low mean accuracies of 87.1% and 86.3% respectively from all algorithms. Whereas the dataset J4 gave the overall best performance with mean accuracy of 92.5%. To investigate this, both J2 and J5 were found to contain MRI scan $A_1$ in their test set accompanied with a different naive Rat scan. The labeled patches can be seen in $A_1$ are significantly more challenging (see FIG. 13.) than that in the other scans (see FIG. 6).

Now, the best two approaches are evaluated by using the other in vivo scan i.e set-C. This data was collected from a different machine having a different field strength and was also labeled by a different expert. In this study, all the previous five scans of set-A were used for training, creating a large training set, and then testing the learned spot detection models on the in vivo scans in set-C.

Figure 14:
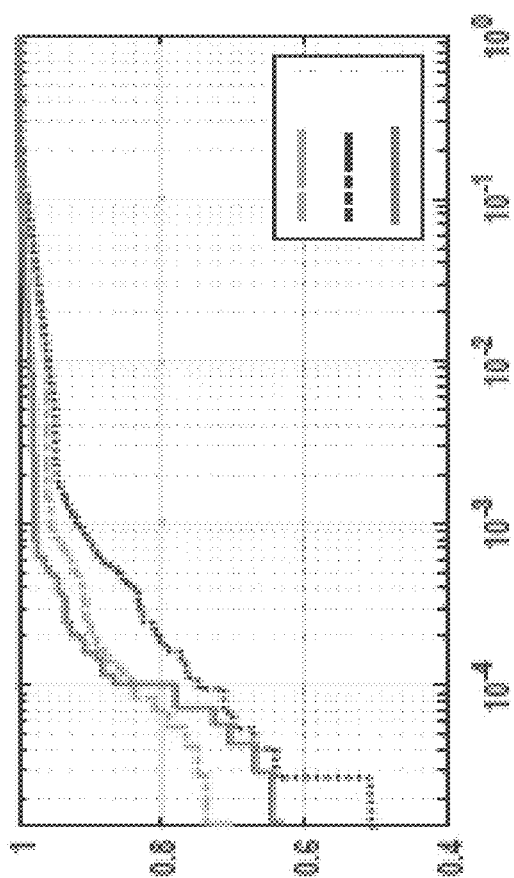
FIG. 14 shows the individual ROC plots.

Despite the differences in machine, magnetic field strength, and also the identity of the labeling expert that "tagged" spots representing the labeled MSCs, Deep-CNN performed best with an accuracy of 97.3% whereas MLP set-D. Its performance was tested on set-B, which has 4 in vitro MRI scans, with a 100 μm resolution creating an MRI cube of (128×80×80). Using these four scans of set-B, three different testing and training pairs were developed. Each testing and training set had two MRI scans. The naive MRI scan was always kept in the testing, making three combinations with the remaining other sets. The CNN performed with a mean accuracy of 99.6% on these in vitro scans. The individual ROC plots for these tests are shown in FIG. 14.

An additional experiment was conducted to observe the extent to which this performance would degrade if four in vitro scans were obtained with a much lower resolution of of 200 μm creating an MRI cube of (64×40×40). Such a scan would be desirable for some practical applications, including that it may be more convenient in some circumstances (e.g., when imaging children) to quickly perform an MRI scan with a lower resolution. Thus, using the same procedure, three different testing and training pairs were created.

Figure 16:
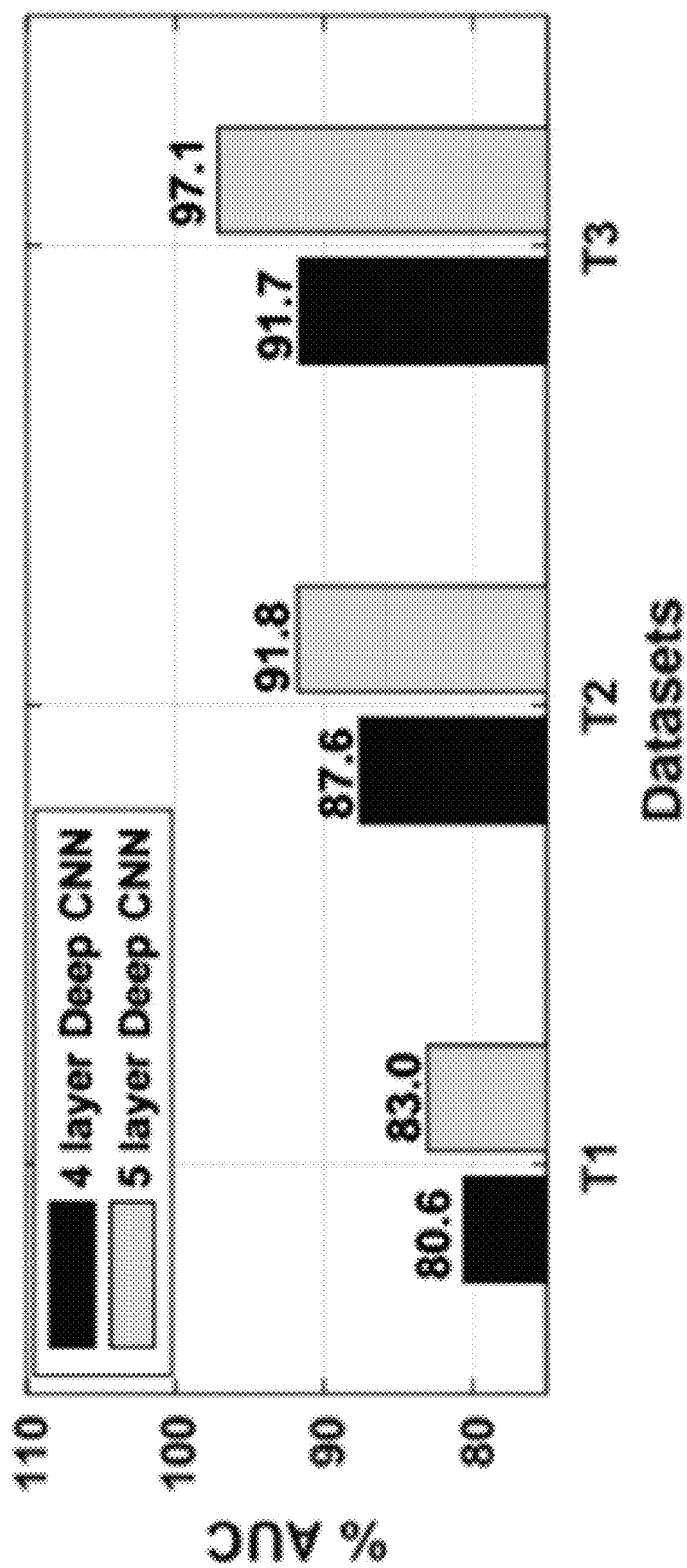
FIG. 16 shows the individual improvements on all the three sets.

It was observed that the mean performance decreased to 86.6%±5.6%. However, when the number of learning convolutional layers was increased for CNN, the performance improved to 90.6%±7.1%. The individual improvements on all three sets are shown in FIG. 16.

In practice, in vivo scans might be performed with different MRI machines at different laboratories using different field strengths, but with a desire to use the same trained ML module (e.g., if the module were trained by the MRI scanners' manufacturer). Accordingly it was important to demonstrate the robust nature of the learning paradigms discussed above. The in vivo studies, as shown in FIGS. 14-16, demonstrated that the approaches disclosed herein show robustness to such variations and achieved 97.3% accuracy despite such differences.

Similarly, an experiment was conducted to determine how performance would be affected for an in vitro imaging scan, using an ML module to detect an administered substance that had been trained to identify the substance using in vivo data. Therefore, an experiment was conducted in which a ML model was trained using set-A (in vivo) and then tested for accuracy using set-C (in vitro). The CNN ML paradigm performed with an accuracy of 96.1%.

Figure 18:
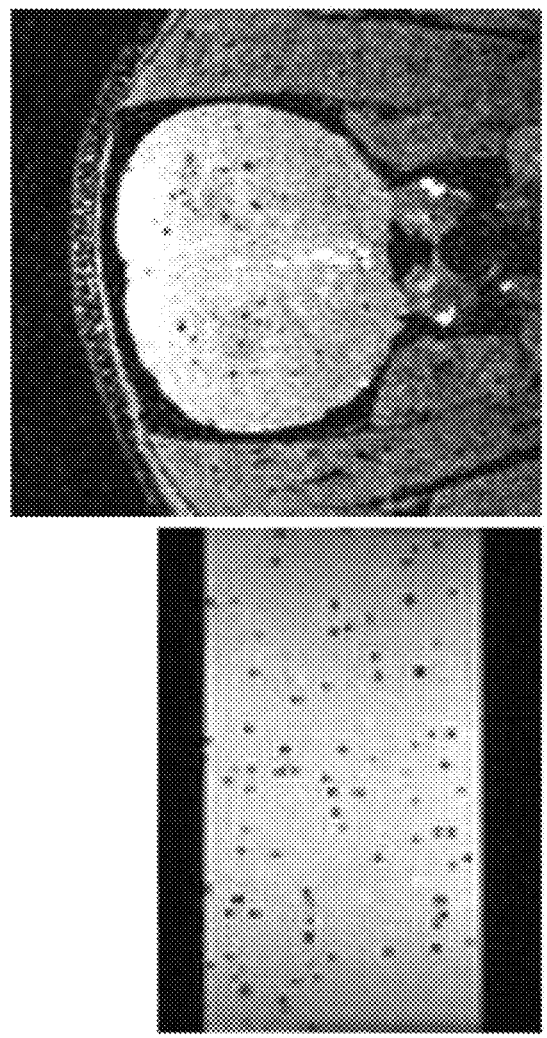
FIG. 18 shows an in vivo and in vitro MRI slice with automatically detected spots.

In another experiment, all the data from set-A to set-D was used for training a ML algorithm, and then its performance/accuracy was evaluated on set-E (a diverse set of 25 in vitro MRI scans of tubes). The results are tabulated in Table. 3. An in vivo and in vitro MRI slice with automatically detected spots is shown in FIG. 18, where the left image is taken from an in vitro intro slice and the right image is an in vivo slice.

TABLE 3

Automatically detected number of spots in 5 samples under 5 conditions.

|   | Tube 1 | Tube 2 | Tube 3 | Tube 4 | Tube 5 |
|---|--------|--------|--------|--------|--------|
| A | 2147   | 2272   | 2474   | 2152   | 2270   |
| B | 2608   | 2750   | 3039   | 2644   | 2660   |
| C | 2844   | 2993   | 3272   | 2809   | 2909   |
| D | 1982   | 2023   | 2247   | 1949   | 2014   |
| E | 2419   | 2563   | 2794   | 2401   | 2445   |

A: TE 10,
B: TE 20,
C: TE 30,
D: TE 10 (Low SNR),
E: TE 20 (Low SNR).
The actual injected number of spots is about 2400 in each tube.

Paradigm-3 (P-3)

Both the above two paradigms of machine learning may be reliant on using a fairly large set of example/training data for accuracy, in some circumstances—even when taking into account the dataset reduction achieved through use of the superpixel and candidate patch techniques. However, actually collecting a large-enough set of data in a clinical setting (or other setting in which training data, as opposed to patient scan data, is acquired) is generally a challenge, and can require repetitious effort and monopolize MRI scanner time. Therefore, the inventors explored further how their deep learning approach could show success despite using very limited training data.

For this purpose, a third paradigm of ML was explored that is called transfer learning. Transfer learning assumes that the available data for training a ML approach is of two types: (i) target data: this is the data of the task at hand, for example, the MRI data and detecting spots in MRI is the target task; and (ii) source data: any other image datasets, such as images available on the internet can be source data. For example, images of cats, stars, soccer balls and other somewhat randomized images can be used as source data. The follow discussion will demonstrate how a ML algorithm, and more specifically a CNN, can use a transfer learning paradigm to accurately detect spots in MRI with limited data.

An approach is described herein that can first select an appropriate source and then use information from that source to improve the accuracy of the spot detection task, when used in the implementation phase of the systems and methods disclosed herein. The experimental results show that even using 5% of a training dataset, the performance of a ML algorithm may be improved from about 53% to 78%. For example, on average, there are about 100,000 patches that comprise a training set obtained from one MRI scan, and about 5000 out of these may represent spots and may be labeled by an expert manually. As such, 5% of the total are randomly picked for training a CNN. According the accuracies obtained on the example test set, the accuracy improves from 53% to 78%. The architecture of this approach is shown in FIG. 16.

The approach is illustrated as follows:

(1) First, similar to the second paradigm, candidate patches are generated.

(2) Image data from a source domain is transformed to the candidate patch size and converted to grey scale. Since candidate patches have two classes (i.e. spot patches and non-spot patches), a common set of random and background images is added to each source's data, making it a two class dataset.

(3) Deep convolutional neural network (CNN) is then trained using each two class dataset, including the target data of spot detection. The CNN training may be performed in a variety of methods, with a goal of optimization and removal of bias. To remove any bias of code, CNN training may be performed using, for example, a standard "MatConvNet" implementation, or variation thereof. Details of the proposed CNN architecture, in terms of filter sizes, feature maps and number of layers are summarized in FIG. 11. The training epochs for the proposed CNN ranged from 10 to 12 in the experiments described herein, depending on the validation error during the training phase. Other parameters were used in the standard manner as provided by the MatConvNet implementation.

(4) The algorithm then transfers the learned information from source domains to the target domain by transferring the weights of convolutional layers (learned features on source data). Note that based the following two criteria, the algorithm transfers knowledge from only the top-h: (a) How well the CNN, learned on source predicts, spots in unseen target data?, and (b) How different are the source features from what the ML algorithm has already learned based on the target training dataset? These two criteria are quantitatively measured for each convolutional layer, and the bigger their values, the more beneficial the source dataset (and resulting convolutional layers) is for transfer learning.

(5) Then the top-h (e.g top 3) source CNNs are evolved by continuing their further training on target data (spot and non-spot patches). This creates h CNNs at the end, each of which is capable of detecting spots in an unseen MRI.

(6) The decision of each CNN is weighted and is combined in a probabilistic manner to generate the final decision.

Experiments with Paradigm-3.

In the experiments performed using paradigm-3, the goal was finding answers to two questions: (1) How does the approach perform when the training data is very limited and how does that compare to when the training data is sufficiently large? (2) How well does the approach rank the sources? (In other words, what is the difference in the performance between the best and worst source ranked by the approach?)

Figure 19:
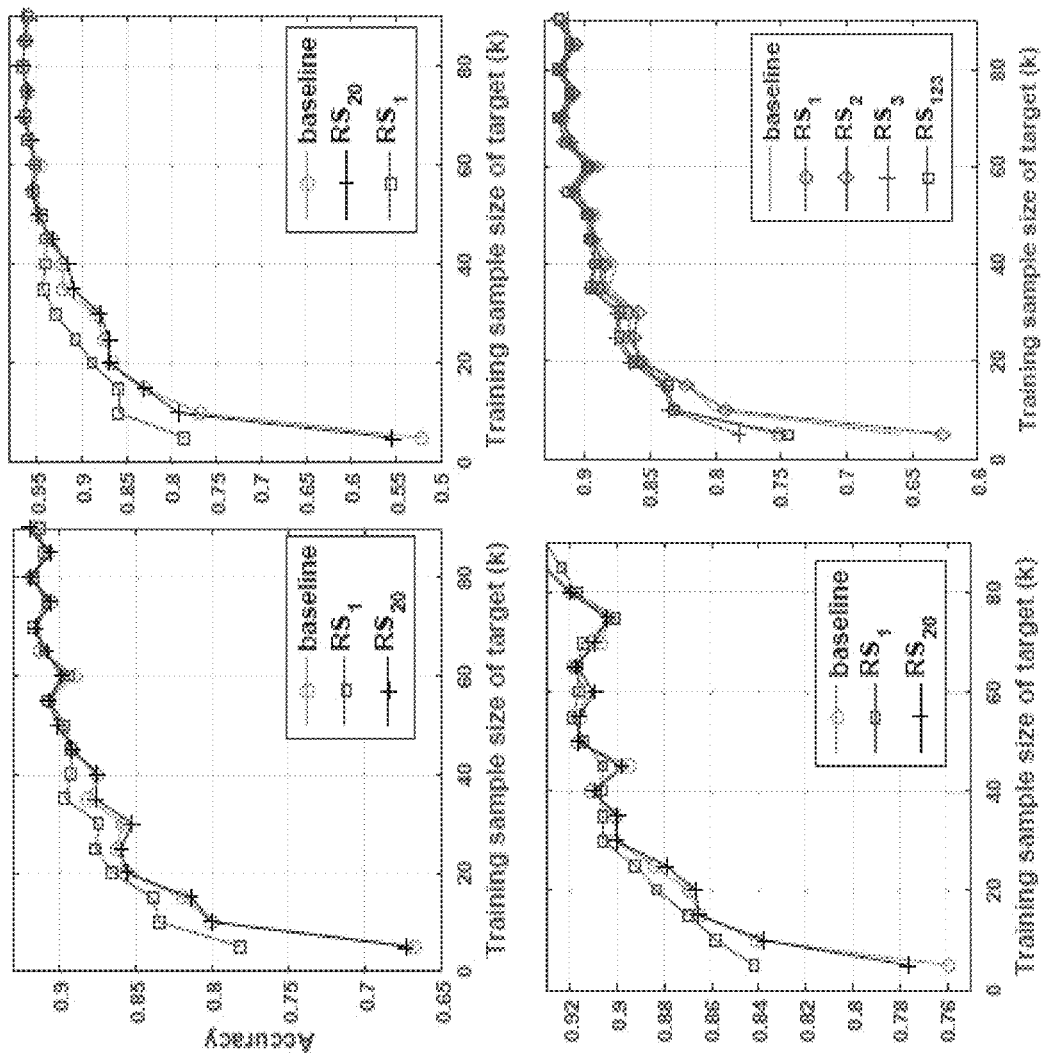
FIG. 19 shows three different testing scenarios based on three labeled datasets.

In FIG. 19, based on three labeled datasets, three different testing scenarios are shown. On the x-axis, the amount of training data and are changed. On y-axis, the performance of differently trained CNNs is observed. The baseline is a CNN that did not undergo any transfer learning, and only used the target data for training. Whereas the remaining two represent CNNs that went through transfer learning with a best ranked and worst ranked source respectively.

The performance gain can be seen due to transfer learning from the best source is significantly higher when the training data is limited. With small datasets, a traditional CNN approach may overfit, resulting in poor performance on testing data. However, transfer learning provides generalization to the CNN, avoiding over-fitting. Further, choosing a group of top-h can be shown to be useful than simply choosing one. Using multiple perspectives of different CNNs can add robustness to any mistake in ranking of the approach.

It can be observed that in one scenario, the approach mistakenly ranked one source as the second best as shown in bottom right figure of FIG. 19. However, it can be seen that due to decision weighting of multiple sources, a performance can be achieved that is significantly better than the worst source at limited data. In fact, in many cases, it can be seen that it provides better results than the other two sources as well.

Accordingly, it has been determined that the success of traditional CNNs, in the context of tracking administered substances using MRI, rely on large scale labeled datasets. However, in the problem of tracking such substances (e.g., identifying spots corresponding to a paramagnetically labeled cell or compound), one MRI scan may only contain a relatively small quantity of the administered substance (e.g., a small number of transplanted cells) and hence the labeled datasets cannot provide large scale spot samples for sufficiently training a traditional CNN. Further, due to the high appearance variation of spots across MRI scans and within MRI scans, this limitation on the size of the training data available from one MRI scan can affect the robustness and general feature representation modeling of MRI spots in CNN training.

Therefore, in order to learn improved and more accurate spot feature representations from limited spot samples in MRI, various approaches may be explored to better utilize the source data in the transfer learning by using CNNs.

Example of Automatic Source Selection

Transfer learning improves the performance on a given task such as spot detection by importing and exploiting additional information from other tasks that may not be directly related to the given task (such as spot classification). The given task, which in one disclosed case is the detection of injected cells via MRI, is called the target task. All other tasks from which training information can be imported are called source tasks. The transfer learning paradigm for certain embodiments of MRI-based tracking as disclosed herein is based on three steps: (1) Choosing an appropriate source dataset, (2) Transferring information of the source dataset to the target, and (3) Utilizing the transferred information for performance gain on the target task.

Figure 20:
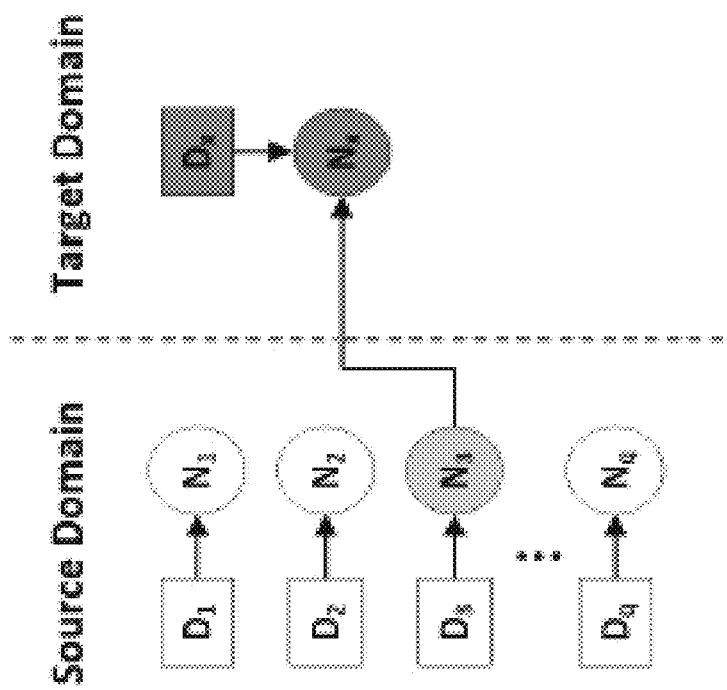
FIG. 20 shows feature layers can be transferred to initialize the CNN of a target task before it is trained on its target data.

Transfer learning can be performed between a source and target task using CNNs. A deep CNN learns a hierarchy of feature representations in multiple layers for a specific task. Generally, weights in these feature representation layers of a CNN are randomly initialized and then learned using task-specific training data. The features learned in the first few layers are very general and can be common across tasks, whereas the feature representations learned in the last few layers are more task-specific. However, once learned, some or all of these feature layers can be transferred to initialize the CNN of a target task before it is trained on its target data. This process is illustrated in FIG. 20. Given a specific source task, the inventors have determined a number of useful ways to exploit the transferred information for performance gain. Some sources are more useful than others for a particular target task.

1. The Disclosed Approach

Figure 21:
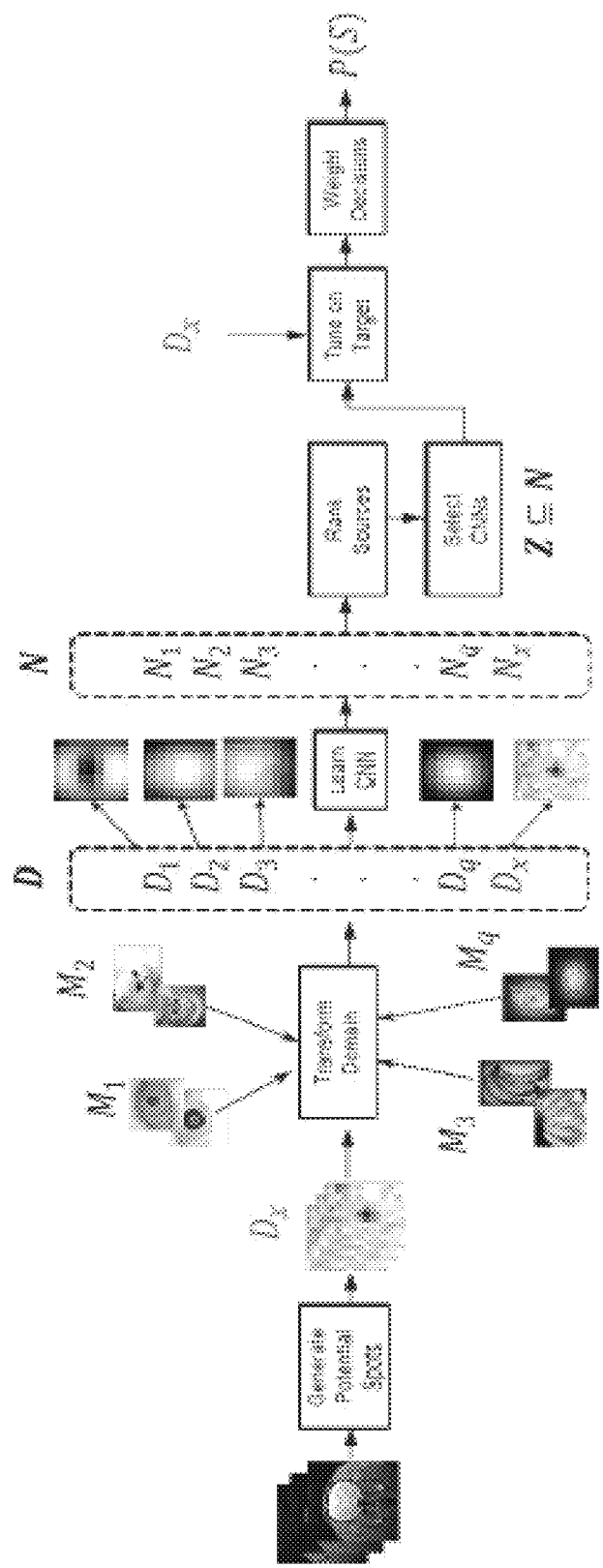
FIG. 21 shows an example of transfer learning architecture.

One potential architecture of the disclosed systems and methods employing transfer learning is shown in FIG. 21. A 3D MRI is first tessellated into a set of w×w 2D patches.

In the training data, patches noted as spots by an expert are labeled as such, while the remaining patches are labeled as non-spots. Hence, the target dataset $D_x$ is comprised of labeled patches. Based on the size of these patches, a domain transformation module transforms the image data $\hat{M}_i$ in the $i^{th}$ source task to an image set $D_i$, where the size of each image in $D_i$ is w×w. For each source $D_i$, a deep CNN $N_i$ is learned. At the same time, a target CNN $N_x$ is learned using the target data $D_x$. The source CNNs are then forwarded to a source ranking module that compares the characteristics of $N_x$ with each $N_i$, $i=\{1, 2, \ldots, q\}$ The sources are then ranked from best to worst based on an automated scheme that assigns a score to each source. Finally, based on the ranking scores, the top Z sources are selected for transfer learning. Each source CNN in set Z is then tuned on the target data $D_x$ to learn a net $N_{xh}$, where h∈Z. The conditional probability outputs of each tuned CNN is then weighted to present the final output by a decision weighting module. The individual modules are discussed in more detail below.

Generate Potential Spots

This module takes 3D MRI data as input and outputs a set of 2D patches each of size w×w. This step converts the detection of spots in 3D MRI to a binary classification task for deep CNNs. The 2D patches were obtained. Some of these patches have been labeled as spots (positive class) by human experts whereas the others are non-spot patches (negative class).

Domain Transformation

The goal of this step is to take the data $\hat{M}_i$ from each available source i and transform this data to make it compatible with the target data. The target data $D_x$ has two main characteristics. First, it is a two-class image data set, and second, each image has dimensions w×w. That is, $D_x=\{\hat{D}_x, Y_x\}$, where $\hat{D}_x$ is the set of images, and $Y_x$ consists of the corresponding labels.

First, to make each source a two-class dataset, a set of images is added to each. The additional images $\hat{B}_g$ composes the negative class of each source dataset. For example, augmenting background images to a set of cat images will generate a two-class data set. The image set $M'_i=\{\hat{M}_i \cup \hat{B}_g\}$ can then be created for each source i. Next, sample all images in to $M'_i$ to w×w resulting in the image set $\hat{D}_i=\{\hat{d}_i^1, \hat{d}_i^2, \ldots, \hat{d}_i^n\}$. The corresponding labels (positive class and negative class) for all these images are denoted by $Y_i$ and $D_i=\{\hat{D}_i, Y_i\}$.

CNN Learning

This module uses datasets $D=\{D_x, D_1, D_2, \ldots, D_q\}$ and learns a corresponding CNN for each dataset, producing $N=\{N_x, N_1, N_2, \ldots, N_q\}$. The structure of the generic CNN considered in this work can be denoted as $Q=\{L_1, L_2, \ldots, L_g, L_{fc}\}$ where each item in Q is a layer of the net. Each $L_j$, j≤g, can have up to three of the following components: (1) a convolutional layer, (2) a pooling layer, and (3) a gating layer. $L_{fc}$ follows the last layer $L_g$ and represents a fully connected layer. For the 3D MRI dataset with patch size of 9×9, each $L_j$ containing a convolutional layer $C^j$ followed by a non-linear gating function β. Further, the present disclosure utilizes the well-known ReLU function (Rectified Linear Units) as the gating function. In some circumstances, it may be desirable not to use pooling layers. Generally, pooling layers down-sample input images and impart translation invariance. In the problem at hand, since the size of the input patches is rather small, the pooling layers are not required. There is one $L_{fc}$ layer that utilizes a softmax loss function. The architecture of the resultant CNN is shown in FIG. 11.

Each CNN is randomly initialized and then trained on the corresponding source data to get a trained network. This can be denoted as $N_i = G(N_R, D_i)$, where G represents the training of a CNN, $N_R$ represents a CNN with randomly initialized weights for all layers, and $D_i$ represents the data used to train the network.

Source Ranking

Given source datasets and their corresponding CNNs, the goal here is to automatically rank all the sources from best to worst depending on how beneficial each is for transfer with respect to a given target. The disclosed approach first presents an intuitive analysis to understand the criterion for source mining the ranking score for each source that measures its usefulness.

Intuitive Analysis

The disclosed approach develops intuitive guidelines for determining source relevance to the target task. A CNN basically learns a hierarchy of features in its multiple convolutional layers. Initial layers learn generic features that are usually the same irrespective of the training task. The later convolutional layers learn high level features that are more specific to the training task and are then utilized by fully connected layers for classification. Let high level features learned by the target CNN $N_x$, on the limited data $D_x$, be $f_x$. Similarly, for each source CNN $N_i$, let the high level features be denoted as $f_i$.

In transfer learning, the layers corresponding to these the high-level features in the source domain (i.e., the $f_i$'s), are also transplanted into the CNN corresponding to the target domain, and further tuned based on the limited training data in the target domain. Learning the target feature representation, $f_x$, from the limited data $D_x$ will result in overfitting. However, transfer of $f_i$ adds generalization to the target domain by presenting a different set of feature representations. Hence, the difference between $f_i$ and $f_x$ is a beneficial property since transfer learning would then leverage new representation schemes that are not induced by the limited target dataset. In case, $f_i$ and $f_x$ are exactly the same, $f_i$ does not bring additional, unexplored knowledge to the target domain and the performance gain will be minimal. Semantic relevance between the source and target is also important to consider. Feature representations between source and target can be very different despite having high relevancy between domains. In fact, two very different datasets collected for the same task (e.g. face detection), can result in very different feature representations.

Therefore, both aspects, i.e., difference between feature representations as well as relevancy between domains, need to be considered while ranking sources.

Theoretical Analysis

The disclosed approach develops a theoretical understanding for ranking the sources. Here, the final goal is to accurately predict all the labels of the target test set, S. Now the uncertainty in predicting S can be modeled by H(S) where H( ) is the entropy function. Let $\hat{D}_x^T$ represent set of test images in the target domain and let $f_x(\hat{D}_x^T)$ be the features extracted from the test set. Since conditioning reduces entropy, it can be written:

$$H(S) \geq H(S|f\hat{D}_x^T)) \quad (1)$$

and with additional information, $$H(S) \geq H(S|f_x(\hat{D}_x^T)) \geq = H(S|f_x(\hat{D}_x^T), f_i(\hat{D}_x^T)). \quad (2)$$

This shows that extracting additional features $f_i(\hat{D}_x^T)$ from a source CNN, $N_i$, can potentially reduce the uncertainty in predicting S. The amount of reduction in uncertainty is referred to as a "gain". Eqn. (2) can, therefore, be written in terms of gain as:

$$\text{gain} = H(S) - H(S|f_x(\hat{D}_x^T), f_i(\hat{D}_x^T)), \quad (3)$$

$$= I(S; f_x(\hat{D}_x^T)) + I(S; f_i(\hat{D}_x^T)|f_x(\hat{D}_x^T)). \quad (4)$$

where $I(S; f_x(\hat{D}_x^T))$ denotes the mutual information between S and features $f_x(\hat{D}_x^T)$. The higher this mutual information, the lesser the uncertainty in predicting S. Note that the second term $I(S; f_i(\hat{D}_x^T)|f_x(\hat{D}_x^T))$, represents the gain due to a specific source, that is not already accounted for by $f_x(\hat{D}_x^T)$. If $f_i(\hat{D}_x^T) = f_x(\hat{D}_x^T)$, then gain due to the source will be zero. On the other hand if source i is completely irrelevant to the target, the mutual information between them will be zeros, resulting in a zero gain.

Thus, the theoretical analysis emphasizes both aspects, i.e., the notion of exploiting a different feature representation method and determining the relevancy between domains. Further, since the test data is not available during the training phase, the training data itself has to be used for computing the terms above. However, it may not be appropriate to use the predictiveness (e.g. mutual information) of $f_x$ or $N_x$ as a metric, as a CNN would over-fit on small training data $D_x$, and therefore the mutual information between labels $Y_x$ and features $f_x(\hat{D}_x)$ will be artificially very high (very predictive).

Designing a Quantitative Measure

Based on the previously developed intuitions, the disclosed approach presents a quantitative measure $E_i^{RS}$ to estimate the ranking score (potential usefulness) of a source i to the target x.

$$E_i^{RS} = \max(E_i) \quad (5)$$

where $$E_i = \lambda \hat{U}_{ix} + (1-\lambda) \hat{J}_{ix} \quad (6)$$

The higher the value of $E_i^{RS}$, the better the source for the specific target problem. $\hat{U}_i$ is a vector that measures the difference between target and source feature representations whereas $\hat{J}_i$ is a vector representing the domain relevance between the source and target. $\lambda$ is simply a weighting parameter.

Figure 22:
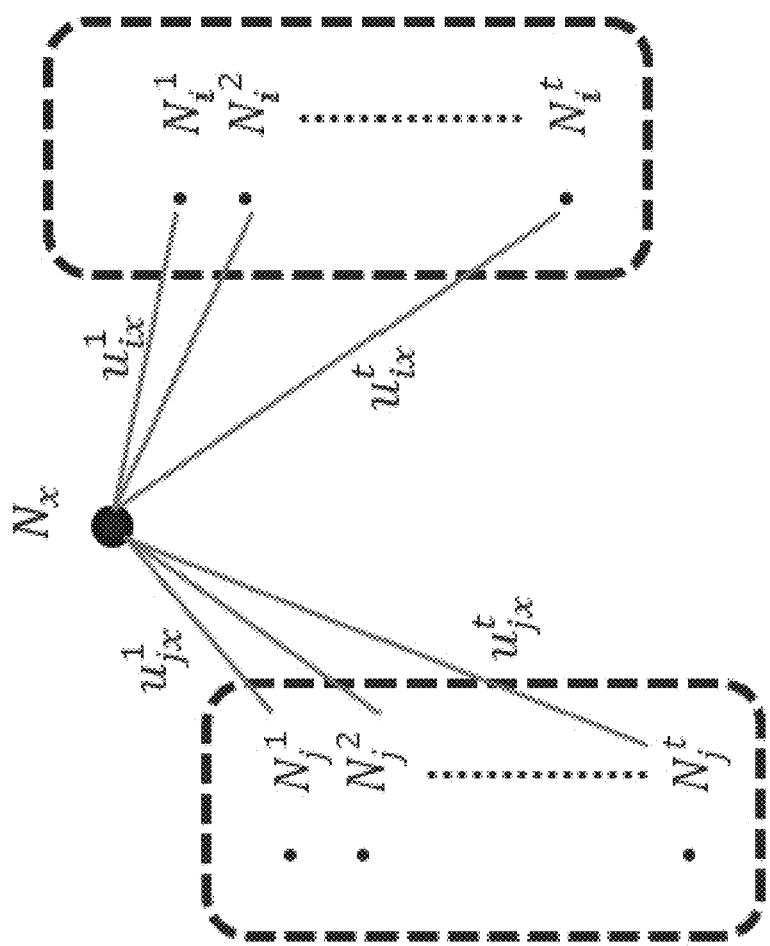
FIG. 22 shows a conceptual representation of extracting a different set of knowledge from input data.

Difference in Feature Representation:

First, as can be seen from Eqn. (4), the in the disclosed approaches for source features $f_i$ to provide additional gain, they should be predictive by extracting a different set of knowledge from input data. Therefore, consider a feature representation space where $f_i$ and $f_x$ are simply two points. Note that $f_i$ represents the high level features of $N_i$ and therefore denotes all the weights in the last convolutional layer $L_g$ of $N_i$. Now let $f_i^u$ be its normalized vector representation. In this space, the disclosed approach can compute the difference between two feature representations as $u_{ix} = \|f_x^u - f_i^u\|_2$ Where $f_x^u$ denotes a normalized vector containing all the feature weights represented by $f_x$. Training a CNN through t epochs actually creates a path of t CNNs. For each source i let the CNN formed at epoch number $\tau$ be denoted as $N_i^\tau$ and its corresponding feature representation as $f_x$. Due to non-linearity of the path of convergence (induced by the stochastic gradient descent algorithm), a different CNN other than the source, can possibly provide a larger feature distance. Therefore, $U_i = \{f_{ix}^\tau\}_{\tau=1}^t$. Meaning, the target CNN's feature distance from all the intermediate t points is computed. A conceptual representation of this is shown in FIG. 22. Thus, each source will be represented by a t-dimensional vector measuring the distance of the target's CNN to the path of convergence of the source CNN.

Figure 23:
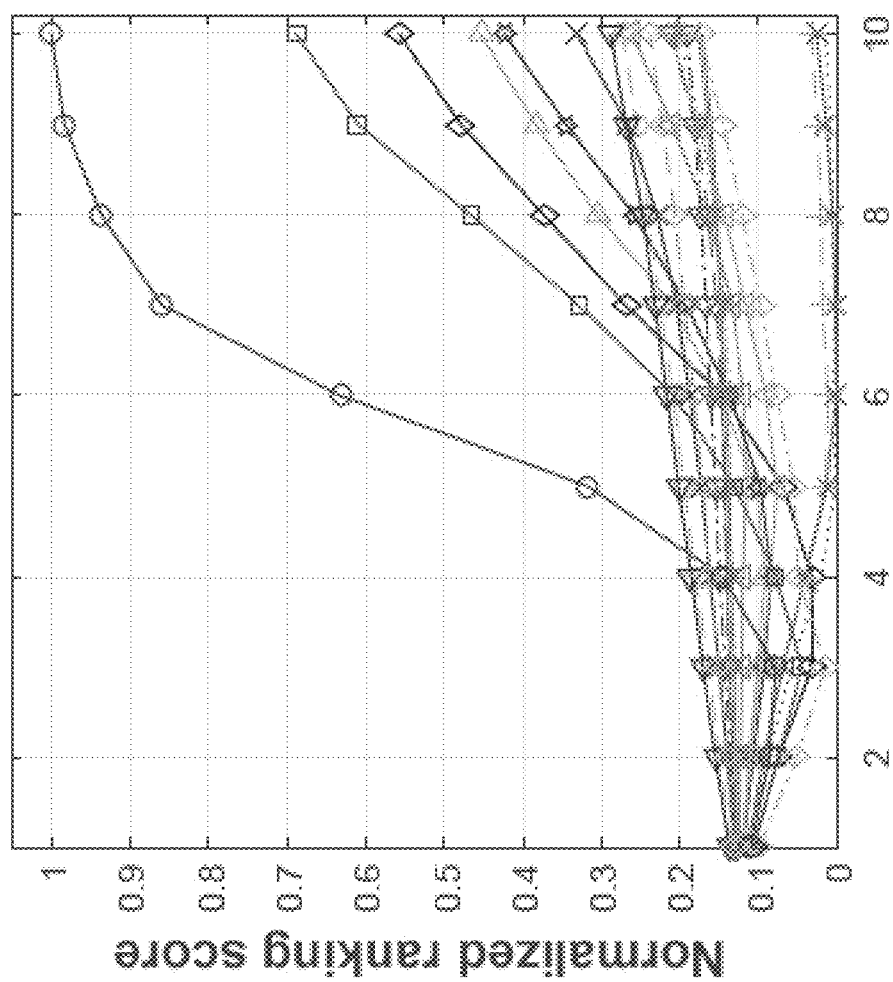
FIG. 23 shows the vector $E_i$ as a curve for several different tasks based on the distance of the target from the path of convergence of each source.

Domain Relevance:

To determine the domain relevance between source and target, the disclosed approach measures how well can a source CNN $N_i$ generalize to the target task without using the target training data. For example, if the source and target represent the same task, e.g., face detection, relevance should be very high. Therefore, take the $N_i$ trained on source data as it is, and present the limited target training data $D_x$ for testing. The disclosed approach then measures its accuracy $j_{ix}$ in predicting labels $Y_x$. Since, each source has t CNNs along the path, a series of accuracies are obtained $J_i = \{j_{ix}^\tau\}_{\tau=1}^t$ where $j_{ix}^t$ denotes the performance of $N_i^t$. Thus, each source can now be associated with 2 dimensions. One measuring feature differences and the other measuring domain relevancy. For each source i, compute an t-dimensional $E_i = \lambda \hat{U}_{ix} + (1-\lambda) \hat{J}_{ix}$ where $\hat{U}_{ix}$ and $\hat{J}_{ix}$ are the normalized versions of $U_i$ and $J_i$. Each source nominates its max($E_i$) value for comparison with other sources. The higher the value the better the source choice for the target task. FIG. 23 shows the vector $E_i$ as a curve for several different tasks based on the distance of the target from the path of convergence of each source.

CNN Selection and Tuning on Target

Next, the disclosed approach selects a set Z of top ranked CNNs, where $Z \subseteq N$. For each CNN $N_i \in Z$, the limited target training data is then used to update it and obtain $N_{xi}$. This tuned CNN $N_{xi}$ is then used to classify test data $D_x^T$.

Decision Generation Using Information Fusion

If $|Z|>1$, the disclosed approaches will have more than one tuned net. Let $|Z|=2$, and let the two selected CNNs be $N_{xi}$ and $N_{xj}$ respectively. Each of these tuned CNNs can predict spot labels S in the test data using the conditional probability distributions of $P(S|N_{xi})$ and $P(S|N_{xj})$, respectively. The disclosed approach combines the two conditional probabilities as follows:

$$P(S) = \zeta_i P(S|N_{xi}) + \zeta_j P(S|N_{xj}). \quad (7)$$

Now for P(S) to be a valid probability distribution, the sum of the weighting terms must be 1, i.e., $\zeta_i + \zeta_j = 1$. To compute the weighting terms for the solutions that originated from two different tasks i and j, and exploit their ranking scores which gives, $$\zeta_i = \frac{(E_i^{RS})^b}{(E_i^{RS})^b + (E_j^{RS})^b} \quad \zeta_j = \frac{(E_j^{RS})^b}{(E_i^{RS})^b + (E_j^{RS})^b} \quad (8)$$

Thus, for any arbitrary $|Z|=h$, this approach can be extended such that $\Sigma_{k=1}^h \zeta_k = 1$.

2. Experiments, Results and Discussion

In this section several experiments are described, that were conducted to study performance aspects of the disclosed approaches using transfer learning.

Source Datasets:

A diverse set of 20 different source datasets were used in this analysis. Iris images were taken from the CASIA-IrisV4 database whereas the rest of the images were taken from imageNet. The names of the source datasets are indicated in Table 4. As stated earlier, a number of background images were added to each of these datasets in order to generate the negative class. About 1000 publicly available images were taken from a popular search engine by typing the following key words: (1) texture patterns, (2) road textures, (3) grass, (4) sky and ocean.

TABLE 4

| The source datasets used in this approach | | |
|---|---|---|
| Iris | Banana | Brown rice |
| Golf ball | Apple | Hunting dog |
| Cheese burger | Cherry | Draft animal |
| Pulsar | Soccer ball | Stars |
| Egg white | Fried Egg | Tennis ball |
| Burger | Persian cat | Egg |
| Supernova | White rice | |

Target Datasets:

This data comprised three different MRI scans of rat brains tagged by experts. On average, each MRI scan generated about 150,000 candidate patches with 5000 being labeled by experts as spots (positive class). For training, a small percentage of patches are taken from the MRI scan of one rat. The patches from the other two unrelated MRI scans are used as two independent test sets to create a pair of testing scenarios. The percentage of the training data was varied in the experiments. Each MRI scan was used once for training. This created a total of six different testing scenarios.

Setup and Parameters:

To implement CNNs, the disclosure utilized the standard implementation. Details about filter sizes, feature maps and number of layers are summarized in FIG. 11. In the study, t=10, q=20, w=9, b=1 and g=3. Area Under the ROC Curve (AUC) was used as a measure of accuracy in the experiments. Experiments were conducted on an Intel® Core™ i7-4790 3.6 GHz machine with 32 GB RAM.

Impact of Size of Target Training Set

Figure 25:
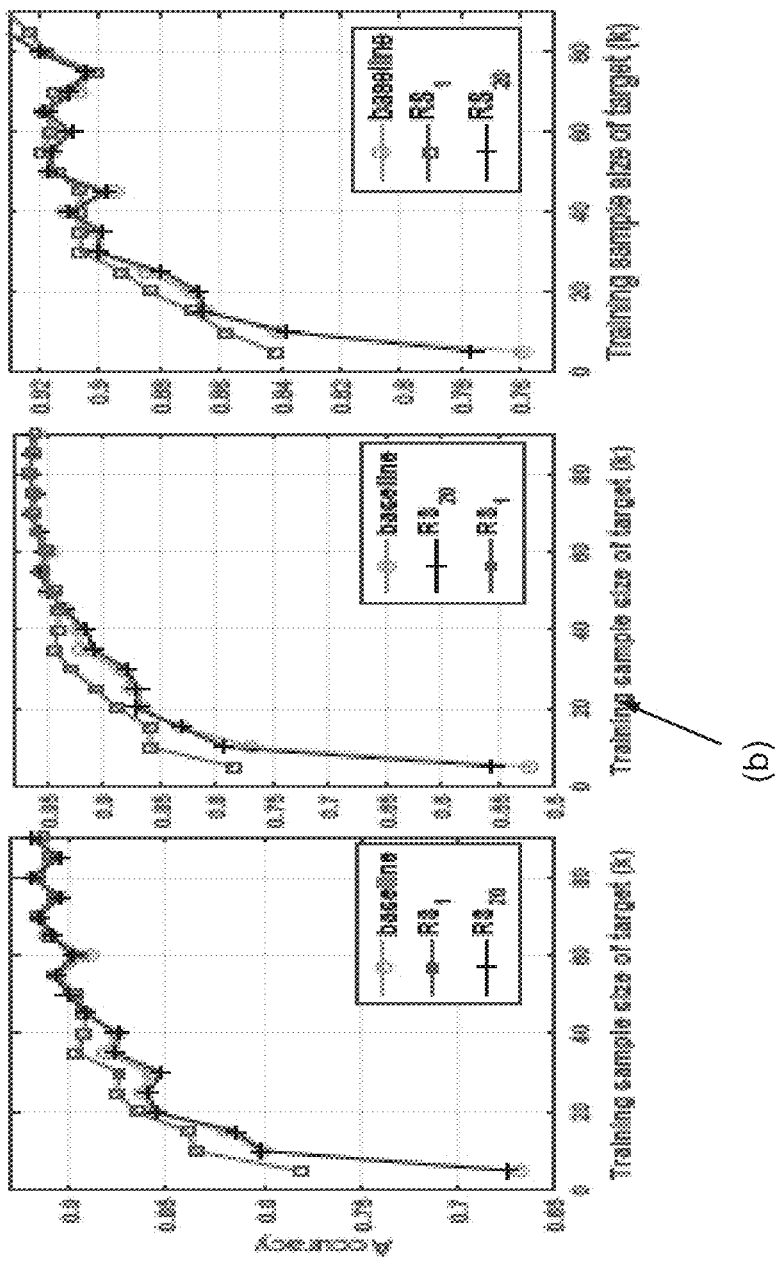
FIG. 25 shows the results on the three different testing scenarios.

In this experiment, the following were compared: (1) the performance of transfer learning when using the source that was ranked the best ($RS_1$) against the source that was ranked worst ($RS_{20}$) by the proposed source ranking module. (2) Performance of $RS_1$ and $RS_{20}$ against a baseline CNN that was only trained using target training data $D_x$, with no transfer learning. (3) Performance of the aforementioned CNNs using a different percentage of target training data. Training was accomplished with 18 different percentage values from 5% to 90% of the training set in increments of 5. FIG. 25 shows the results on the three different testing scenarios. FIG. 25 indicates a performance gain of about ~22% with respect to the baseline when only 5% of the target training data is used (b). The disclosure further observes that the performance gain is more significant when the training data is smaller in size which is exactly the goal of this study. However, as the training size increases, $D_x$, becomes more capable of providing a more comprehensive representation of the "spot" and hence the significance of using an external source decreases.

Correlation Between Source Ranking and Performance Gain

Figure 24:
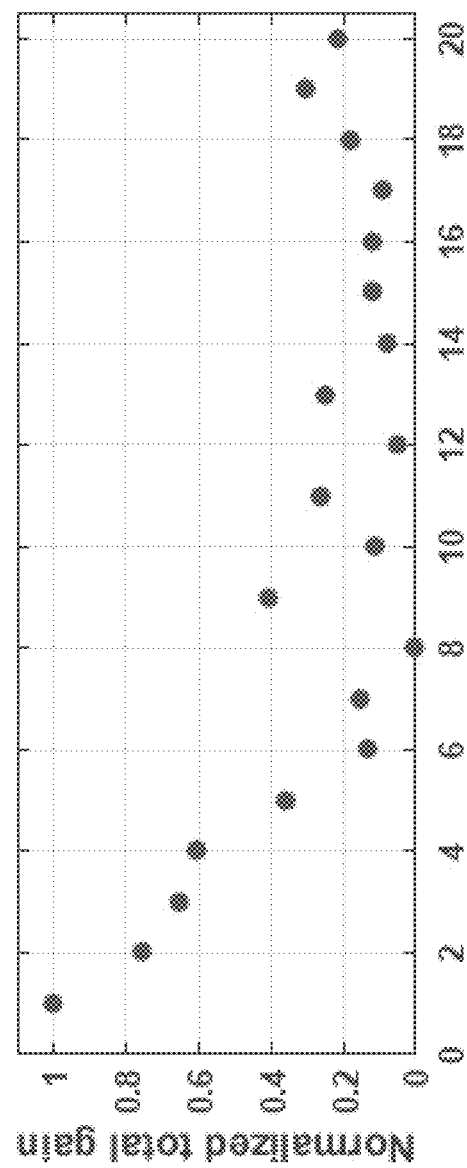
FIG. 24 shows an example correlation where the x-axis represents the tasks ranked by the proposed approach with a '1'.

In FIG. 24, the x-axis represents the tasks ranked by the proposed approach with a '1' indicating the top-ranked source and '20' the worst-ranked source. The y-axis shows the normalized sum of the overall performance gain achieved by using that source in all the aforementioned 18×6 scenarios (18 training sets, 6 test cases). Note the correlation between the ranking provided by the proposed algorithm and the actual performance gain, which shows that the proposed metric is a reasonable substitute allowing automating the process of source selection in transfer learning.

Comparison with Human Rankings

As a comparison, another experiment was performed in which five computer science Ph.D. students were requested to select the top 5 sources out of 20 and rank them from best to worst for the target task. Each student manually analyzed the original source images and also the domain transformed images and then compared them with a number of patch images from the given target dataset. Source ranked best by a student was given 5 points and the worst was given 1 point.

Two important observations are made: (1) The rankings were subjective and differed significantly from person to person, and therefore as shown in Table 5, Cherry and Iris were both ranked the best. (2) None of the experts listed the actual best source in their top-5 list whereas the proposed automated approach consistently picked it. In larger databases, where thorough manual analysis is extremely difficult if not infeasible, manual selection of a relevant source can be a challenge, thus further highlighting the importance of the proposed approach.

TABLE 5

Comparison with manual ranking

| Source | Actual rank | Our's | Manual |
|---|---|---|---|
| Supernova | 1 | 1 | Missed |
| Iris | 2 | 2 | 1 |
| Pulsar | 3 | 3 | Missed |
| Cherry | 4 | 4 | 1 |

Layers to be Transferred

Figure 26:
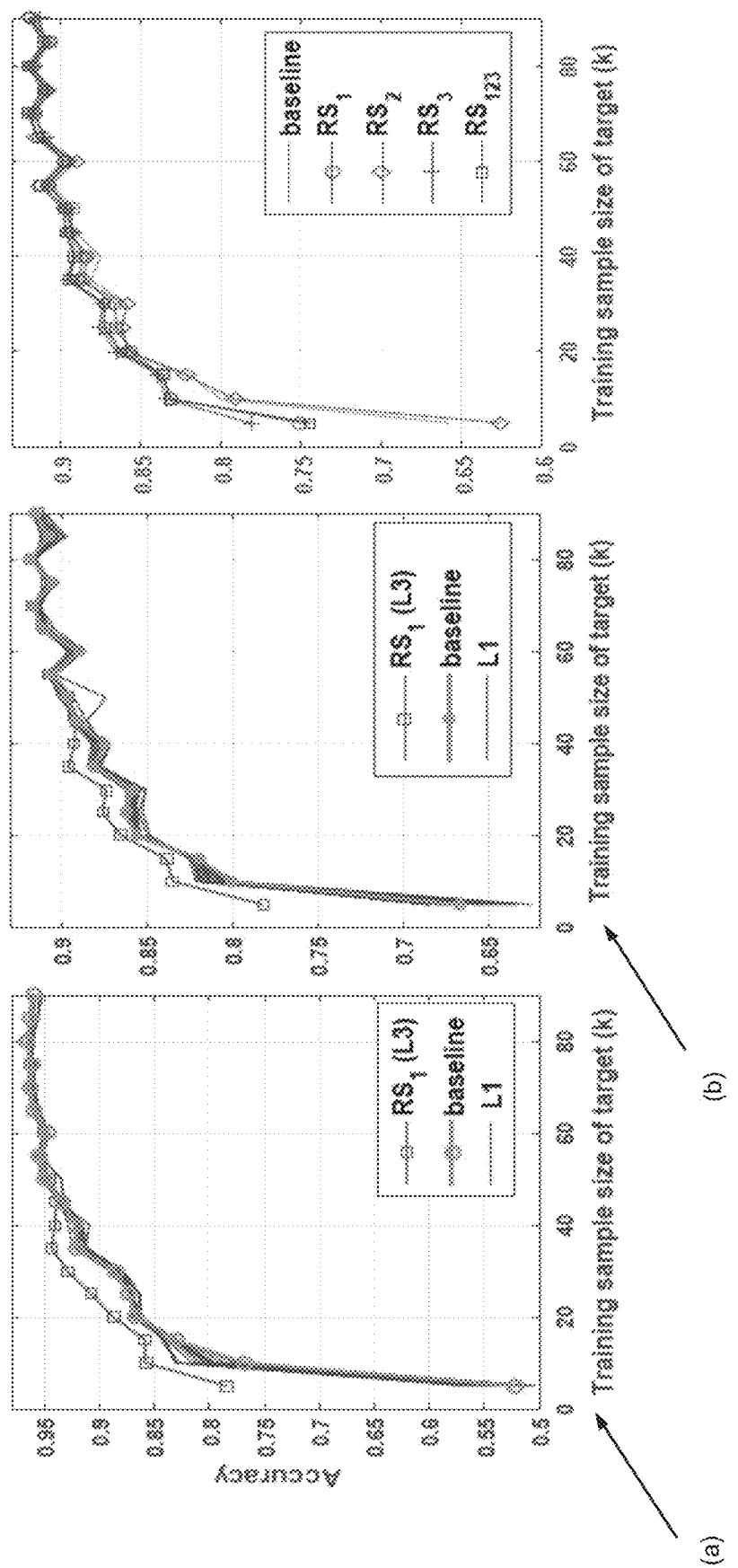
FIG. 26 compares the performance when (a) only the most general layer is transferred from source CNNs, and (b) all three layers are transferred from the best ranked source.

In (a) and (b) of FIG. 26, the performance is compared between instances when (a) only the most general layer is transferred from source CNNs, and (b) all three layers are transferred from the best ranked source. The most general layer was transferred for all the 20 sources (shown as 20 curves and indicated by L1). The advantage of transferring more layers can be seen once the source ranking is known. For example, the ranking scores may be utilized to determine the number of layers that can be transferred.

Benefit of Information Fusion

Due to the weighted decision making policy, the performance achieved will be less affected by anomalous rankings that are inadvertently introduced. In FIG. 26, the disclosure presents a case having three sources indicated as $RS_1$, $RS_2$, and $RS_3$. Here, $RS_3$ represented a bad source that was incorrectly ranked high by the disclosed algorithm. However, the weighted/combined $RS_{123}$ can be seen to have performed significantly better than $RS_3$ and at many points performed better than others too.

The experiments conducted used the same setup mentioned above. Their approach followed a leave-2-out approach using all five MRI scans. Thus, the disclosed systems and methods achieve a significantly better performance despite using limited data. In comparison to mean AUC of 89.1% achieved by methods discussed above, the disclosed transfer learning systems and methods achieves 91.36% accuracy when only using 40% of the training data, and with complete training data the disclosed transfer learning approach achieves 94.6%. The foregoing transfer learning methods may work equivalently well using machine learning algorithms other than CNNs, such as AutoEncoders.

Example of Utilizing Metrics for Assessing Source Task

Figure 27:
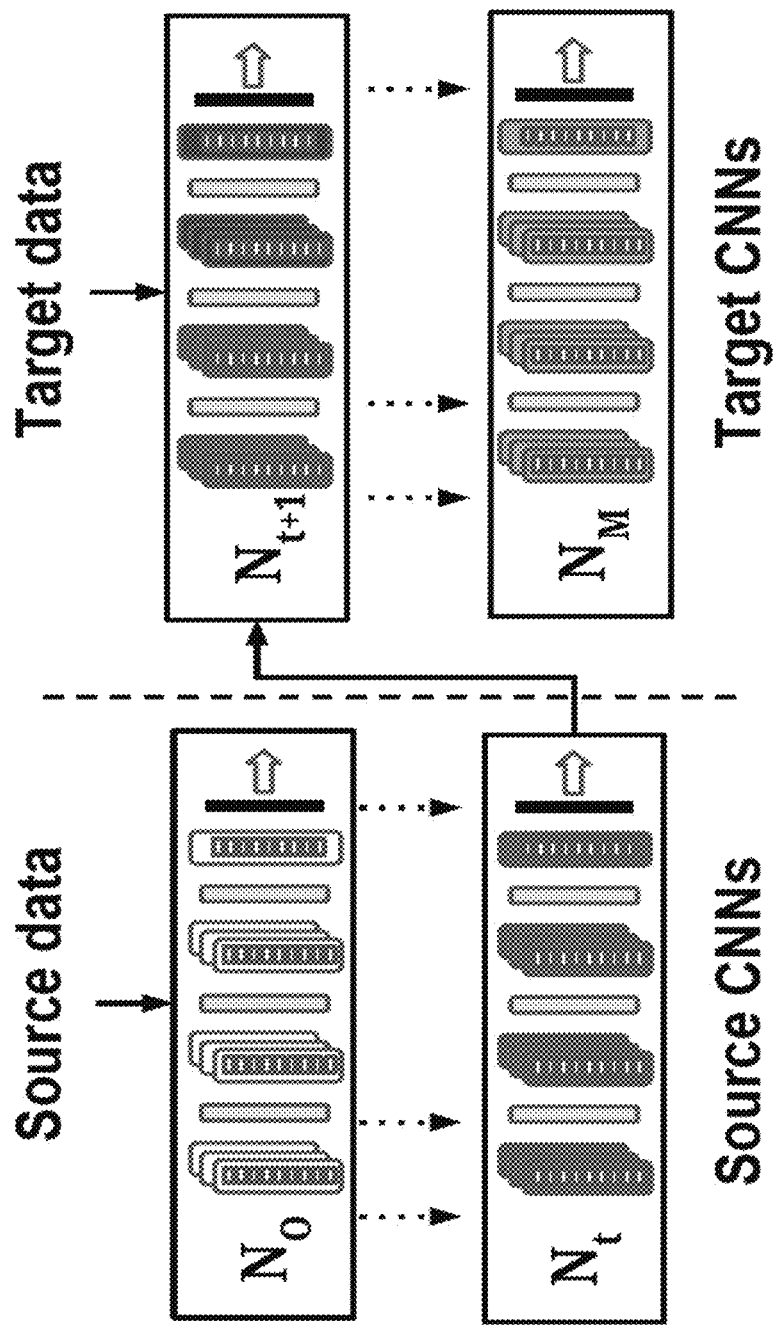
FIG. 27 shows an example of transfer learning in CNNs.

The question may be raised when performing the machine learning using CNNs: Given a target task with limited training data and a large number of available source tasks, can the best source task(s) be automatically selected in order to facilitate transfer learning? The disclosure herein proposes a method for automatically selecting the source task(s) for transfer learning in CNNs. FIG. 27 shows an example of transfer learning in CNNs.

Technical Challenges and Contributions

The problem of automatic source task selection in CNNs presents many challenges. A number of these challenges are listed below along with the solutions that have been proposed in this disclosure.

Limitation of Data Comparison Methods:

One approach to selecting a source task from a set of tasks can be to compare characteristics of the target task's training data with characteristics of the source task's training data. However, due to the large scale, high-dimensional image data used in CNN based studies, this method of source task selection is not practical for use in CNN based transfer learning. This is because the images have large intra-class variation, it is unclear what features should be extracted from the images, and working with the direct image data may be computationally heavy. Therefore, this disclosure uses the weights of a CNN created using the source data for measuring its transferability (usefulness for target task). As described below, in the absence of information about source data characteristics, the proposed approach can effectively rank sources from best to worst for a given target task (that has limited training data).

Incomplete Understanding of CNN Characteristics:

The current understanding of CNN characteristics is fairly limited. For example, it is not known what characteristics of a source CNN are correlated with performance gain in the target task. The goal is to understand and measure such characteristics of a CNN prior to conducting the transfer.

CNN Structural Complexity:

CNNs exhibit a multi-layer structure with complex neuronal connections across layers. In order to gain a deeper insight into the complex set of learned weights, a number of studies have adopted the use of visualization based methods. However, the use of quantitative measures to characterize the weights of the CNN has not been extensively studied. This disclosure attempts to bridge this gap by proposing such a measure based on the solution space of a CNN, and demonstrates its utility in the context of transfer learning.

Performance Gain on a Real World Target Application:

Large scale data collection and annotation is impractical in many applications, especially in the medical domain. Therefore, transfer learning has high-impact potential on real world, data-limited tasks. In this disclosure, an existing MRI database is utilized as a target task. This target task requires the detection of small indicator cells in cellular brain MRIs. Due to high inter-class variation and data noise, object detection is a challenging task. This disclosure establishes a detection accuracy on the target task by significantly outperforming the current best known methods.

Understanding CNN Characteristics

CNN Architecture and Layer Transfer

Independent basic definitions are mentioned in the following text. Consider a multi-layered functional CNN architecture, $N^i$, $$N^i = f(T^i) = f_o^i(f_{u+1}^i(f_u^i(f_{u-1}^i(f_{u-2}^i(\ldots f_1^i(T^i)\ldots))))) \quad (1)$$

where, the superscript i denotes the task number and $f_a^i$ represents the $a^{th}$ layer of the network. The $u+1^{th}$ functional layer $f_{u+1}$ contain a set of fully connected layers that takes the output obtained from $f_u$ as an input. Each of the remaining layers further contains a convolutional layer, a pooling layer and a non-linear gating layer. During the training process, the weights in the convolutional layers and fully connected layers of $N^i$ are first randomly initialized resulting in $N^R$. By using the training data $T^i$ from source task i, weights in the layers are learned resulting in task i specific CNN, $N^i$. This training can functionally be denoted as $N^i = h(N^R, T^i, Y^i)$ where $Y^i$ represents the corresponding labels of $T^i$. Similarly, for another source task j, $N^j = h(N^R, T^j, Y^j)$ can be learned. However, given $N^i$, the CNN $N^j$ can also be learned using the weights of $N^i$ as the initial weights, i.e., $N^{ji} = h(N^j, T^j, Y^j)$ through the process of transfer learning (see FIG. 27 for a detailed description of transfer learning). Here, i represents the source task and j denotes the target task. Note that throughout this study, $N^R$ will be strictly assumed as a randomly initialized CNN with, principally, no potential for solving any practical task in itself. It can also be denoted as $N^R = h(N^R, \{ \}, \{ \})$. Further, CNNs initialized by $N^R$ (e.g. $N^i$) will simply be written as $N^i$ and not $N^{iR}$.

TABLE 6

Summary of notations used in this approach

| Symbol | Description | Symbol | Description |
|---|---|---|---|
| D | Target test images | $Y^D$ | Target test labels |
| X | Target train images | $Y^X$ | Target train labels |
| $N^D$ | CNN learned on (D, $Y^D$) | $N^X$ | CNN learned on (X, $Y^X$) |
| $N^i$ | CNN for source i | $N_\tau^i$ | CNN for source i at epoch $\tau$ |
| $N^{Dk}$ | k convolutional layers of $N^D$ | $F^{Dk}$ | Feature maps of k CNN layers |
| $T^i$ | Training data for source i | $f_u^i$ | Deepest composite layer of $N^i$ |
| $N^{ji}$ | $N^i$ tuned on $T^j$ | $\phi_\tau^{(ij)m}$ | Solution diff. btw $N_\tau^{(ij)}$ and $N^m$ |
| $W^i$ | Convolutional weights in $f_u^i$ | $\phi_\tau^{ij}$ | = $\|W_\tau^i - W^j\|_2^2$ solution difference |
| $P_\tau^i$ | = $[N_0^i, N_1^i, \ldots, N_\tau^i]$ Path i | $\Phi_\tau^{ij}$ | = $[\phi_0^{ij}, \phi_1^{ij}, \ldots, \phi_\tau^{ij}]$ Profile i |
| $E^i$ | source i ranking score | $e_\tau^i$ | Ranking score of only $N_\tau^i$ |

Note that for transfer learning to be applied, the layers to be transferred from N must be of the same architecture as those of the target CNN $N^j$. Moreover, the research has shown that any subset of k layers can be transferred. Different values of k can yield different results in the target task. It was also shown that the weights of an activation layer could also be learned. Therefore, weights from the activation layer can also be transferred along with the weights from the convolutional and fully connected layers. Table 6 summarizes notations used in this approach.

Understanding Source Characteristics for Performance Gain

As stated earlier, it is still unclear as to what characteristics of a source CNN would make it more useful than others with respect to a target task.

Consider a CNN $N^i = h(N^R, T^i, Y^i)$ trained on task's i training data. Similarly consider another CNN $N^X = h(N^R, X, Y^X)$ trained on target's training data. Both these CNNs were initialized using same $N^R$, however, due to difference in training data they capture different feature representations. Next, $N^i$ is then undertaken for further training using the target's training data which can be denoted as $N^{Xi} = h(N^i, X, Y^X)$. This initialization with $N^i$, rather than $N^R$ is clearly a difference between learning with and without transfer.

Note that if $N^i = N^R$ there will be no gain. Thus, this difference is a desirable property resulting in gain. This difference between $N^R$ and $N^i$ represent a set of feature representations learned to solve task i. It is possible that some these are also relevant to the target domain and can be reused or customized, adding diversity. This will be significantly beneficial for target tasks with smaller datasets. Empirical results clearly demonstrate that an initialization of target CNN based on a source $N^i$ having a larger difference from $N^R$ resulted in higher gain than that with lesser difference. This was especially true for smaller datasets. On the other hand, a target's training set that is substantially large, may comprehensively provide relevant information for accurate CNN learning, leaving little room for source task's CNN to provide additional relevant knowledge to the target task. Thus, maximizing the difference between $N^R$ and $N^i$ in such cases may only be modeling more irrelevant features.

Defining a CNN Solution Space

Consider a high dimensional solution space, N, with each point denoting the weights in the layers of a CNN that are transferred. For a fixed CNN architecture, each point in this space denotes a CNN based solution for some task. For example, one point in this space may represent an ideal solution for the face-recognition problem whereas another may represent a non-ideal solution for disease estimation. It is known that the weights in the initial layers of a CNN act as general feature extraction operators and, thus, the CNNs for many different tasks may have similar first layers; in contrast, the weights that are in the deeper layers of the network become increasingly task specific. Hence, the weights in the deepest convolutional layers represent the most task specific weights and are utilized here to denote a CNN.

Solution Difference:

This measures the Euclidean distance between two points in the solution space. Solution difference between two CNNs Ni and $N^j$ is computed as $\Phi^{ij} = \|W^i - W_j\|_2^2$. Here $W^i$ and $W^j$ are two points in solution space denoting Ni and $N^j$ respectively.

Solution Path:

During training, a CNN is first initialized to a point (random or otherwise) in the solution space. Then the learning algorithm adjusts the weights incrementally after each epoch, and the updated weights traverse a path in the solution space, referred to here as the solution path. For a task i, let $P_\tau^i = [N_0^i, N_1^i, \ldots, N_\tau^i]$ denote its solution path, where $N_\tau^i$ denotes the solution point at epoch $\tau$ and $N_0^i$ represents the initialization point. Note that when there is no transfer learning, $N_0^i = N^R$.

Path-to-Point Profile:

A sequence of differences between a CNN $N^j$ and each point in $P^i$ can be computed using the solution difference measure above. This results in a sequence of differences $\Phi_\tau^{ij} = [\Phi_1^{ij}, \ldots, \Phi_\tau^{ij}]$, where $\Phi_0^{ij}$ is the solution difference between $N_0^i$ and $N^j$.

Source Ranking

Given a source CNN $N_\tau^i$ and a randomly initialized CNN $N^R$, the ranking score can be computed as, $$E^i = \phi_\tau^{iR}, \qquad (2)$$

Now, the training process results in $\tau$ intermediate CNNs: i.e., the CNNs in $P_\tau^i$. Any of these $\tau$ CNNs could potentially be a suitable candidate for transfer learning; it is not necessarily the case that $N_\tau^i$ will result in the best performance gain after transfer on the target task. Therefore, the criterion $E^i$ is updated as, $$E^i = \max\{\Phi_\tau^{iR}\}. \qquad (3)$$

Note that the development of $E^i$ relies on the fact that small training datasets, in general, are incapable of imputing a comprehensive representational power to a CNN. Since, transfer learning is mainly beneficial for target tasks having limited training data, this approach is expected to work well when the target training data is limited. When the size of the training data for the target task is large, empirical results show that the performance gain due to transfer learning is less significant.

Information Fusion Using Multiple Sources

Transfer learning can involve transferring information from multiple source CNNs, Z, simultaneously, rather than from a single CNN only. Suppose that $|Z|=2$, and let the two source CNNs be $N^i$ and $N^j$, respectively. Let $N^{Xi}$ and $N^{Xj}$, respectively, be the updated CNNs after transfer learning. The CNNs are updated using the training data, X, from the target task. The output of each CNN is the set of probabilities indicating the posterior probability that the given input belongs to a particular class (label). Because each CNN will predict the class labels of the input data differently, the respective probabilities can be denoted as $P(S|N^{Xi})$ and $P(S|N^{Xj})$, respectively where S represents a testing sample. These two expressions can be combined as:

$$P(S) = \zeta_i P(S|N^{Xi}) + \zeta_j P(S|N^{Xj})$$

Using the ranking scores, the weights can be computed as:

$$\zeta_i = \frac{E^i}{E^i + E^j}, \quad \zeta_j = \frac{E^j}{E^i + E^j}. \quad (5)$$

For any arbitrary $|Z|=d$, this approach can be extended such that $\Sigma_{k=1}^{d} \zeta_k = 1$.

Experiments, Results and Analysis

Experimental Setup

Figure 28:
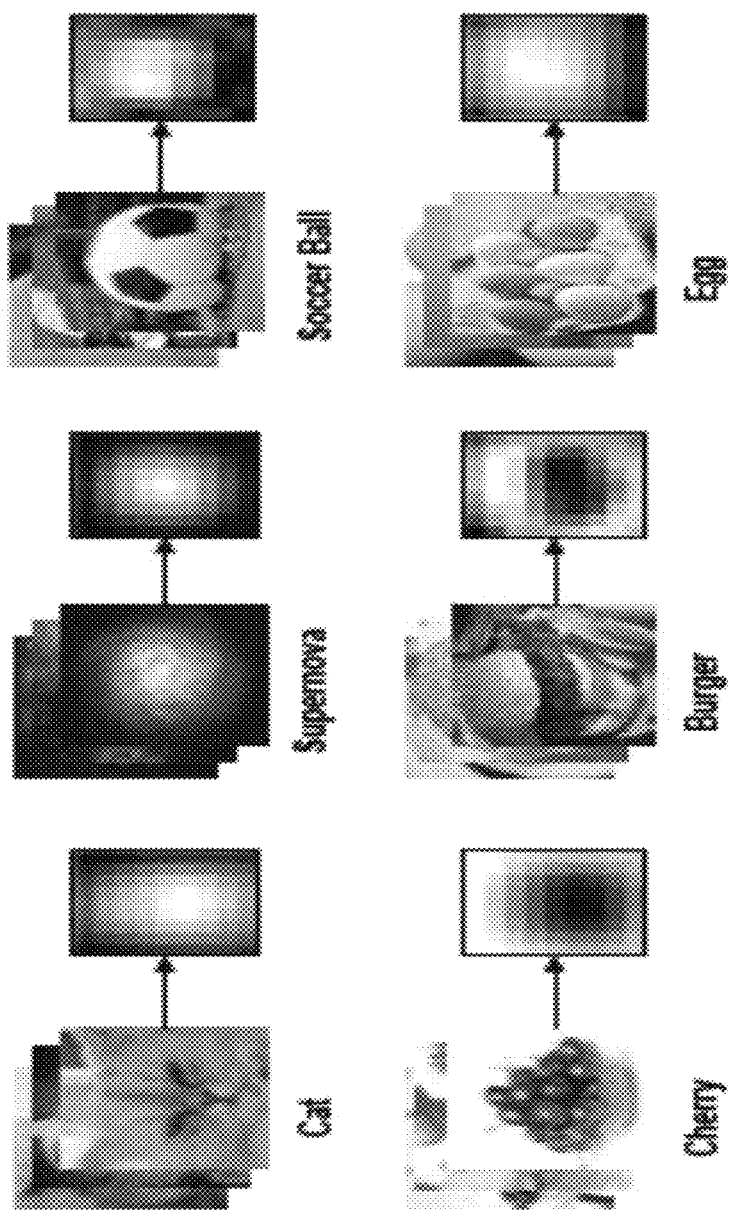
FIG. 28 shows extracted non-spot patches and spot patches.

Target Task:

Since many medical applications specifically suffer from the lack of large scale annotated data, in this study, an existing, real world MRI database was utilized as a target task. The task requires the detection of small stem cells in an MRI image which is a very challenging problem due to the high degree of variability in the data and the presence of various types of noise. This database has three different sets of labeled MRI scans pertaining to rat brains. The injected stem cells appear as dark spots in these images. From each scan about 100,000 non-spot patches and 5000 spot patches were extracted as shown in FIG. 28. These patches were obtained directly from the authors in. In the experiments below, all patches from a single scan (single set) were used for training and the patches from the remaining two scans were independently utilized for testing, generating a total of 6 testing scenarios. In all the experiments, the Area Under the Curve (AUC) was utilized for summarizing classification accuracy.

Source Task:

The focus of this study is to rank a set of given source tasks in order to determine their transferability for a fixed target task. Therefore, 25 diverse source tasks were arbitrarily designed using the publicly available, standard ImageNet database. Fourteen of these were binary classification tasks, while the number of classes ranged from 5 to 20 for the remaining source tasks. Note that the goal here is to be agnostic to the data characteristics of a source and only utilize the weights learned by the source CNN to assess its transferability to the target domain.

CNN Architecture:

The CNN architecture used in this study is illustrated in FIG. 11. Note that since the size of input image patches is only 9×9, pooling layers are not used in this architecture. In this study, transfer learning involves transplanting all the convolutional layers learned on the source data to the target CNN, except when otherwise mentioned. Generally, fully connected layers are not transferred due to their high task-specificity and (source) task based structural variability.

As disclosed below, experiments are designed to study the following questions: (1) How well does the proposed approach rank the sources from best to worst? (2) What is the difference in performance when the best ranked source is used for transfer learning in comparison to the worst ranked source? (3) What is the gain in classification accuracy when results are compared against a CNN without any transfer learning? (4) How does the size of the target training data impact the performance gain? (5) What role does the choice of layers, that are transplanted, have on transfer learning? (6) Does the information fusion of sources provide robustness against ranking errors? (7) Can the negative impact of transfer learning be predicted in advance, based on the source task's ranking score? (8) What does the ranking score of a source task tell us about its data characteristics?

Experiments

Figure 29:
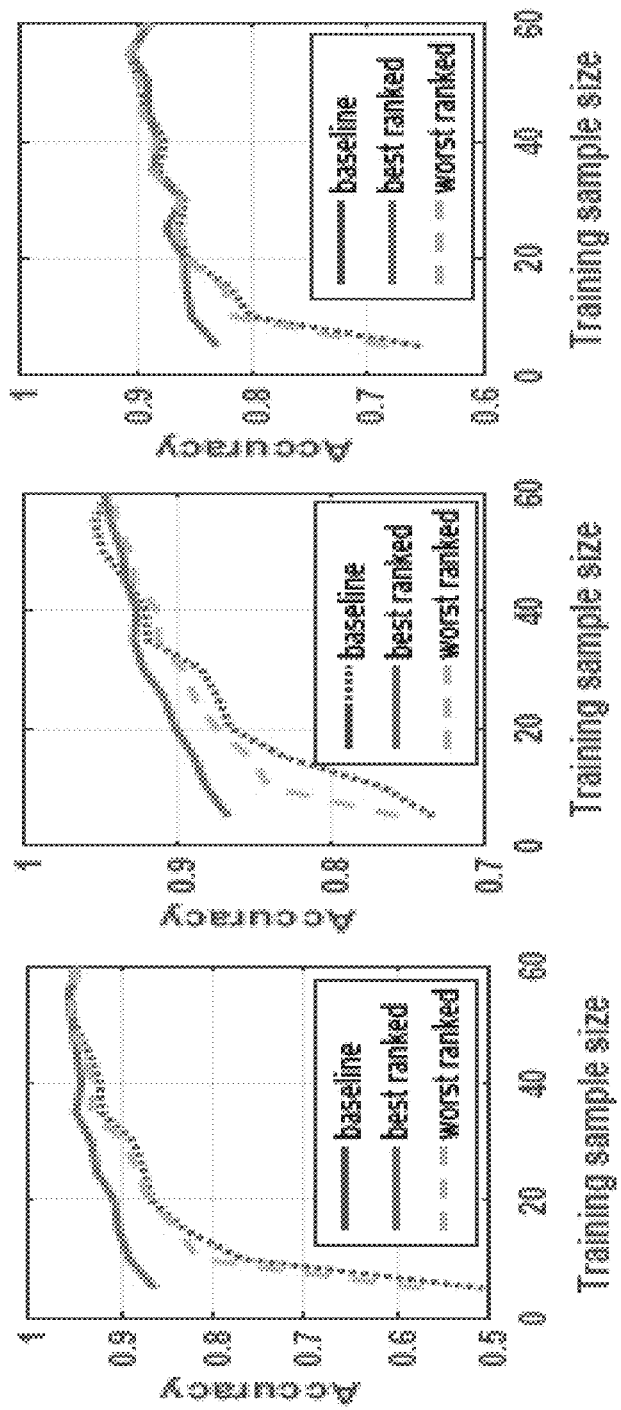
FIG. 29 shows the results on three different testing scenarios.
Figure 30:
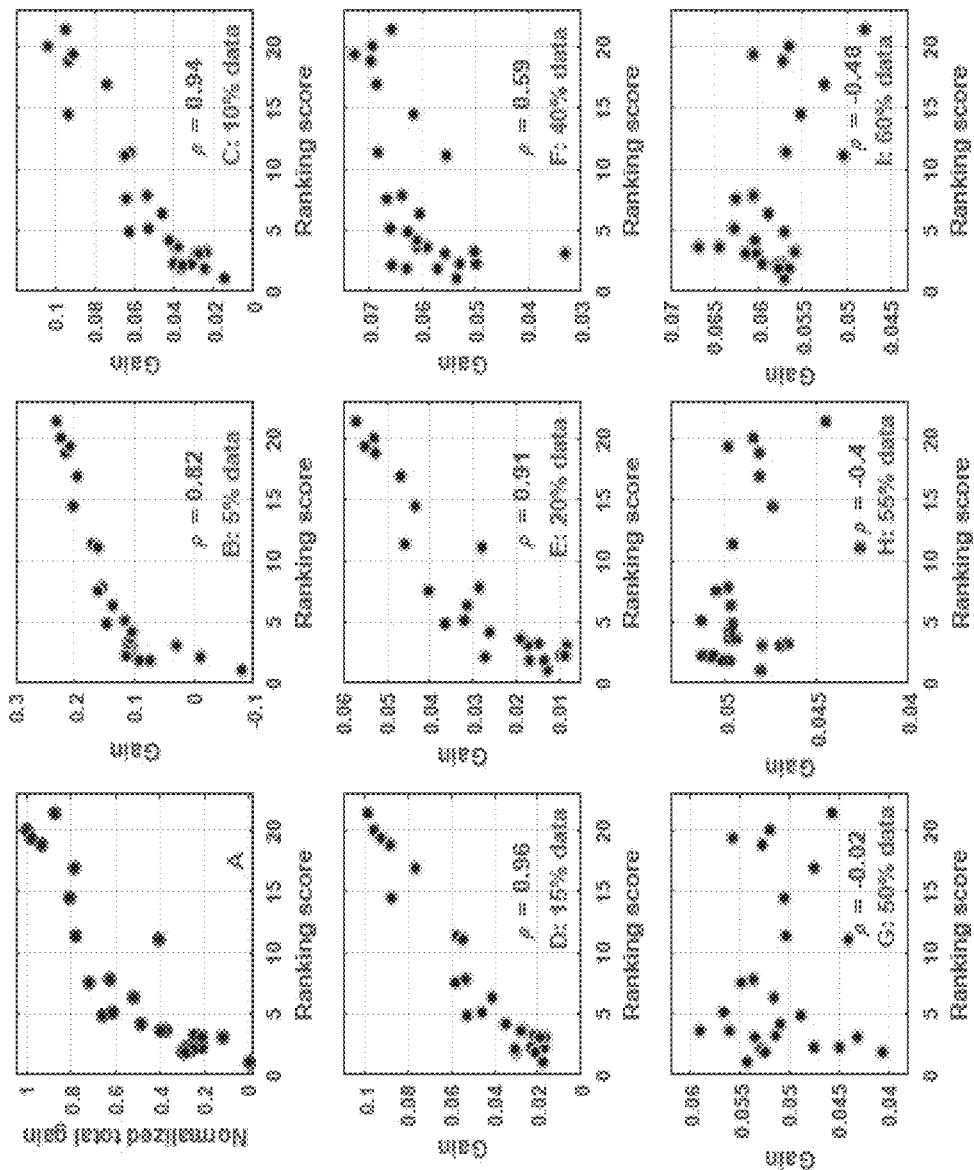
FIG. 30 illustrates correlation between ranking score and performance gain.

Impact of Size of Target Training Set: In this experiment, compare the following: (1) The performance of transfer learning when using the source that was ranked the best against the source that was ranked worst by the proposed source ranking approach. (2) Performance of best and worst ranked against a baseline CNN that was only trained using target training data X with no transfer learning. (3) Performance of the aforementioned CNNs when using a different proportion of target training data. Training was accomplished with 12 different percentage values that ranged from 5% to 60% of the training set in increments of 5. FIG. 29 shows the results on three different testing scenarios. FIG. 30 (left) indicates a performance gain of about 35% with respect to the baseline when only 5% of the target training data is used. The disclosure further observes that the performance gain is more significant when the training data is small in size which is precisely the scenario envisioned in this study. However, as the training size increases, $N^x$ becomes more capable of providing a more comprehensive representation of the "spot" and hence the significance of using an external source task decreases Correlation between Source Ranking and Performance Gain: In A of FIG. 30, the x-axis represents the ranking score of a source task that is computed using the proposed approach, with the top-ranked source having the largest value. The y-axis shows the normalized sum of the overall performance gain achieved by using that source in all the aforementioned 12×6 scenarios (12 different sized training sets, 6 test scenarios). This A of FIG. 30 depicts the overall correlation, when utilizing training set sizes ranging from 5% to 60%. However, it is observed that such a correlation is significantly high when the size of the target training data is small, as can be seen in FIG. 30 (B,C,D,E). Performance gain is measured in terms of the difference between the Area Under the Curve (AUC) values. Since the criterion was specifically designed for small target training sets, this result is desired. From (F to I) in FIG. 6, the training data size increases and it can be seen that performance gain begins to decrease as the target training data is now sufficient for the spot detection problem. Further, as mentioned above, larger values for the ranking score in these situations may actually denote the degree of redundancy. The proposed criterion can be further modified by incorporating a parameter that takes into account the size of the target training size.

Figure 31:
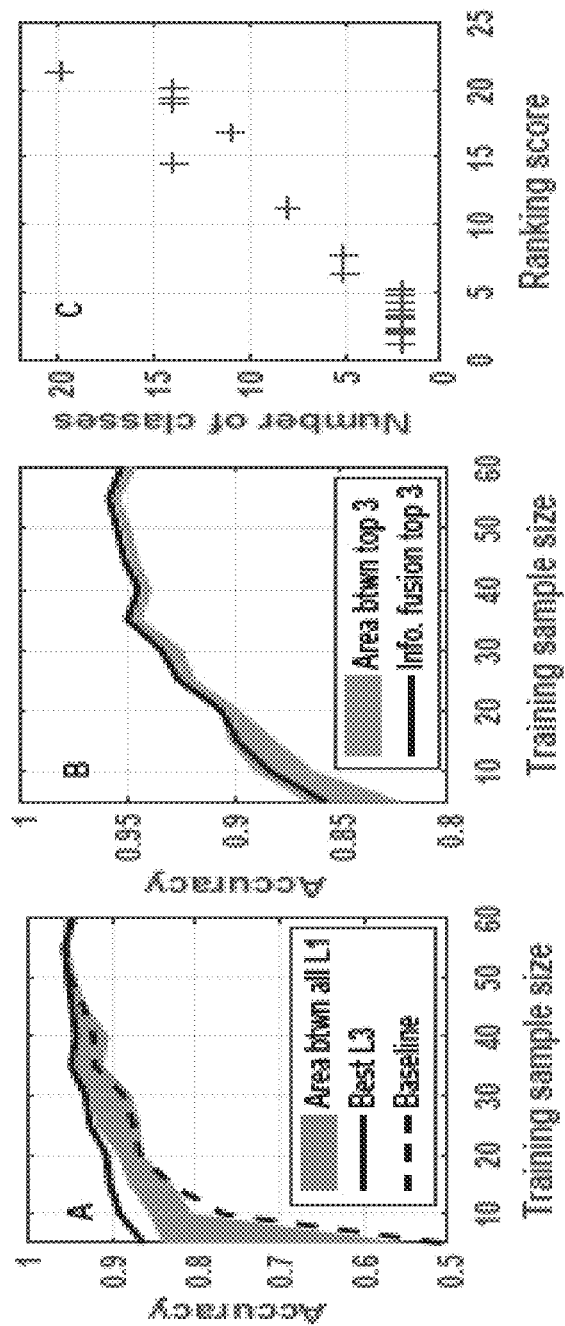
FIG. 31 illustrates performance gain, benefit of information fusion and correlation of ranking score.

Layers to be Transferred: FIG. 31(A) denotes the classification accuracy when (a) only the most general layer (weights from the first convolutional layer only) is transferred from the source CNNs, and (b) all three convolutional layers are transferred from the best ranked source. The shaded region represents the area between the curves plotted when only 1 layer was transferred from all 25 source CNNs (indicated by L1). Experimental results on all 6 testing scenarios clearly show that for sources with higher ranking scores, transferring all layers result in superior performance. For example, FIG. 31(A) shows that the shaded region lies completely under the best ranked source when all three layers of the source CNNs are transferred. The ranking scores may be utilized to determine the number of layers that can be transferred.

Benefit of Information Fusion: In Sec. 3, it was stated that the ranking scores can be utilized to fuse a combination of different sources, in contrast to using only a single source. FIG. 31(B) shows that the fusion approach can overcome any potential errors in ranking the sources. The shaded region displays the area between the top-3 ranked source CNNs. The result of the fused performance is plotted as a line which clearly stays near the top of this area. In cases, where 'poor' sources are ranked higher, using a fusion approach can prove to be more reliable.

Figure 32:
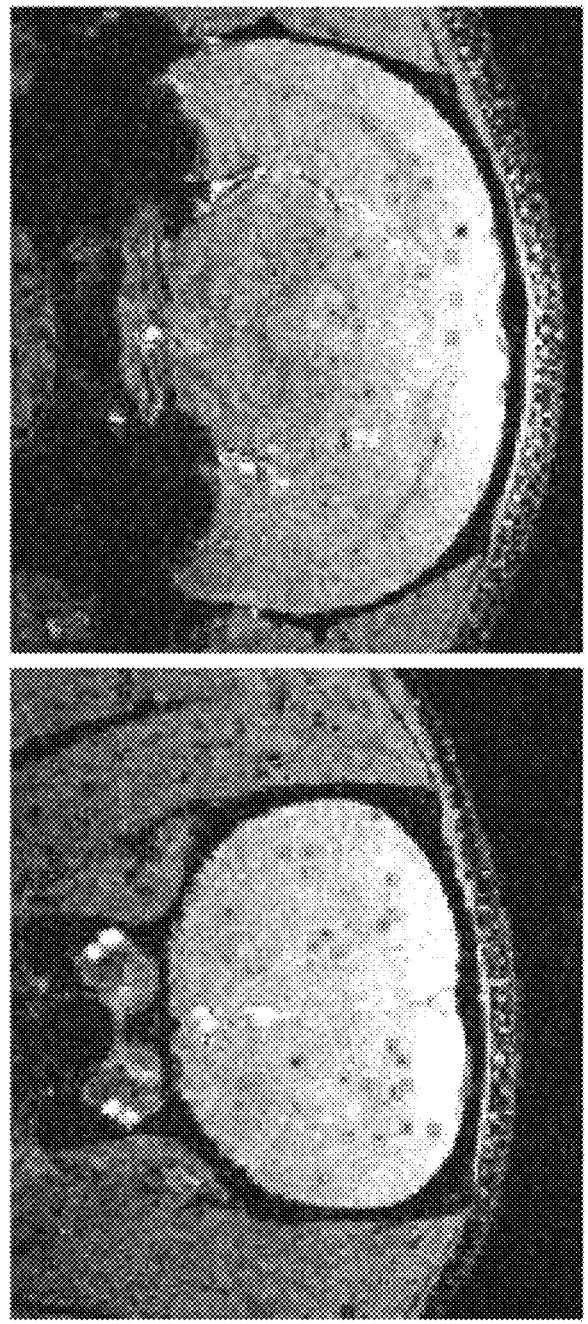
FIG. 32 shows a few detected spots in two different MRI slices.

Establishing a New MRI Stem-Cell Detection: The disclosed approach compares the performance with the other approaches for cell detection in MRI. The disclosed approach conducted experiments using the same setup as other approaches. The disclosed approach achieves a significantly better performance and establishes a new baseline despite using limited data. In comparison to a mean AUC of 89.1% achieved in other approach, the disclosed approach achieves an AUC of 90.86% when using only 25% of the training data and an AUC of 94.6% when the complete training data is used. This clearly shows the practical benefit of adopting the proposed approach in real world tasks with small sized training datasets. A few detected spots in two different MRI slices are shown in FIG. 32.

Relation with Data Characteristics: Based on the empirical results, it can be seen that a source dataset with a large number of classes results in significantly superior performance on the target task compared to a source task with fewer classes. An interesting pattern can be seen in FIG. 31(C) where the number of classes show a high correlation with the ranking score of the source CNN. Note that no explicit knowledge of the source's data characteristic was utilized in this study. This indicates that the source CNNs and—by implication—the proposed approach implicitly capture data characteristics necessary for source selection with respect to a target task.

This disclosure investigates the problem of automated source selection in transfer learning. Transfer learning involves transferring classifier information from the source task to the target task in order to improve the performance of the classifier for the target task. In the context of CNNs, this is a challenging and open problem with limited published work. The novelty of this disclosed approach lies in devising a source selection metric that can assist in the automatic ranking of source tasks to facilitate transfer learning. Experimental results show that automated source selection results in improved classification accuracy on a MRI brain dataset when using only 25% of the original training data. Such an approach will be of tremendous value when there is limited training data, or annotation is expensive and challenging.

Example of Exploiting Labeling Characteristics

The success of CNNs rely on large scale labeled datasets. However, in the problem of spot detection, an MRI scan may only contain a small number of transplanted cells and hence the labeled datasets cannot provide large scale spot samples for training. Further, due to the high appearance variation of spots across MRI scans and within MRI scan, this limitation can affect CNN training to learn robust and more general feature representations modeling MRI spots.

Unlike traditional computer-vision problems, collecting data in clinical arena is highly challenging due to the time consuming surgeries and limited availability of medical experts, MRI machine, materials and animals etc. In addition, once the MRI is obtained, spot labeling adds further to the challenge. Labeling in many medical applications can only be performed by qualified medical experts, and a medical expert who is labeling spots in MRI data, utilize a flexible software to zoom-in, change contrast, etc. to carefully evaluate each spot-like small entity in each 2D slice of an MRI and then use a mouse 'click' for labeling spot entities. This labeling procedure is considered as time consuming and expensive process. Therefore, to learn improved and more accurate spot feature representations from limited spot samples in MRI, a CNN framework may need to be exploited beyond its traditional usage.

Figure 33:
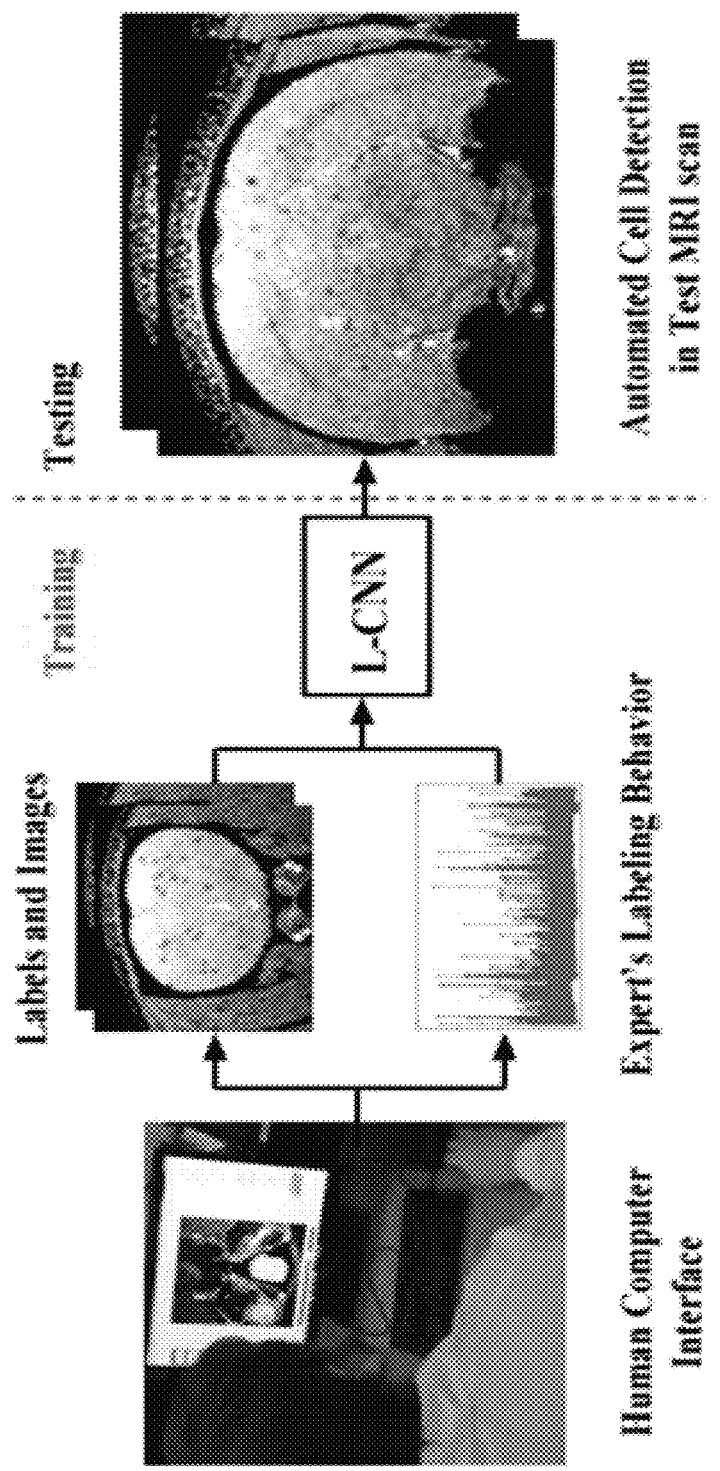
FIG. 33 illustrates the process of CNNs to learn from labeling latency.

As such, the role of incorporating expert's labeling behavior in learning more accurate CNN models for spot detection in MRI may be explored. A human mind process observed characteristics of different visual images differently i.e. consuming different processing times before a response or action is made to the environment. This shall also be true for a human expert who carefully analyze and labels spots in MRI scans. For example, an easy to classify spot may require less analysis whereas a confusing spot may require more analysis and thinking and hence more time to label. Thus, the time taken by an expert to record each label, i.e. labeling latency, is utilized as a variable modeling the labeling behavior of an expert. Therefore, with each labeled spot in MRI, a corresponding labeling latency value provides an additional information which is only available in training and is absent in the testing phase. Further, a medical expert may only label the positive samples in an MRI (the remaining samples in the MRJ are automatically assumed to be negative samples). Labeling latency may only be available for one class, i.e., the positive class. FIG. 33 illustrates the process of CNNs to learn from labeling latency (L-CNN).

In a natural labeling setup, a medical expert only labels the positive samples in MRI and everything else in MRI will form the negative samples of dataset. Meaning, that labeling latency is only available for one class here. This is a common labeling procedure in clinical arena. More examples can be labeling small early tumors or lesions in MRI and CT scans. Note that learning with labeling latency is different from active learning where a user is involved in selectively providing training samples and also different from multi-label learning where a supervised framework has a goal of predicting multiple labels.

However, the paradigm of learning using privileged information (LUPI) can be utilized in an unexpected manner here. Privileged information (also known as side or hidden information) is also available only during training but absent in testing phase. In a classical teacher student example, side information models the comments and extra notes from the teacher that is not available to the student during the testing stage.

Figure 34:
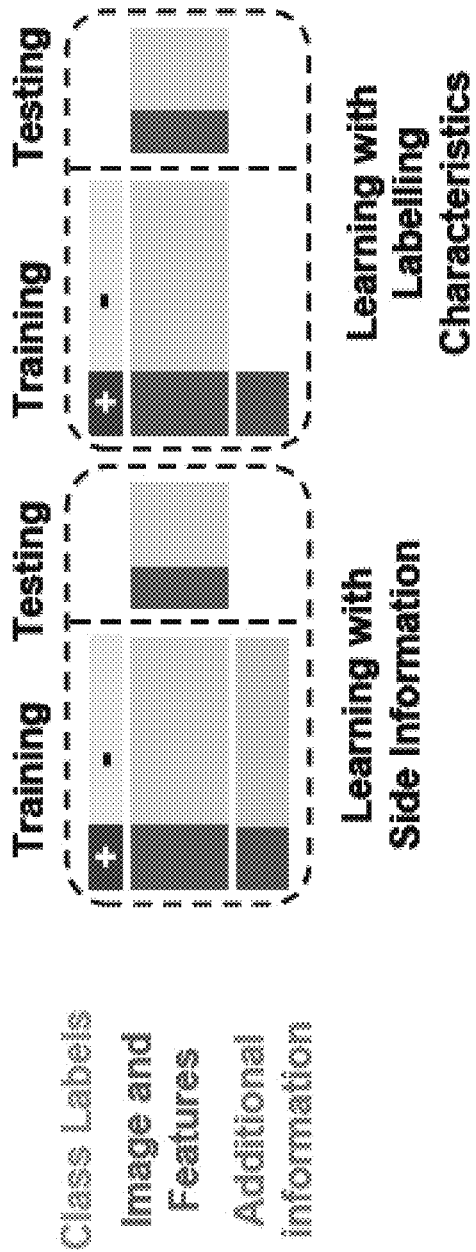
FIG. 34 illustrates the difference between utilizing traditional side information and exploiting labeling latency.

Unfortunately, all the previous LUPI approaches cannot be adopted in the context of supervised classifier learning if the side information is only available for the samples of one class and missing for the remaining classes. In this case, labeling latency is available explicitly for positive class samples only. The difference between utilizing traditional side information and exploiting labeling latency is highlighted in FIG. 34.

However, collecting data in clinical arena may be highly challenging due to the time consuming surgeries and limited availability of medical experts, MRI machine, materials and animals and more resources. In addition, once the MRI is obtained, spot labeling may add further to the challenge.

Labeling in many medical applications may only be performed by qualified medical experts. A medical expert who is labeling spots in MRI data, may utilize a flexible software to zoom-in, change contrast, to carefully evaluate each spot-like small entity in each 2D slice of an MRI and then use a mouse 'click' for labeling spot entities. This labeling procedure is considered as time consuming and expensive process.

Therefore, in order to learn improved and more accurate spot feature representations from limited spot samples in MRI, a CNN framework need to be exploited beyond its regular usage. Thus, the incorporation of expert's labeling behavior in learning more accurate CNN models for spot detection in MRI is disclosed herein.

Figure 35:
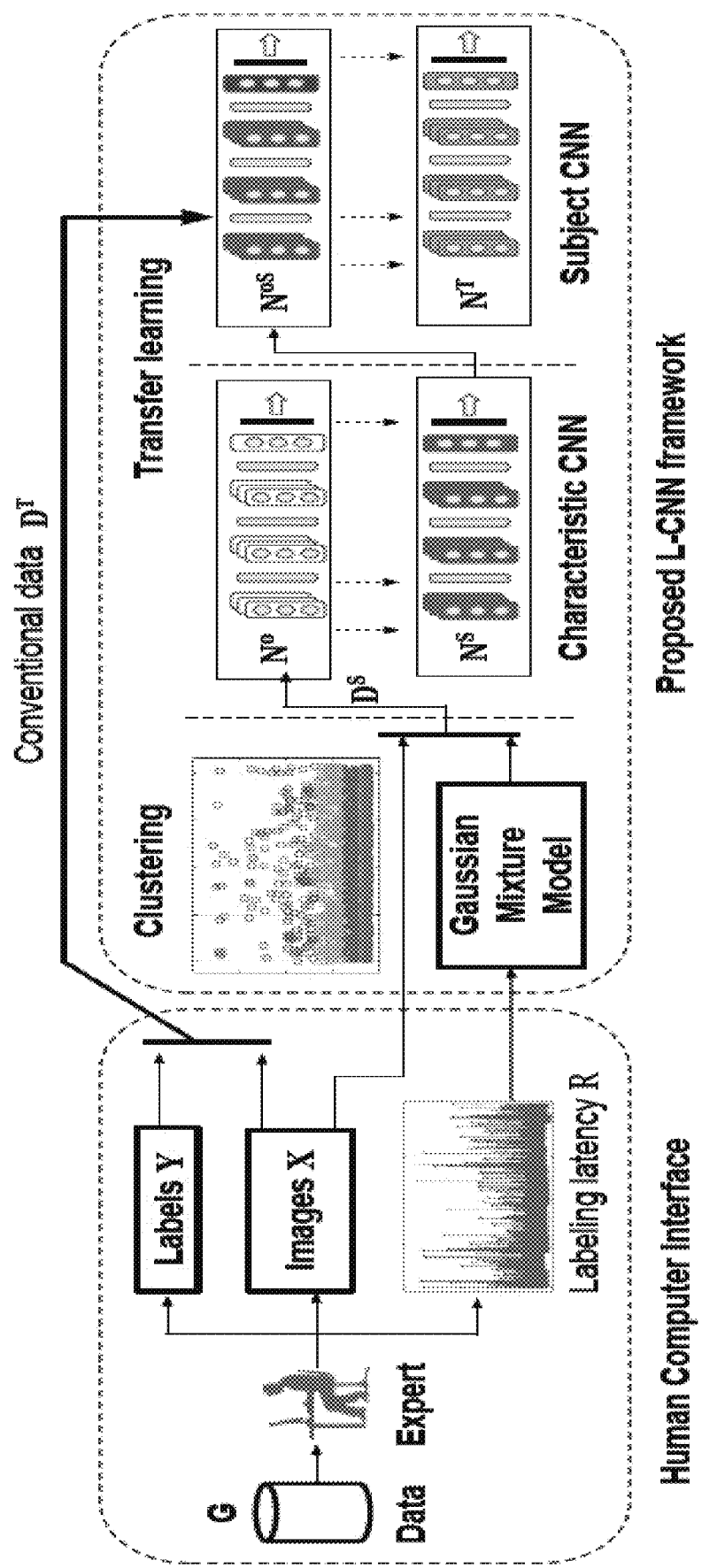
FIG. 35 illustrates the basic architecture of CNNs to learn from labeling latency.

The basic architecture of the proposed approach is shown in FIG. 35. The human computer interface (HCI), takes an MRI scan G as an input and extracts patches X from its slices, where each of the extracted patches can potentially contain a spot. An expert then labels only the positive patches in an interactive manner using an image viewer (e.g., by zooming in, changing image contrast, etc.) resulting in a set of labels Y associated with these patches. Further, the labeling latency value associated with each positive spot label is also recorded. Labeling latency is utilized later as an additional source of information to categorize spot patches. After this, a transfer learning paradigm is adopted for which a source task is defined based on the different spot categories. The goal of the source task is to learn a CNN based feature representation scheme that can differentiate between the spot categories. The target task is to differentiate between spot and non-spot patches using training data that has a limited number of positive samples. Previously, usage of CNNs was thought to be initialization-dependent, and unfavorably impacted when the training data is limited. However, rather than using a randomly initialized CNN, systems and methods proposed herein make unique use of transfers layers, i.e., features from the source CNN to the target CNN, to mitigate and overcome such limitations.

Thus, transfer learning via CNNs is utilized to transfer the learned knowledge about the sub-categories of spots to the general spot vs non-spot problem. Given an imbalanced dataset with small number of spot samples, this approach improves the performance of a CNN. The results obtained in this study are significantly superior to other methods. The details of its main components are explained as follows:

A. Human-Computer Interface

This module has two main goals: First, it interacts with the expert to collect labels and record labeling latency. Second, to make expert interaction useful for machine learning algorithms, it extracts patches (as classification units) from the MRI scan. An extracted patch that contained a clicked pixel is labeled as spot patch (positive class) and a corresponding labeling latency is also available with it. The remaining patches are labeled as non-spot patches.

Collecting Labels: Given an MRI scan G, this module presents a flexible software (zoom, contrast adjustment etc.) for the expert to carefully analyze and click on the spatial location of each spot in each slice of a 3D MRI G. Collectively, these 3D locations are denoted by $\Phi_{[k \times 3]}$ where k represent the total number of clicked points. In addition, the associated time between one click to the next click is also recorded as labeling latency. Labeling latency is considered to be potentially modeling the time taken by an expert to perform analysis and think for a labeling decision. It may be observed that experts label the easier spots first without engaging any detailed analysis. Difficult to label spots, on the other hand, are typically labeled at the end. Every entity that looks small and dark is carefully analyzed by the medical expert by zooming-in and, occasionally, by changing the contrast of the locally selected region. Labeling latency is indirectly related to the cognitive overload involved in labeling a point as a spot. In other words, the labeling latency value is stored in memory in a manner such that it is associated with the clicked point. Factors such as spatial distance between two consecutive clicks can have little or no effect on labeling latency (as small movements on the mouse, translate to large spatial distances on the screen). For simplicity, any possible effect of such factors can be ignored.

Figure 36:
FIG. 36 shows a basic view of MRI image.
Figure 37:
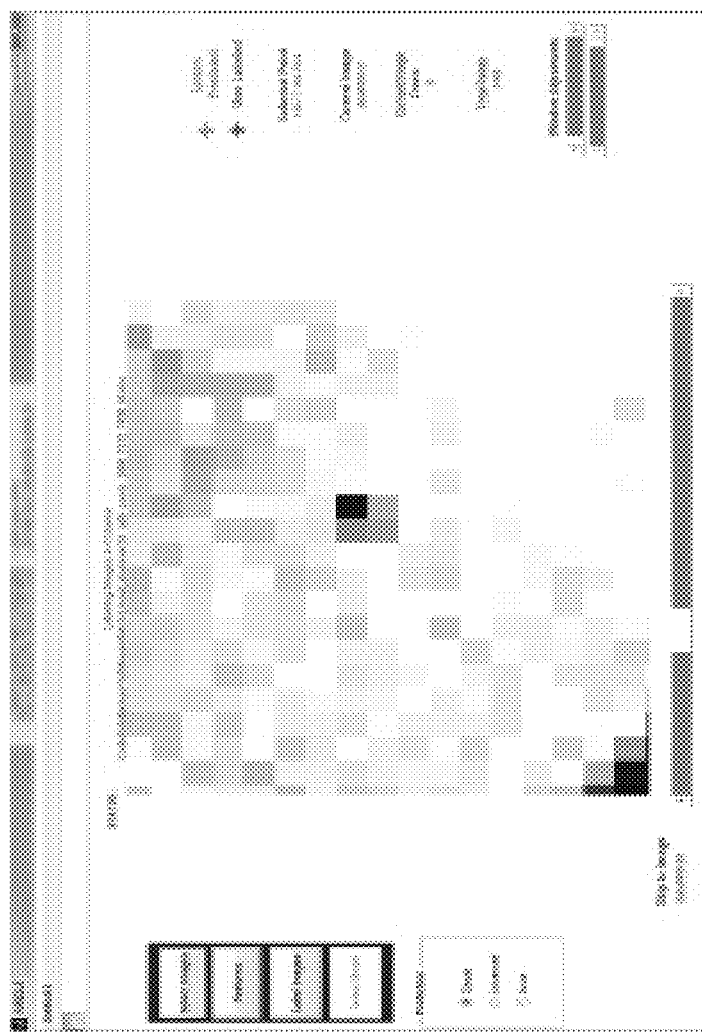
FIG. 37 shows a zooming-view to view a particular spot.
Figure 38:
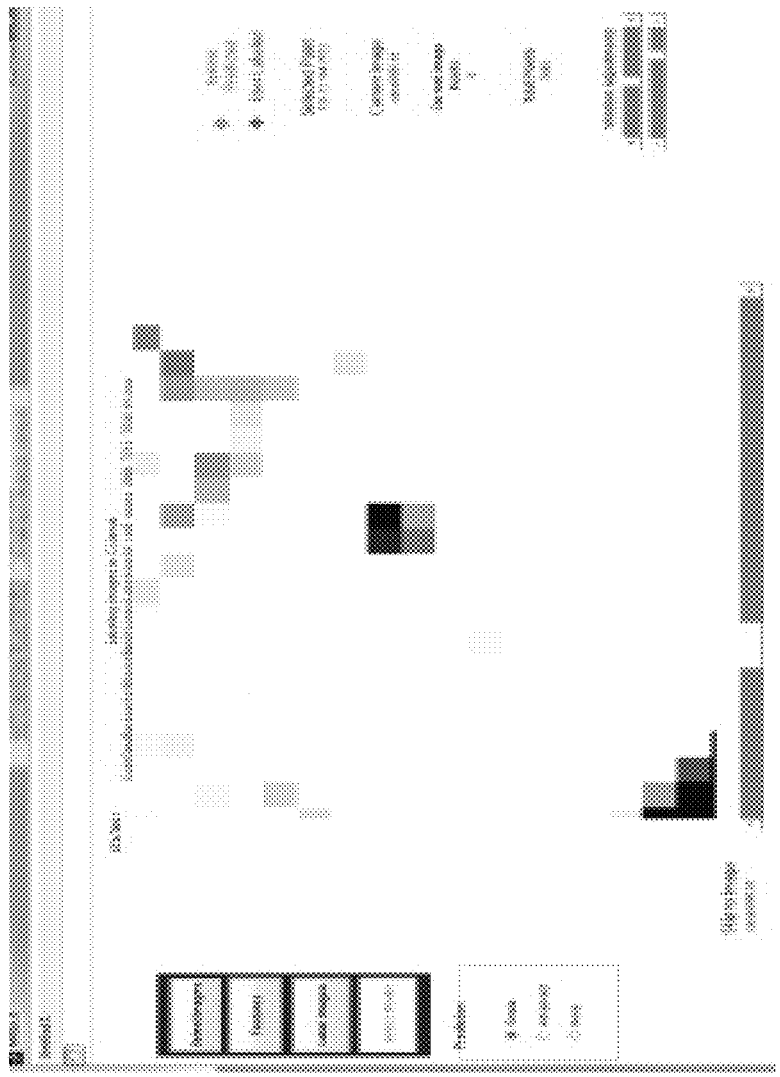
FIG. 38 shows spot analysis with different window adjustment.

It is denoted by $R_{[k \times 1]} = \{r_1, r_2, \ldots r_k\}$. Analyzing small entities in an MRI scan requires an expert to zoom-in to a region of interest for a clearer evaluation and then utilize window adjustments to carefully observe an entity before labeling a spot (as shown in FIG. 36 to FIG. 38). Note that there may be many irregularities (very high values) observed when labeling latency values may be analyzed. For example due to breaks taken by the expert or being involved in any other activity, resulting in high time values.

Figure 39:
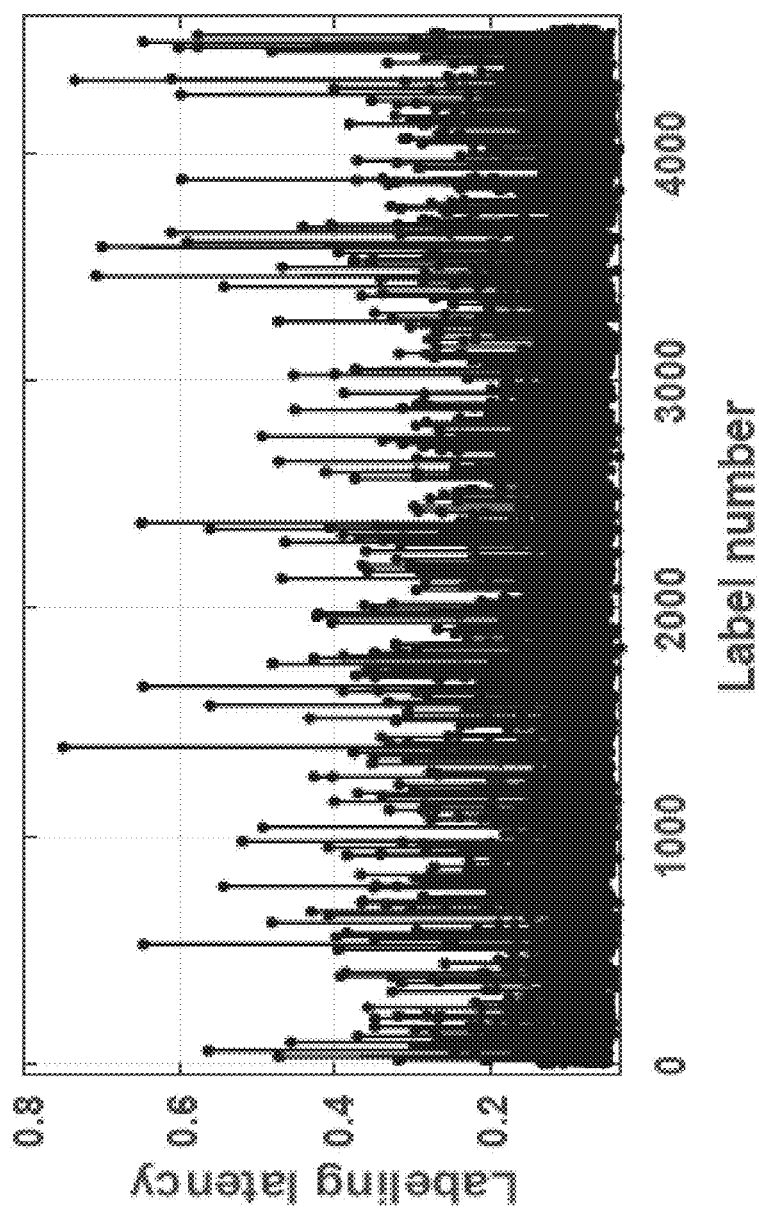
FIG. 39 shows label latency for one MRI scan.

However, according to the experts the value of labeling latency shall not be greater than 45 seconds and hence the values greater than 45 seconds were simply replaced with the mean time taken between labeling clicks. These processed values of labeling latency for one MRI scan are shown in FIG. 39. Factors such as spatial difference between two consecutive clicks can have little or no effect on labeling latency (as even slighter movement of the manual mouse, covers larger spatial distances on the screen). For simplicity and for the proof of concept in this study, any possible effect of such factors is ignored.

Extracting Classification Units:

Now these clicked locations $\Phi$ must be associated with some classification units that are to be extracted from the MRI scan and will be taken as input by the classifier. Classification units containing the clicked locations, will considered as positive samples. Therefore, a superpixel-based strategy, similar to that described above is utilized here to extract a large number of patches from MRI G as classification units denoted by $X = \{x_1, x_2, \ldots x_n\}$. As shown in FIG. 8, for each superpixel in each 2D MRI slice, a patch of size z×z was extracted based on keeping the darkest pixel of a superpixel at its center (as spots appear darker than the surrounding tissue).

Note that a superpixel method is preferred over the standard grid based method for extracting patches as it extract lesser but more relevant patches for further processing and is less susceptible to extracting multiple spots in a single patch. Further, similar to the methods discussed above, it was observed that at such a small scale, a superpixel algorithm performs superior to other superpixel and 3D supervoxel algorithms (such as 3D SLIC) for capturing spot boundaries.

Formally, $X=\{x_1, x_2, \ldots x_n\}$ where each patch $x_i$ has a center $(a_i^1, a_i^2, a_i^q)$. Note that $a^q$ denote the slice number and $a_i^1$, $a_i^2$ represent the 2D spatial location. The distance between the center location of each patch in the MRI is then computed with respect to the clicked locations in $\Phi$. If the smallest distance is less than or equal to a pixel distance of $\tau$, it is considered as a spot patch other-wise, it is considered as a non-spot patch that forms the negative class of the dataset. Thus, $X=\{X_p, X_g\}$ where $X_p=\{x_1, x_2, \ldots, x_k\}$ denote all the spot patches whereas $X_g=\{x_{k+1}, x_{k+2}, \ldots, x_n\}$ represent all the non-spot patches. A labeled dataset $D^T=(X, Y)$ can then be created such that $\forall x_i \in X$ $Z\exists! y_i \in Y$. Further, note that for $x_i \in X_p$, $y_i=1$ and there exists a corresponding labeling latency $r_i$. Whereas if $x_i \in X_g$, $y_i=0$ and there is no corresponding labeling latency value.

B. L-CNN Framework

Clustering:

The variation in labeling latency values can be seen in FIG. 7. The value of labeling latency for a particular spot is governed by the analysis conducted by an expert and by a potentially complex thought process of an expert. Therefore clustering all the available patches in $X_p$ based on the values of their labeling latency, will create sub-categories of spot patches based on the expert's analysis and thinking characteristics. This clustering, despite its apparent simplicity, presents a highly useful information i.e. the information to find sub-categories in the limited positive samples $X_p$. Learning to distinguish between these sub-categories of limited spots can definitely be of use in learning to distinguish between a spot patch and a non-spot patch. Therefore, a gaussian mixture model is utilized here to cluster $X_p$ into m groups where m is the optimum number of clusters selected using the standard Akaike information criterion. Thus, $Xp=\{\cup X_p^j\}_{j=1}^m$ where $X_p^j \subset Xp$ represent the spot patches of $j^{th}$ cluster.

Transfer Learning:

In transfer learning, the knowledge learned to perform one task (source task) is transferred to benefit learning in another task (subject task/target task). In this study, the task of distinguishing sub-categories of spot patches is the source task and the goal task of distinguishing a spot patch from a non-spot patch is the target task. Note that the source here is not generated by external image data but rather the limited spot patches are utilized. However, the clustering labels on these patches are generated by an external information i.e. labeling latency.

Transfer learning is conducted here in two steps: In the first step, the task is learn a CNN based feature representation that can distinguish between the sub-categories of the Xp. Hence, a data set $D^S=\{\cup X_p^j, V_p^j\}_{j=1}^m$ is developed where $V_p^j$ denotes the label ($j^{th}$ cluster number). A CNN $N^S$ is then learned to distinguish between the patches of these clusters. This CNN learning is functionally denoted as $N^S=h(N^o, D^S)$ where $N^o$ represent a randomly initialized CNN whereas $N^S$ denotes a CNN that has learned feature representations to distinguish between the sub-categories (clusters). The CNN architecture customized for this data is shown in FIG. 11. Note that due to small size of the input images, a pooling layer has not been utilized. $N^S$ is called as a characteristic CNN here. In a general L-CNN framework, labeling latency can be replaced by any other labeling characteristic as well e.g. size of bounding boxes. In L-CNN framework, $N^S$ is utilized as a source task's CNN.

In the second step, these learned CNN feature representations in $N^S$ are transplanted to initialize a CNN whose actual goal is to learn feature representations that can separate a spot patch from a non-spot patch, which is the target task. All the convolutional layers are transferred for initialization, however, the fully connected layer is incompatible for transfer due to its structural difference resulting because of the difference in tasks. Therefore, as a standard practice, the fully connected layer is randomly initialized. The resulting CNN is denoted as $N^{o\circ S}$ The CNN learning for the target task can then be denoted as $N^T=h(N^{o\circ S}, D^T)$. Experimental results show that this transfer of knowledge brings an improvement that is not achieved by using a CNN $\overline{N^T}=(N^o, D^T)$ which is only trained to distinguish a spot from a non-spot patch.

In this example, the in vivo MRI database utilized may comprise 5 MRI scans of different Rat brains. 3 of these Rats were injected with Mesenchymal stem cells which appear as dark spots in MRI. From each of these 3 scans about a 100,000 patches are extracted where the spot patches are only about 5000. Due to high inter-class variation of spot patches within one MRI scan and across different MRI scans n, these spot patches represent a small set for comprehensive learning. The labeling latency for each labeled patch was also recorded. Labeling latency values will also be publicly made available with the camera ready version of this paper. Each scan is once used in training and then testing is performed on the remaining two independent MRI scans. This creates 6 testing scenarios.

Experiments were designed to answer the following: How does the L-CNN compares with traditional CNN? What will be the result if random clustering is used rather than GMM based clustering? What is the affect of transferring different number of CNN layers? How does CNN transfer in L-CNN compares with the traditional transfer? How do results obtained in this study compare with the previous methods discussed above?

1. Comparison with Conventional CNN Approach

In this experiment the result of L-CNN is compared with a conventional CNN $\overline{N^T}$ that is randomly initialed and then simply trained using the $D^S$. Results in FIG. 40 clearly demonstrate the performance achieved by L-CNN cannot was not achieved by the conventional CNN learning approach on any of the 6 testing sets. It is interesting to see that exploiting labeling characteristics using L-CNN can provide a performance increase of up to 4% (see test set T3). This result clearly indicate that the expert-computer interaction should be utilized beyond its traditional usage.

2. Comparison with Random Clustering

Figure 40:
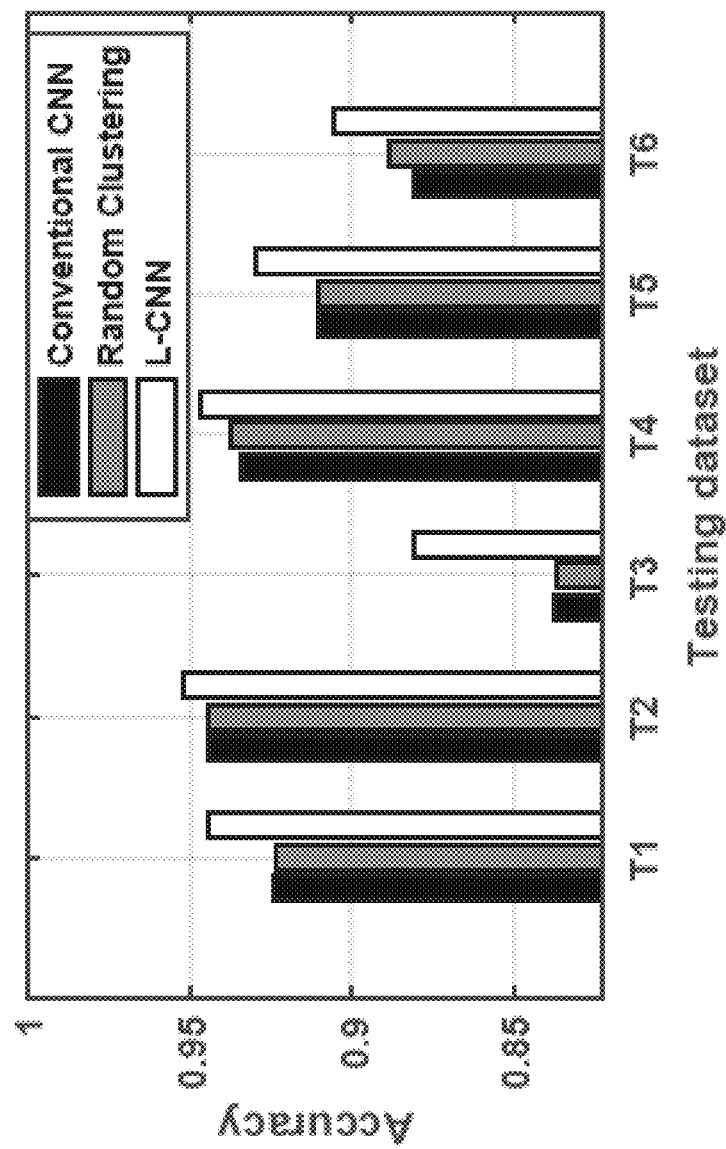
FIG. 40 shows the result and comparison among different methods.

It can be seen that the L-CNN architecture exploits clustering to create sub-categories of the labeled spot patches. In this experiment, the present disclosure investigates results when a random clustering strategy is applied to create random sub-categories rather than using GMM. These results are shown in FIG. 40 for each of the 6 testing sets and also compared with L-CNN's results. In all testing scenarios, L-CNN clearly performs superior when GMM is used rather than random clustering, indicating the usefulness of utilizing labeling latency. Further, it can be seen that the performance observed with random clustering is in general very similar to that observed the conventional CNN.

3. Comparison Using Different Number of Transfer Layers

Figure 41:
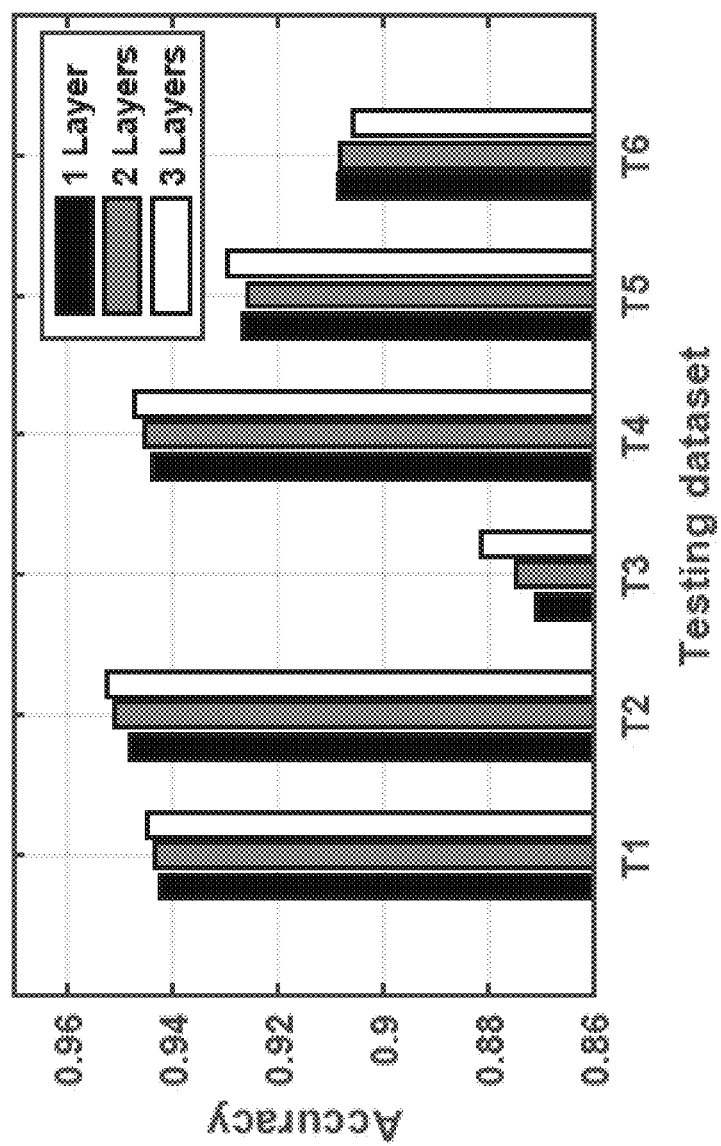
FIG. 41 shows results with different transfer layers.

Since L-CNN adopts transfer learning between CNNs by transplanting network layers from one CNN to another, therefore, in this example the affect of transferring different layers is investigated. The proposed CNN architecture has three convolutional layers and a fully connected layer. Note that the fully connected layer is incompatible for transfer as the output of this layer is different for characteristic and subject CNNs. However, the convolutional layers can all be transferred. The results of transferring different number of convolutional layers are shown in FIG. 41. It is clear that generally transferring all three layers result in superior performance.

4. Comparison with Previous Methods

This approach introduces a novel idea of utilizing labeling latency as an additional input in a supervised framework. The example systems and methods disclosed herein illustrate how such information can be exploited while learning a supervised CNN based approach. An experimental study using a real world MRI database was used to show the practical superiority of proposed L-CNN framework over the transitional CNN learning.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for detecting labeled substances introduced in a subject using magnetic resonance imaging ("MRI"), the system comprising:
    an input configured to receive imaging data obtained from a subject that has been treated with a labeled substance, via an imaging scan of an MRI system;
    at least one processor connected to the input and configured to:
        segment the imaging data into MRI slices comprising pixels;
        subdivide at least one of the MRI slices into a plurality of superpixels, wherein each superpixel of the plurality of superpixels contains more than one pixel and has a size larger than an average size of a unit of the labeled substance;
        identify a subset of superpixels of the plurality of superpixels, wherein each superpixel of the subset is identified as having an intensity profile corresponding to a likelihood of the presence of at least one unit of the labeled substance;
        extract candidate patches from the MRI slice, each candidate patch corresponding to a respective superpixel of the subset of superpixels and being centered at a darkest pixel of the respective superpixel, wherein each candidate patch has a pre-determined size;
        process the candidate patches using an identification module that has been trained to identify units of the labeled substance, to identify units of the labeled substance within the candidate patches;
        associate the identified units of the labeled substance with respective corresponding locations within the imaging data; and
        generate a user indication of occurrences of the identified units of the labeled substance in the MRI slices, based on such identification and association; and
    a display connected to the processor to display a visual representation of the user indication of the occurrences of the identified units of the labeled substance.

2. The system of claim 1, wherein the user indication is an image showing locations of each of the identified units of the labeled substance.

3. The system of claim 1, wherein the user indication includes a quantity of the identified units of the labeled substance.

4. The system of claim 1, wherein the processor is further programmed to receive a set of initial imaging data from an initial scan prior to the imaging scan, and output MRI images to the display without the user indication of the occurrences of the identified units of the labeled substance, and wherein the system further includes a user input device connected to the processor to allow a training user to tag depictions of the units of the labeled substances in the images.

5. The system of claim 4, wherein the processor is further programmed to use the tagged depictions of the units of the labeled substance in the images as learning inputs to the identification module, to improve accuracy of the module's ability to identify the units of the labeled substance.

6. The system of claim 5, wherein the learning inputs are ranked based on the accuracy of the module's ability to identify units of the labeled substance.

7. The system of claim 5, wherein labeling latency for the tagged depictions is used to improve the accuracy of the module's ability to identify the units of the labeled substance.

8. The system of claim 5, wherein the initial scan is of the subject.

9. The system of claim 5, wherein the initial scan is of a region of interest of a second subject.

10. A method for tracking locations and quantity of substances introduced in a subject using magnetic resonance imaging ("MRI"), the method comprising:
    obtaining a substance that comprises an MRI contrast compound;
    administering the substance into a region of interest of a scan subject;
    performing an imaging scan of a portion of the scan subject comprising the region of interest;
    obtaining an imaging data set from the scan;
    reducing the data set into pixel groupings based on intensity profiles, wherein the pixel groupings have a pixel size larger than an expected pixel size of a unit of the MRI contrast compound;
    identifying pixel groupings likely to contain units of the MRI contrast compound;
    extracting candidate pixel matrices from the imaging data, wherein each candidate pixel matrix corresponds to a respective pixel grouping of the identified pixel groupings and is centered at a darkest pixel of the respective pixel grouping, wherein each candidate pixel matrix comprises a pre-determined number of pixels;
    determining whether each candidate pixel matrix of the candidate pixel matrices contains one or more pixels representing a unit of the substance to identify units of the substance, using a machine learning (ML) module that has been trained to identify such units within MRI imaging data;
    quantifying the identified units of the substance and associating each of the identified units of the substance with a location within the imaging data set; and
    displaying a visual representation to a user of the quantity and the locations of the identified units of the substance.

11. The method of claim 10, wherein the units of the substance represent individual cells administered to the scan subject.

12. The method of claim 10, further comprising, prior to obtaining the imaging data set, obtaining a training data set comprising MRI image data from a training subject, displaying the images to a healthcare professional, and creating initial learning inputs for the ML module that comprise tagged depictions that are defined based upon the user tagging depictions of units of a substance containing an MRI contrast compound in images based on the training data set.

13. The method of claim 12, wherein the training subject is not the same subject as the scan subject, and further wherein the learning inputs are used as training information to train the ML module to achieve an average of at least 85% accuracy in identifying units of the MRI contrast compound in candidate pixel matrices obtained from scans of scan subjects.

14. The method of claim 12, wherein labeling latency for the tagged depictions is used to improve accuracy of the ML module to identify units of the substance in image data obtained from imaging scans of the scan subject.

15. A system for tracking magnetically-labeled substances in a subject comprising:
 a user input device;
 a display device;
 an MRI input configured to receive 3D image data obtained from an MRI scan of a region of interest of a subject;
 a processor electrically connected to the user input device, the display device, and the MRI input, the processor configured to:
  receive via the MRI input a first set of imaging data from an MRI scan of a training subject,
  display via the display device a training interface comprising images of a region of interest of the training subject, based on the first set of imaging data;
  receive input from a user via the training interface, tagging at least one spatial location of the images as corresponding to the presence of at least one unit of the magnetically-labeled substance;
  characterize, for purposes of machine learning training, the imaging data corresponding to the at least one spatial location as representing a positive identification of a presence of a unit of the magnetically-labeled substance;
  initially train a machine learning module to identify presence and locations of units of the magnetically-labeled substance via at least the characterized, tagged imaging data and non-tagged image data; and
  after the machine learning module has been initially trained, permit a user to choose, via a user interface, whether to:
   perform an imaging scan of a scan subject different than the training subject and use the trained machine learning module to automatically track a quantity of and locations of units of the magnetically labeled substance by extracting candidate patches centered at a darkest spot of superpixels of the imaging scan, or
   input further tagging information for a scan of the scan subject to further train the machine learning module.

16. The system of claim 15, wherein the machine learning module is a multi-layer deep convolutional neural network operating in a transfer learning paradigm, configured to use MRI imaging data as its target data.

17. The system of claim 15, wherein the processor is further programmed to extract a patch of a predetermined number of pixels of the first set of imaging data based on each tagged spatial location, and use such extracted patches for initial training of the machine learning module.

18. The system of claim 17, wherein the extracted patches in total comprise less than 10% of the data of the first set of imaging data.

19. The system of claim 15, wherein the non-tagged image data comprises non-MRI image data, and wherein the processor is further programmed to use the non-MRI image data as source data for the initial training of the machine learning module in addition to the characterized, tagged imaging data.

20. The system of claim 15, wherein the tagged spatial locations represent individual transplanted cells in the training subject that have been magnetically labeled using a polymer-encapsulated superparamagnetic compound.

21. A system for detecting labeled substances introduced in a subject using magnetic resonance imaging ("MRI"), the system comprising:
 a data processing unit electrically connected to receive MRI imaging signals and convert them to MRI imaging data;
 at least one processor connected to the data processing unit and to a memory having stored thereon a set of instructions which, when executed by the at least one processor, cause the at least one processor to:
  subdivide at least one slice of the MRI imaging data into superpixels, wherein each superpixel contains more than one pixel;
  identify superpixels having an intensity profile corresponding to a likelihood of at least one unit of the labeled substance being present;
  extract candidate patches from the MRI slice based on said identification of superpixels, wherein each candidate patch has a pre-determined size relating to a size of the labeled substance, is positioned within the MRI slice in association with the likely respective unit of the labeled substance, and is centered at a darkest pixel of a corresponding superpixel of the superpixels; and
  process the candidate patches using an algorithm trained to identify units of the labeled substance, to identify whether each candidate patch contains an individual unit of the labeled substance;
  associate the data comprising the identification of the individual unit of the labeled substance with a corresponding location within the imaging data; and
  generate a user indication of the presence of the labeled substance in the MRI slices, based on such identification and association; and
 a display connected to the processor to display a visual representation of the user indication of the presence of the labeled substance.

* * * * *